(12) United States Patent
Rosenthal et al.

(10) Patent No.: US 7,807,165 B2
(45) Date of Patent: Oct. 5, 2010

(54) ANTIBODIES DIRECTED AGAINST AMYLOID-BETA PEPTIDE AND METHODS USING SAME

(75) Inventors: Arnon Rosenthal, Woodside, CA (US); Jaume Pons, San Carlos, CA (US); Wei-Hsien Ho, Palo Alto, CA (US); Jan Markus Grimm, Menlo Park, CA (US)

(73) Assignee: Rinat Neuroscience Corp., South San Francisco, CA (US)

( * ) Notice: Subject to any disclaimer, the term of this patent is extended or adjusted under 35 U.S.C. 154(b) by 942 days.

(21) Appl. No.: 11/195,207

(22) Filed: Aug. 1, 2005

(65) Prior Publication Data

US 2006/0057702 A1    Mar. 16, 2006

Related U.S. Application Data

(60) Provisional application No. 60/592,494, filed on Jul. 30, 2004, provisional application No. 60/653,197, filed on Feb. 14, 2005, provisional application No. 60/676,093, filed on Apr. 29, 2005.

(51) Int. Cl.
*A61K 39/395* (2006.01)
*A61K 39/00* (2006.01)

(52) U.S. Cl. ............... 424/141.1; 424/130.1; 424/133.1; 424/152.1

(58) Field of Classification Search ........................ None
See application file for complete search history.

(56) References Cited

U.S. PATENT DOCUMENTS

| | | |
|---|---|---|
| 4,403,112 A | 9/1983 | Modafferi |
| 4,485,045 A | 11/1984 | Regen |
| 4,544,545 A | 10/1985 | Ryan et al. |
| 4,603,112 A | 7/1986 | Paoletti et al. |
| 4,666,829 A | 5/1987 | Glenner et al. |
| 4,676,980 A | 6/1987 | Segal et al. |
| 4,683,195 A | 7/1987 | Mullis et al. |
| 4,683,202 A | 7/1987 | Mullis |
| 4,751,180 A | 6/1988 | Cousens et al. |
| 4,754,065 A | 6/1988 | Levenson et al. |
| 4,769,330 A | 9/1988 | Paoletti et al. |
| 4,777,127 A | 10/1988 | Suni et al. |
| 4,782,014 A | 11/1988 | Serban et al. |
| 4,800,159 A | 1/1989 | Mullis et al. |
| 4,816,567 A | 3/1989 | Cabilly et al. |
| 4,891,268 A | 1/1990 | Fourez et al. |
| 4,935,233 A | 6/1990 | Bell et al. |
| 5,013,556 A | 5/1991 | Woodle et al. |
| 5,017,487 A | 5/1991 | Stunnenberg et al. |
| 5,047,335 A | 9/1991 | Paulson et al. |
| 5,075,109 A | 12/1991 | Tice et al. |
| 5,164,295 A | 11/1992 | Kisilevsky et al. |
| 5,219,740 A | 6/1993 | Miller et al. |
| 5,225,539 A | 7/1993 | Winter |
| 5,231,000 A | 7/1993 | Majocha et al. |
| 5,231,170 A | 7/1993 | Averback |
| 5,234,814 A | 8/1993 | Card et al. |
| 5,262,332 A | 11/1993 | Selkoe |
| 5,270,165 A | 12/1993 | Van Nostrand et al. |
| 5,278,299 A | 1/1994 | Wong et al. |
| 5,385,915 A | 1/1995 | Buxbaum et al. |
| 5,422,120 A | 6/1995 | Kim |
| 5,441,870 A | 8/1995 | Seubert et al. |
| 5,500,362 A | 3/1996 | Robinson et al. |
| 5,510,261 A | 4/1996 | Goochee et al. |
| 5,525,126 A | 6/1996 | Basu et al. |
| 5,530,101 A | 6/1996 | Queen et al. |
| 5,545,566 A | 8/1996 | Growden et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,589,154 A | 12/1996 | Anderson |
| 5,593,846 A | 1/1997 | Schenk et al. |
| 5,604,102 A | 2/1997 | McConlogue et al. |

(Continued)

FOREIGN PATENT DOCUMENTS

EP    0 345 242 A2    12/1989

(Continued)

OTHER PUBLICATIONS

Johnson—Wood, K. et al. (Feb. 1997). "Amyloid Precursor Protein Processing and Aβ$_{42}$ Deposition in a Transgenic Mouse Model of Alzheimer Disease," *Proc. Natl. Acad. Sci. USA* 94:1550-1555.
De Felice, F.G. et al. (Dec. 2002). "β-Amyloid Production, Aggregation, and Clearance as Targets for Therapy in Alzheimer's Disease," *Cell. Mol. Neurobiol.* 22(5/6):545-563.
Small, D.H. et al. (Aug. 2001). "Alzheimer's Disease and Aβ Toxicity: From Top to Bottom," *Nat. Rev. Neurosci.* 2:595-598.
St. George-Hyslop, P.H. et al. (Jul. 8, 1999). "Antibody Clears Senile Plaques," *Nature* 400(6740):116-117.
Adelman, J.P. et al. (1983). "In Vitro Deletional Mutagenesis for Bacterial Production of the 20,000-Dalton Form of Human Petuitary Growth Hormone," *DNA* 2(3):183-193.
Akiyama, H. et al. (Feb. 2004). "Specificity of Mechanisms for Plaque Removal after Aβ Immunotherapy for Alzheimer Disease," *Nature Medicine* 10(2):117-119.

(Continued)

*Primary Examiner*—Daniel E. Kolker
*Assistant Examiner*—Gregory S Emch
(74) *Attorney, Agent, or Firm*—Gregg C. Benson; Garth Butterfield; Raquel M. Alvarez

(57) ABSTRACT

Monoclonal antibody 9TL and antibodies derived from 9TL directed against amyloid-beta peptide and methods of using same for diagnosing and treatment of Alzheimer's disease and Aβ peptide associated diseases are described. Methods of using antibodies directed against amyloid-beta peptide having impaired effector function for treatment of Alzheimer's disease and Aβ peptide associated diseases are also described.

68 Claims, 14 Drawing Sheets

U.S. PATENT DOCUMENTS

Figure 2:
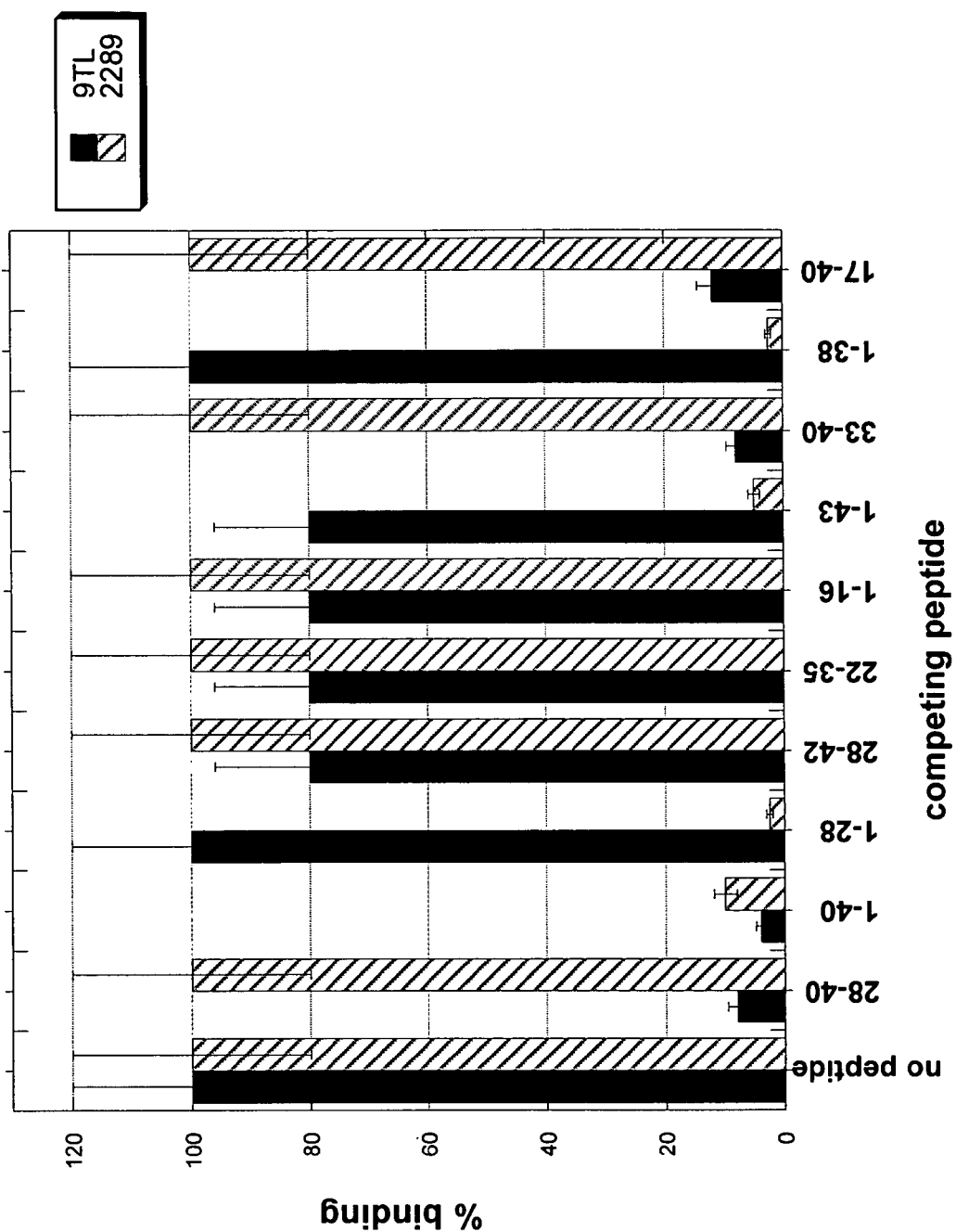

| | | |
|---|---|---|
| 5,625,126 A | 4/1997 | Lonberg et al. |
| 5,631,168 A | 5/1997 | Growdon et al. |
| 5,633,425 A | 5/1997 | Lonberg et al. |
| 5,652,092 A | 7/1997 | Vitek et al. |
| 5,661,016 A | 8/1997 | Lonberg et al. |
| 5,677,425 A | 10/1997 | Bodmer et al. |
| 5,679,531 A | 10/1997 | Konig et al. |
| 5,688,651 A | 11/1997 | Solomon |
| 5,693,478 A | 12/1997 | Vitek et al. |
| 5,693,753 A | 12/1997 | Konig et al. |
| 5,693,761 A | 12/1997 | Queen et al. |
| 5,693,762 A | 12/1997 | Queen et al. |
| 5,714,471 A | 2/1998 | Rowe et al. |
| 5,721,130 A | 2/1998 | Seubert et al. |
| 5,733,743 A | 3/1998 | Johnson et al. |
| 5,739,277 A | 4/1998 | Presta et al. |
| 5,750,349 A | 5/1998 | Suzuki et al. |
| 5,750,373 A | 5/1998 | Garrard et al. |
| 5,786,180 A | 7/1998 | Konig et al. |
| 5,807,715 A | 9/1998 | Morrison et al. |
| 5,814,482 A | 9/1998 | Dubensky, Jr. et al. |
| 5,821,337 A | 10/1998 | Carter et al. |
| 5,851,996 A | 12/1998 | Kline |
| 5,866,692 A | 2/1999 | Shitara et al. |
| 5,891,991 A | 4/1999 | Wasco et al. |
| 5,942,400 A | 8/1999 | Anderson et al. |
| 5,955,317 A | 9/1999 | Suzuki et al. |
| 5,958,684 A | 9/1999 | Van Leeuwen et al. |
| 5,962,463 A | 10/1999 | Nitsch et al. |
| 5,976,817 A | 11/1999 | Davies-Heerema et al. |
| 5,997,867 A | 12/1999 | Waldmann et al. |
| 6,054,297 A | 4/2000 | Carter et al. |
| 6,071,463 A | 6/2000 | De'ath |
| 6,107,029 A | 8/2000 | Giordano |
| 6,107,050 A | 8/2000 | Alkon et al. |
| 6,114,133 A | 9/2000 | Seubert et al. |
| 6,143,171 A | 11/2000 | Van Aarsen |
| 6,180,370 B1 | 1/2001 | Queen et al. |
| 6,180,377 B1 | 1/2001 | Morgan et al. |
| 6,187,756 B1 | 2/2001 | Lee et al. |
| 6,210,671 B1 | 4/2001 | Co |
| 6,221,645 B1 | 4/2001 | Chrysler et al. |
| 6,221,670 B1 | 4/2001 | Cordell et al. |
| 6,255,054 B1 | 7/2001 | Hugon et al. |
| 6,265,150 B1 | 7/2001 | Terstappen et al. |
| 6,294,171 B2 | 9/2001 | McMichael |
| 6,294,340 B1 | 9/2001 | Strittmatter et al. |
| 6,329,155 B1 | 12/2001 | Nitsch et al. |
| 6,331,415 B1 | 12/2001 | Cabilly et al. |
| 6,350,861 B1 | 2/2002 | Co et al. |
| 6,376,471 B1 | 4/2002 | Lawrence, III et al. |
| 6,413,942 B1 | 7/2002 | Felgner et al. |
| 6,436,908 B1 | 8/2002 | Koch et al. |
| 6,548,640 B1 | 4/2003 | Winter |
| 6,573,276 B2 | 6/2003 | Hock et al. |
| 6,582,945 B1 | 6/2003 | Raso |
| 6,710,226 B1 | 3/2004 | Schenk |
| 6,743,427 B1 | 6/2004 | Schenk |
| 6,750,324 B1 | 6/2004 | Schenk et al. |
| 6,761,888 B1 | 7/2004 | Schenk |
| 6,787,523 B1 | 9/2004 | Schenk |
| 6,787,637 B1 | 9/2004 | Schenk |
| 6,815,175 B2 | 11/2004 | Weksler et al. |
| 6,872,554 B2 | 3/2005 | Raso |
| 2001/0018053 A1 | 8/2001 | McMichael |
| 2002/0009445 A1 | 1/2002 | Du et al. |
| 2002/0019335 A1 | 2/2002 | Solomon et al. |
| 2002/0028473 A1 | 3/2002 | Averback |
| 2002/0086847 A1 | 7/2002 | Chain |
| 2002/0094335 A1 | 7/2002 | Chalifour et al. |
| 2002/0102261 A1 | 8/2002 | Raso |
| 2002/0136718 A1 | 9/2002 | Raso |
| 2002/0197258 A1 | 12/2002 | Ghanbari et al. |
| 2002/0197831 A1 | 12/2002 | Todd et al. |
| 2003/0068316 A1 | 4/2003 | Klein et al. |
| 2003/0073655 A1 | 4/2003 | Chain |
| 2003/0108551 A1 | 6/2003 | Nicolau et al. |
| 2003/0147882 A1 | 8/2003 | Solomon et al. |
| 2003/0147887 A1 | 8/2003 | Wang et al. |
| 2003/0165496 A1 | 9/2003 | Basi et al. |
| 2003/0235872 A1 | 12/2003 | Small et al. |
| 2003/0235897 A1 | 12/2003 | Raso |
| 2004/0038302 A1 | 2/2004 | Nitsch et al. |
| 2004/0081657 A1 | 4/2004 | Schenk |
| 2004/0087777 A1 | 5/2004 | Basi et al. |
| 2004/0146512 A1 | 7/2004 | Rosenthal et al. |
| 2004/0197831 A1 | 10/2004 | Weksler et al. |
| 2004/0219146 A1 | 11/2004 | Schenk |
| 2004/0241164 A1 | 12/2004 | Bales et al. |
| 2004/0265308 A1 | 12/2004 | Schenk |
| 2005/0019328 A1 | 1/2005 | Schenk |
| 2005/0019330 A1 | 1/2005 | Schenk |
| 2005/0048049 A1 | 3/2005 | Schenk |
| 2005/0129691 A1 | 6/2005 | Gerlai |
| 2005/0130233 A1 | 6/2005 | Nitsch et al. |
| 2005/0239169 A1 | 10/2005 | Nitsch et al. |
| 2006/0057701 A1 | 3/2006 | Rosenthal et al. |
| 2006/0292152 A1 | 12/2006 | Rosenthal et al. |
| 2007/0160616 A1 | 7/2007 | Rosenthal et al. |

FOREIGN PATENT DOCUMENTS

| | | |
|---|---|---|
| EP | 0 345 242 A3 | 12/1989 |
| EP | 0 391 714 A2 | 10/1990 |
| EP | 0 391 714 A3 | 10/1990 |
| EP | 0 440 619 B1 | 8/1991 |
| EP | 0 519 596 B1 | 12/1992 |
| EP | 0 524 968 B1 | 2/1993 |
| EP | 0 613 007 A2 | 8/1994 |
| EP | 0 613 007 A3 | 8/1994 |
| EP | 0 683 234 B1 | 11/1995 |
| EP | 1 160 256 A2 | 12/2001 |
| EP | 1 160 256 A3 | 12/2001 |
| EP | 1 172 378 A1 | 1/2002 |
| EP | 1 666 061 A1 | 6/2006 |
| GB | 2 200 651 A | 8/1988 |
| WO | WO-87/04462 A1 | 7/1987 |
| WO | WO-89/01973 A2 | 3/1989 |
| WO | WO-89/01973 A3 | 3/1989 |
| WO | WO-90/07936 A1 | 7/1990 |
| WO | WO-90/09789 A2 | 9/1990 |
| WO | WO-90/11092 A1 | 10/1990 |
| WO | WO-90/12870 A1 | 11/1990 |
| WO | WO-90/14841 A1 | 12/1990 |
| WO | WO-91/00360 A1 | 1/1991 |
| WO | WO-91/02805 A2 | 3/1991 |
| WO | WO-91/04339 A1 | 4/1991 |
| WO | WO-91/14445 A1 | 10/1991 |
| WO | WO-91/18926 A1 | 12/1991 |
| WO | WO-92/09699 A1 | 6/1992 |
| WO | WO-92/20373 A1 | 11/1992 |
| WO | WO-93/03769 A1 | 3/1993 |
| WO | WO-93/06213 A1 | 4/1993 |
| WO | WO-93/10218 A1 | 5/1993 |
| WO | WO-93/11230 A1 | 6/1993 |
| WO | WO-93/19191 A1 | 9/1993 |
| WO | WO-93/19194 A1 | 9/1993 |
| WO | WO-93/25234 A1 | 12/1993 |
| WO | WO-93/25698 A1 | 12/1993 |
| WO | WO-94/03622 A1 | 2/1994 |
| WO | WO-94/04690 A1 | 3/1994 |
| WO | WO-94/12649 A2 | 6/1994 |
| WO | WO-94/12649 A3 | 6/1994 |
| WO | WO-94/23697 A1 | 10/1994 |

| | | | |
|---|---|---|---|
| WO | WO-94/28938 A1 | 12/1994 |
| WO | WO-95/00655 A1 | 1/1995 |
| WO | WO-95/07944 A3 | 3/1995 |
| WO | WO-95/07994 A2 | 3/1995 |
| WO | WO-95/11984 A2 | 5/1995 |
| WO | WO-95/11984 A3 | 5/1995 |
| WO | WO-95/13084 A1 | 5/1995 |
| WO | WO-95/13796 A1 | 5/1995 |
| WO | WO-95/16917 A1 | 6/1995 |
| WO | WO-95/30763 A2 | 11/1995 |
| WO | WO-95/30763 A3 | 11/1995 |
| WO | WO-96/15799 A1 | 5/1996 |
| WO | WO-96/17072 A2 | 6/1996 |
| WO | WO-96/17072 A3 | 6/1996 |
| WO | WO-96/18900 A1 | 6/1996 |
| WO | WO-96/25435 A1 | 8/1996 |
| WO | WO-96/32105 A1 | 10/1996 |
| WO | WO-96/40890 A1 | 12/1996 |
| WO | WO-96/40896 A1 | 12/1996 |
| WO | WO-97/42338 A1 | 11/1997 |
| WO | WO-98/15179 A1 | 4/1998 |
| WO | WO-98/24812 A2 | 6/1998 |
| WO | WO-98/24812 A3 | 6/1998 |
| WO | WO-98/33815 A1 | 8/1998 |
| WO | WO-98/34120 A1 | 8/1998 |
| WO | WO-98/39653 A1 | 9/1998 |
| WO | WO-98/40484 A1 | 9/1998 |
| WO | WO-98/44955 A1 | 10/1998 |
| WO | WO-98/45444 A1 | 10/1998 |
| WO | WO-98/46636 A2 | 10/1998 |
| WO | WO-98/46636 A3 | 10/1998 |
| WO | WO-99/27944 A1 | 6/1999 |
| WO | WO-99/58572 A1 | 11/1999 |
| WO | WO-99/60024 A1 | 11/1999 |
| WO | WO-00/69456 A2 | 11/2000 |
| WO | WO-00/69456 A3 | 11/2000 |
| WO | WO-00/72876 A2 | 12/2000 |
| WO | WO-00/72876 A3 | 12/2000 |
| WO | WO-00/72880 A2 | 12/2000 |
| WO | WO-00/72880 A3 | 12/2000 |
| WO | WO-00/77178 A1 | 12/2000 |
| WO | WO-01/10900 A2 | 2/2001 |
| WO | WO-01/10900 A3 | 2/2001 |
| WO | WO-01/18169 A2 | 3/2001 |
| WO | WO-01/18169 A3 | 3/2001 |
| WO | WO-01/27160 A1 | 4/2001 |
| WO | WO-01/39796 A2 | 6/2001 |
| WO | WO-01/39796 A3 | 6/2001 |
| WO | WO-01/62801 A2 | 8/2001 |
| WO | WO-01/62801 A3 | 8/2001 |
| WO | WO-01/77167 A2 | 10/2001 |
| WO | WO-01/77167 A3 | 10/2001 |
| WO | WO-01/21141 A3 | 3/2002 |
| WO | WO-02/21141 A2 | 3/2002 |
| WO | WO-02/25279 A2 | 3/2002 |
| WO | WO-O2/25279 A3 | 3/2002 |
| WO | WO-02/38177 A2 | 5/2002 |
| WO | WO-02/38177 A3 | 5/2002 |
| WO | WO-02/46237 A2 | 6/2002 |
| WO | WO-02/46237 A3 | 6/2002 |
| WO | WO-02/070647 A2 | 9/2002 |
| WO | WO-02/070647 A3 | 9/2002 |
| WO | WO-02/074240 A2 | 9/2002 |
| WO | WO-02/074240 A3 | 9/2002 |
| WO | WO-02/088306 A2 | 11/2002 |
| WO | WO-02/088306 A3 | 11/2002 |
| WO | WO-02/088307 A2 | 11/2002 |
| WO | WO-02/088307 A3 | 11/2002 |
| WO | WO-02/096937 A2 | 12/2002 |
| WO | WO-02/096937 A3 | 12/2002 |
| WO | WO-03/000714 A2 | 1/2003 |
| WO | WO-03/000714 A3 | 1/2003 |
| WO | WO-03/015691 A2 | 2/2003 |
| WO | WO-03/015691 A3 | 2/2003 |
| WO | WO-03/016467 A2 | 2/2003 |
| WO | WO-03/016467 A3 | 2/2003 |
| WO | WO-03/039467 A2 | 5/2003 |
| WO | WO-03/039467 A3 | 5/2003 |
| WO | WO-03/051374 A2 | 6/2003 |
| WO | WO-03/051374 A3 | 6/2003 |
| WO | WO-03/074081 A1 | 9/2003 |
| WO | WO-03/077858 A2 | 9/2003 |
| WO | WO-03/077858 A3 | 9/2003 |
| WO | WO-03/086310 A2 | 10/2003 |
| WO | WO-03/086310 A3 | 10/2003 |
| WO | WO-03/090772 A1 | 11/2003 |
| WO | WO-03/104437 A2 | 12/2003 |
| WO | WO-03/104437 A3 | 12/2003 |
| WO | WO-2004/001426 A2 | 12/2003 |
| WO | WO-2004/001426 A3 | 12/2003 |
| WO | WO-2004/024090 A2 | 3/2004 |
| WO | WO-2004/024770 A1 | 3/2004 |
| WO | WO-2004/029630 A1 | 4/2004 |
| WO | WO-2004/032868 A2 | 4/2004 |
| WO | WO-2004/056318 A2 | 7/2004 |
| WO | WO-2004/058184 A2 | 7/2004 |
| WO | WO-2004/067561 A1 | 8/2004 |
| WO | WO-2004/076677 A2 | 9/2004 |
| WO | WO-2004/076677 A3 | 9/2004 |
| WO | WO-2004/095031 A1 | 11/2004 |
| WO | WO-2004/098631 A1 | 11/2004 |
| WO | WO-2005/011599 A2 | 2/2005 |
| WO | WO-2005/018424 A2 | 3/2005 |
| WO | WO-2005/025516 A2 | 3/2005 |
| WO | WO-2005/025616 A1 | 3/2005 |
| WO | WO-2005/028511 A2 | 3/2005 |
| WO | WO-2006/036291 A2 | 4/2006 |
| WO | WO-2006/118959 A2 | 11/2006 |
| WO | 2008/156621 A1 | 12/2008 |

OTHER PUBLICATIONS

Al-Iazikami, B. et al. (1997). "Standard Conformations for the Canonical Structures of Immunoglobulins," *J. Molec. Biol.* 273:927-948.

Armour, K. L. et al. (1999). "Recombinant Human IgG Molecules Lacking FcK Receptor I binding and Monocyte Triggering Activities," *Eur. J. Immunol.* 29:2613-2624.

Armour, K.L. et al. (2003) "Differential Binding to Human FcγRIIa and FcγRIIb Receptors by Human IgG Wildtype and Mutant Antibodies," *Molecular Immunology* 40:585-593.

Asami-Odaka, A. et al. (2005). "Passive Immunization of the Aβ42(43) C-Terminal-Specific Antibody BC05 in a Mouse Model of Alzheimer's Disease," *Neurodegenerative Dis.* 2:36-43.

Bach, J-F. et al. (1985). "Monoclonal Antibodies as Therapeutic Tools in Medicine" Chapter 22 in *Handbook of Monoclonal Antibodies: Applications in Biology and Medicine*, Ferrone, S. et al. eds., Noges Publications: Park Ridge: NJ, pp. 419-435.

Bacskai, B. J. et al. (2001). "Imaging of Amyloid-J Deposits in Brains of Living Mice Permits Direct Observation of Clearance of Plaques with Immunotherapy," *Nature Medicine* 7(3):369-372.

Bacskai, B. J. et al. (2002). "Non -Fc-Mediated Mechanisms Are Involved in Clearance of Amyloid-J In Vivo by Immunotherapy," *J. Neurosci* 22(18):7873-7878.

Baekelandt, V. et al. (2000). "Gene Therapeutic Strategies for Neurodegenerative Diseases," *Current Opinion in Molecular Therapeutics* 2(5):540-554.

Balint, R. G. et al. (1993). "Antibody Engineering by Parsimonious Mutagenesis," *Gene* 137(1):109-118.

Bamberger, M.E. et al. (2001). "Microglial Interaction with Beta-Amyloid: Implications for the the Pathologenesis of Alzheimer's Disease," *Microscopy Research and Techniques* 54(2):59-70.

Barbas III, C.F. et al. (2001). "Vector pComb3X, Figure 2.2" In Chapter 2 In *Phage Display: A Laboratory Manual*, Cold Spring Harbor Laboratory Press: Cold Spring Harbor, NY, pp. 2.9-2.13.

Barbas, III C. F. et al. (1994) "In Vitro Evolution of a Neutralizing Human Antibody to Human Immnunodeficiency Virus Type 1 to Enhance Affinity and Broaden Strain Cross-Reactivity," *Proc. Nat. Acad. Sci USA* 91:3809-3813.

Bard, F. (2000). "Peripherally Administered Antibodies Against Amyloid β—Peptide Enter the Central Nervous System and reduce Pathology in a Mouse Model of Alzheimer Disease," *Nature Medicine* 6(8): 916-919.

Bard, F. et al. (Feb. 18, 2003). "Epitope and Isotype Specificities of Antibodies to β-Amyloid Peptide for Protection Against Alzheimer's Disease-Like Neuropathology," *Proc. Natl. Acad. Sci. USA* 100(4):2023-2028.

Berkner, K. L. (1988). "Development of Adenovius Vectors for the Expression of Heterologous Gene," *Biotechniques* 6(7):616-627.

Bird, R. E. et al. (1988). "Single-Chain Antigen-Binding Proteins," *Science* 242:423-426.

Blasko, I. et al. (2001). "Does IFN K-Play A Role in Neurodegeneration," *Journal of Neuroimmunology* 116(1):1-4.

Boemer, P. et al. (1991). "Production of Antigen-Specific Human Monoclonal Antibodies from In Vitro-Primed Human Splenocytes," *J. Immunol.* 147(1):86-95.

Boncristiano, S. et al. (2002). "Cholinergic Changes in the APP23 Transgenic Mouse Model of Cerebral Amyloidosis," *The Journal of Neuroscience* 22(8):3234-3243.

Boyd, P. N. et al. (1995). "The Effect of the Removal of Sialic Acid, Galactose and Total Carbohydrate on the Functional Activity of Campath-1H," *Mol. Immunol.* 32(17/18):1311-1318.

Brayden, D.J. et al. (2001). "Encapsulation in Biodegradable Microparticles Enhances Serum Antibody Response to Parentally-Delivered β-Amyloid in Mice," *Vaccine* 19(30):4185-4193.

Brennan, M. et al. (1985). "Preparation of Bispecific Antibodies by Chemical Recombination of Monoclonal Immunoglobulin $G_1$ Fragments," *Science* 229:81-83.

Brown, B. A. et al. (1987). "Tumor-Specific Genetically Engineered Murine/Human Chimeric Monoclonal Antibody," *Cancer Res.* 47:3577-3583.

Bugelski, P.J. et al. (2000). "Preclinical Development of Keliximab, a Primatized ™ Anti-CD4 Monoclonal Antibody, in Human CD4 Transgenic Mice: Characterization of the Model and Safety Studies," *Human & Experimental Toxicology* 19:230-243.

Bussière, T. et al. (Sep. 2004). "Animal Model: Morphological Characterization of Thioflavin-S-Positive Amyloid Plaques in Transgenic Alzheimer Mice and Effect of Passive Aβ Immunotherapy on Their Clearance," *American Journal of Pathology* 165(3):987-995.

Calhoun, M. E. et al. (1999). "Neuronal Overexpression of Mutant Amyloid Precursor Protein Results in Prominent Deposition of Cerebrovascular," *Neurobiology* 6(24):14088-14093.

Canfield, S.M. et al. (Jun. 1991). "The Binding Affinity of Human IgG for its High Affinity Fc Receptor Is Determined by Multiple Amino Acids in the $C_H2$ Domain and Is Modulated by the Hinge Region," *J. Exp. Med.* 173:1483-1491.

Capel, P. J. A. et al. (1994). "Heterogeinity of Human IgG Fc Receptors," *Immunomethods* 4:25-34.

Carter, D. B et al. (2001). "Human Apolipoprotein E4 Accelerates Beta-Amyloid Deposition in APPsw Transgenic Mouse Brain," *Annals of Neurology* 50(4):468-475.

Carter, P. et al. (1992). "High Level *Escherichia coli* Expression and Production of Bivalent Humanized Antibody Fragment," *Bio/Technology* 10:163-167.

Chartier-Harlin, M.-C. et al. (2001). "Un Espoir Thérapeutique Dans La Maladie D'Alzheimer, Ou Peut-On Traiter Le Mal Par Le Mal," *M/S Nouvelles Medicine Sciences* 17(4):523-524.

Chartier-Harlin, M.-C. et al. (2001). "A Promising Treatment for Alzheimer's Disease, or Can The Disease be Treated with the Disease?", *M/S Nouvelles Medicine Sciences* 17(4):523-524. (English Translation, three pages.).

Chauhan, N. B. et al. (2001). "Distribution of Intraventricularly Administered Antiamyloid-Beta Peptide (Aβ) Antibody in the Mouse Brain," *Journal of Neuroscience Research* 66:231-235.

Cherny, R.A. et al (2001). "Treatment with A Copper-Zinc Chelator Markedly and Rapidly Inhibits Beta-Amyloid Accumulation in Alzheimer's Disease Transgenic Mice," *Neuron* 30(3):665-676.

Chiou, H. C. et al. (1994). "In Vivo Gene Therapy via Receptor-Mediated DNA Delivery," In *Gene Therapeutics: Methods and Applications of Direct Gene Transfer*, Wolff, J. A., ed., Birkhauser, pp. 143-156.

Chishti, M.A. et al. (2001). "Early-Onset Amyloid Deposition and Cognitive Deficits in Transgenic Mice Expressing a Double Mutant Form of Amyloid Precursor Protein," *Journal of Biological Chemistry* 276(24):21562-21570.

Chothia, C. et al. (1989). "Conformations of Immunoglobulin Hypervariable Regions 395," *Nature* 342:877-883.

Chung, H.Y. et al. (2001). "Uptake of Fibrillar β-Amyloid by Microglia Isolated from MSR-A (Type I and Type II) Knockout Mice," *NeuroReport* 12(6):1151-1154.

Clackson, T. et al. (1991). "Making Antibody Fragments Using Phage Display Libraries," *Nature* 352:624-628.

Clynes, R. et al. (1998). "Fc Receptors Are Required in Passive and Active Immunity to Melanoma," *PNAS USA* 95:652-656.

Cohen, J. (1993). "Naked DNA Points Way to Vaccines," *Science* 259(5102):1691-1692.

Cole, S.P.C. et al. (1985). "The EBV-Hybridoma Technique and Its Application to Human Lung Cancer," *Monoclonal Antibodies and Cancer Therapy*, Reisfeld, R. A. et al., Alan R.Liss, Inc., pp. 77-96.

Comery, T.A. et al. (2005). "Passive Immunization Against β-Amyloid Leads to Acute Cognition Improvement," *Society for Neuroscience*, Program No. 134.5, 2005 Abstract Viewer/lntinerary Planner, Abstract, one page.

Connelly, S. et al. (1995). "In Vivo Gene Delivery and Expression of Physiological Levels of Functional Human Factor VIII in Mice," *Human Gene Therapy* 6:185-193.

Cunningham, B. C. et al. (1989). "High-Resolution Epitope Mapping of hGH-Receptor Interactions by Alanine-Scanning Mutagenesis," *Science* 244(4908):1081-1085.

Curiel, D. T. (1992). "High-Efficiency Gene Transfer Mediated by Adenovirus Coupled to DNA-Polylysine Complexes," *Hum.Gene Ther* 3:147-154.

Das, P. et al. (Sep. 17, 2003). "Amyloid-β Immunization Effectively Reduces Amyloid Deposition in FcRγ-/- Knock-Out Mice," *J. Neurosci*. 23(24):8532-8538.

Daugherty, B.L. et al. (1991). "Polymerase Chain Reaction Faciliates the Cloning, CDR-Grafting, and Rapid Expression of a Murine Monoclonal Antibody Directed Against the CD18 Component of Leukocyte Integrins," *Nucl. Acids Res.* 19(9):2471-2476.

Dayhoff, M.O. et al. (1978). "A Model of Evolutionay Change in Proteins," Chapter 22 In *Atlas of Protein Sequence and Structure*, National Biomedical Research Foundation, Washington DC vol. 5, Supplemental 3 pp. 345-352.

De la Monte, S.M. (1999). "Molecular Abnormalities of the Brain in Down Syndrome: Relevance to Alzheimer's Neurodegeneration" In *J. Neural Transm. Suppl*., Lubec, G. eds., Springer-Verlag Wien: New York, NY 57:1-19.

De Strooper, B. et al. (2001). "Alzheimer's Disease: An Inflammatory Drug Prospect," *Nature* 414:159-160.

DeHaas, M. et al. (1995). "FCK Receptors of Phagocytes," *J. Lab. Clin. Med*.126(4):330-341.

Deininger, M.H. et al. (Dec. 15, 2002). "Aberrant Neuronal and Paracellular Deposition of Endostatin in Brains of Patients with Alzheimer's Disease," *J. Neurosci*. 22(24):10621-10626.

De Lustig, E.S. et al. (1994). "Peripheral Markers and Diagnostic Criteria in Alzheimer's Disease: Critical Evaluations," *Rev. Neurosciences* 5(3):213-225.

DeMattos, R. B. (2001). "Peripheral Anti-Aβ Antibody Alters CNS and Plasma Aβ Burden in a Mouse Model of Alzheimer's Disease," PNAS 98(15):8850-8855.

DeMattos, R. B. et al. (2002). "Brain to Plasma Amyloid-β Efflux: a Measure of Brain Amyloid Burden in a Mouse Model of Alzheimer's Disease," *Science* 295:2264-2267.

Dodart, J.-C. et al. (2002). "Immunization Reverses Memory Deficits Without Reducing Brain Aβ Burden in Alzheimer's Disease Model," *Nat. Neuroscience* 5(5):452-457.

Donofrio, G. et al. (Jul. 2005). "Paracrine Inhibition of Prion Propagation by Anti-PrP Single-Chain Fv Miniantibodies," *J. Virol.* 79(13):8330-8338.

Duff, K. (1999). "Curing Amyloidosis: Will it Works in Humans," *Trends in Neurosciences* 22(11):485-486.

Duff, K. et al. (2001). "Progress in the Modeling of Neurodegenerative Diseases in Transgenic Mice," *Current Opinion in Neurology* 14(4):441-447.

Duncan, A.R. et al. (Apr. 21, 1988). "The Binding Site for C1q on IgG," *Nature* 332:738-740.

El-Agnaf, O.M.A et al. (2001). "Non-Fibrillar Oligomeric Species of the Amyloid ABri Peptide, Implicated in Familial British Dementia, Are More Potent at Inducing Apoptotic Cell Death than Protofibrils or Mature Fibrils," *Journal of Molecular Biology* 310(1):157-168.

Eppstein, D. A. et al. (1985). "Biological Activity of Liposome-Encapsulated Murine Interferon K is Mediated by a Cell Membrane Receptor," *PNAS USA* 82:3688-3692.

Esiri, M. (2001). "Is an Effective Immune Intervention for Alzheimer's Disease in Prospect?" *Trends in Pharmacological Sciences* 22(1):2-3.

Fassbender, K. (2001). "Alzheimer's Disease: Molecular Concepts and Therapeutic Targets," *Naturwissenschaften* 88:261-267.

Ferrer, I. et al. (Jan. 2004). "Neuropathology and Pathogenesis of Encephalitis Following Amyloid-β Immunization in Alzheimer's Disease," *Brain Pathol.* 14(1):11-20.

Findeis, M. A. et al. (1993). "Targeted Delivery of DNA for Gene Therapy via Receptors," *TibTech* 11:202-205.

Fisher-Hoch, S. P. et al. (1989). "Protection of Rhesus Monkeys from Fatal Lassa Fever by Vaccination with A Recombinant Vaccina Virus Containing the Lassa Virus Glycoprotein Gene," *PNAS USA* 86:317-321.

Fishman, C.E. et al. (2001). "Statistical Aspects of Quantitative Image Analysis of J-Amyloid in the $APP^{V717F}$ Transgenic Mouse Model Alzheimer's Disease," *Journal of Neuroscience Methods* 108(2):145-152.

Flexner, C. et al (1990). "Attenuation and Immunogenicity in Primates of Vaccinia Virus Recombinants Expressing Human Interleukin-2," *Vaccine* 8:17-21.

Frenkel, D. et al. (2000). "Immunization Against Alzheimers' J-Amyloid Plaques via EFRH Phage Administration," *PNAS* 97(21):11455-11459.

Friend, P.J. et al. (Dec. 15, 1999). "Phase I Study of an Engineered Aglycosylated Humanized CD3 Antibody in Renal Transplant Rejection," *Transplantation* 68(11):1632-1637.

Fukuta, T. (2001). "Difference in Toxicity of J-Amyloid Peptide with Aging in Relation to Nerve Growth Factor Content in Rat Brain," *Journal of Neural Transmission* 108(2):221-230.

Galasko, D. (2001). "New Approaches to Diagnose and Treat Alzheimer's Disease—A Glimpse of the Future," *Clinic in Geriatric Medicine* 17(2):393-410.

Garcia, P. et al. (1986). "Nucleotide Sequence and Expression of the Pneumococcal Autolysin Gene from Its Own Promoter in *Escherichia coli*," *Gene* 43:265-272.

Gaskin, F. et al. (Apr. 1993). "Human Antibodies Reactive with β-Amyloid Protein in Alzheimer's Disease," *J. Exp. Med.* 177:1181-1186.

Gazzano-Santoro, H. et al. (1997). "A Non-Radioactive Complement-Dependent Cytotoxicity Assay for Anti-CD20 Monoclonal Antibody," *J. Immunol. Methods* 202:163-171.

Geerligs, H. et al. (1989). "The Influence of Different Adjuvants on the Immune Response to a Synthetic Peptide Comprising Amino Acid Residues 9-21 of Herpes simplex Virus Type 1 Glycoprotein D," *J. Immunol. Methods* 124(1):95-102.

Gelman, B.B. et al. (2004). "Brain Aging in Acquired Immunodeficiency Syndrome: Increased Ubiquitin-Protein Conjugate is Correlated with Decreased Synaptic Protein but not Amyloid Plaque Accumulation," *J. Neurovirol.* 10(2):98-108.

Genbank Accession No. CAA09181, created Dec. 2, 1998, located at <http://www.ncbi.nlm.nih.gov/entrez/viewer.fcgi?db=protein&val=3954885>, last visited Oct. 19, 2005, two pages.

Genbank Accession No. P01859, created Jul. 21, 1986, located at <http://www.ncbi.nlm.nih.gov/entrez/viewer.fcgi?db=protein&val=121043>, last visited Oct. 19, 2005, four pages.

Ghetti, B. et al. (2003). "Hereditary Prion Protein Amyloidoses," *Clin. Lab. Med.* 23(1):65-85.

Goding, J.W. (1983). "Production of Monoclonal Antibodies" Chapter 3 In *Monoclonal Antibodies: Principles and Practice* Academic Press, Inc.:New York, NY, pp. 56-97.

Gordon, M.N. et al. (2001). "Correlation Between Cognitive Deficits and Aβ Deposits in Transgenic APP+PS1 Mice," *Neurobiol. Aging* 22:377-385.

Gordon, M.N. et al. (2002). "Time Course of the Development of Alzheimer-like Pathology in the Doubly Transgenic PS1+APP Mouse," *Exp. Neurol.* 173:183-195.

Green, D.A. et al. (2005). "Brain Deposition of Beta-Amyloid is a Common Pathologic Feature in HIV Positive Patients," *AIDS* 19(4):407-411.

Gregory, G.C. et al. (2005). "What is the Dominant Aβ Species in Human Brain Tissue?" *Neurotoxicity Research* 7(1,2):29-41.

Griffiths, A. D. et al. (1993). "Human Anti-Self Antibodies with High Specificity from Phage Display Libraries," *EMBO J.* 12(2):725-734.

Guyer, R. L. et al. (1976). "Immunologlobulin Binding by Mouse Intestinal Epithelial Cell Receptors," *J. Immunol.* 117(2):587-593.

Guzman, R. J. et al. (1993). "Efficient and Selective Adenovirus-Mediated Gene Transfer ltno Vascular Neointima," *Circulation* 88(6):2838-2848.

Guzman, R. J. et al. (1993). "Efficient Gene Transfer Into Myocardium by Direct Injection of Adenovirus Vectors," *Cir. Res.* 73(6):1202-1207.

Haass, C. (2002). "New Hope for Alzheimer Disease Vaccine," *Nature Medicine* 8(11):1195-1196.

Hadland, B.K. et al. (2001). "K-Secretase Inhibitors Repress Thymocyte Development," *PNAS USA* 98(13):7487-7491.

Hammarström, P. et al. (2003). "D18G Transthyretin is Monomeric, Aggregation Prone, and Not Detectable in Plasma and Cerebrospinal Fluid: A Prescription for Central Nervous System Amyloidosis?" *Biochemistry* 42(22):6656-6663.

Hardy, J. (1996). "New Insights Into the Genetics of Alzheimer's Disease," *Ann. Med.* 28:255-258.

Hardy, J. (1997). "Amyloid, the Presenilins and Alzheimer's Disease," *Trends Neurosci.* 20(4):154-159.

Harrington, C.R. et al. (Oct. 3, 1993). "Characterization of an Epitope Specific to the Neuron Specific Isoform of Human Ecolase Recognised by a Monoclonal Antibody Raised Against a Synthetic Peptide Corresponding to the C-Terminus of Beta/A4 Protein," *Biochimica et Biophysica Acta* 1158(2):120-128.

Hawkins, R. E. et al. (1992). "Selection of Phage Antibodies by Binding Affinity Mimicking Affinity Maturation," *J. Mol. Biol.* 226:889-896.

Hein, J. (1990). "Unified Approach to Alignment and Phylogenies" Chapter 39 In *Methods of Enzymology*, Academic Press, Inc., vol. 183 pp. 626-645.

Hezareh, M. et al. (Dec. 2001). "Effector Function Activities of a Panel of Mutants of a Broadly Neutralizing Antibody Against Human Immunodeficiency Virus Type 1," *J. Virol.* 75(24):12161-12168.

Higgins, D. G et al. (1989). "Fast and Sensitive Multiple Sequence Alignments on a Microcomputer," *CABIOS Communications* 5(2):151-153.

Hock, C. et al. (2002). "Generation of Antibodies Specific for J-Amyloid by Vaccination of Patients with Alzheimer Disease," *Nature Medicine* 8(11):1270-1275.

Holcomb, L. A. et al. (1999). "Behavioral Changes in Transgenic Mice Expressing both amyloid Precursor Protein and Presenilin-1 Mutations: Lack of Assocaition with Amyloid Deposits," *Behav. Gen.* 29(3):177-185.

Holcomb, L.A et al. (1998). "Accelerated Alzheimer-Type Phenotype in Transgenic Mice Carrying bot Mutant *Amyloid Precursor Protein* and *Presinilin* 1 Transgenes," *Nat. Med.* 4(1):97-100.

Holliger, P. et al. (1993). "'Diabodies': Small Bivalent and Bispecific Antibody Fragments," *PNAS* 90:6444-6448.

Holt, L.J. et al. (Nov. 2003). "Domain Antibodies: Proteins for Therapy," *Trends in Biotechnology* 21(11):484-489.

Hoogenboom, H. R. et al. (1992). "By-Passing Immunisation Human Antibodies from Synthetic Repertoires of Germline $V_H$ Gene Segments Rearranged in Vitro," *J. Mol. Biol.* 227:381-388.

Hoozemans, J.J.M. et al. (2001). "Immunological Aspects of Alzheimer's Disease-Therapeutic Implication," *BioDrugs* 15(5):325-337.

Hsiao, K. et al. (1996). "Correlative Memory Deficits, AJ Elevation, and Amyloid Plaquest in Transgenic Mice," *Science* 274:99-102.

Hsu, T.-A. et al. (1997). "Differential N-Glycan Patterns of Secreted and Intracellular IgG Produced in *Triphoplusia ni* Cells," *J. Biol. Chem.* 272(14):9062-9070.

Huse, J.T. et al. (2000). "Closing in on the Amyloid Cascade Recent Insights Into the Cell Biology of Alzheimer's Disease," *Molecular Neurobiology* 22(1-3):81-98.

Hwang, K. J. et al. (1980). "Hepatic Uptake and Degradation of Unilmellar Sphingomyelin/Cholesterol Liposomes: A Kinetic Study," *Proc. Natl Acad. Sci USA* 77(7):4030-4034.

Idusogie, E.E. et al. (2000). "Mapping of the C1q Binding Site on Rituxan, a Chimeric Antibody with a Human IgG1 Fc," *J. Immunology* 164:4178-4184.

Illiades, P. et al. (1997). "Triabodies: Single Chain Fv Fragments Without a Linker Form Trivalent Trimers," *FEBS Letters* 409:437-441.

International Search Report mailed May 3, 2006, for PCT Application No. PCT/US03/32080 filed Oct. 9, 2003, four pages.

International Search Report mailed May 11, 2006, for PCT Application No. PCT/US2005/027295 filed Aug. 1, 2005, six pages.

Irizarry, M. C. et al. (2001). "Alzheimer Disease Therapeutics," *Journal of Neuropathology and Experimental Neurology* 60(10):923-928.

Jackson, J. R. et al. (1995). "In Vitro Antibody Maturation," *J. Immunol.* 154(7):3310-3319.

Janus, C. et al. (2000). "Aβ Peptide Immunization Reduces Behavioural Impairment and Plaques in a Model of Alzheimer's Disease," *Nature* 408:979-982.

Janus, C. et al. (2001). "Transgenic Mouse Models of Alzheimer's Disease," *Physiology & Behavior* 73(5):873-886.

Jefferis R. et al. (1997). "Glycosylation of Antiody Molecules: Structural and Functional Significance," *Chem. Immunol.* 65:111-128.

Jefferis, R. et al. (1998). "IgG-Fc-Mediated Effector Functions: Molecular Definition of Interaction Sites for Effector Ligands and the Role of Glycosylation," *Immunological Reviews* 163:59-76.

Jhee, S. et al. (2001). "J-Amyloid Therapies in Alzheimer's Disease," *Expert Opinion on Investigational Drugs* 10(4):593-605.

Jin, K. et al. (2004). "Familial Leptomeningeal Amyloidosis with a Transthyretin Variant Asp18Gly Representing Repeated Subarachnoid Haemorrhages with Superficial Siderosis," *J. Neurol. Neurosurg. Psychiatry* 75(10):1463-1466.

Johnson, J.P. et al. (1985). "Monoclonal Antibodies and Melanomas" Chapter 18 In *Handbook of Monoclonal Antibodies: Applications in Biology and Medicine*, Ferrone, S. et al. eds., Noges Publications: Park Ridge: NJ, pp. 347-359.

Johnson, K. S. et al. (1993). "Human Antibody Engineering," *Current Opinion in Structural Biology* 3:564-571.

Jolly, D. (1994). "Viral Vector Systems for Gene Therapy," *Cancer Gene Therapy* 1(1):51-64.

Jones, P. T. et al. (1986). "Replacing the Complementarity-Determining Regions in a Human Antibody with Those from a Mouse," *Nature* 321:522-525.

Kabat, E. A. et al. (1991). "Tabulation and Analysis of Amino Acid and Nucleic Acid Sequences of Precursors, V-Regions, C-Regions, J-Chain, T-Cell Receptor for Antigen, T-Cell Surface Antigens, $J_2$-Microglobulins, Major Histocompatibility Antigens, Thy-1, Complement, C-Reactive Protein, Thymopoietin, Integrins, Post-gamma Globulin, $I_2$-Macroglobulins, and Other Related Proteins," In *Sequences of Proteins of Immunological Interest*, US Dept. of Health and Human Services NIH Publication No. 91-3242, Fifth Edition(Table of Contents only).

Kabawat, S.E. et al. (1985). "Monoclonal Antibodies in Diagnostic Pathology" Chapter 16 In *Handbook of Monoclonal Antibodies: Applications in Biology and Medicine*, Ferrone, S. et al. eds., Noges Publications: Park Ridge: NJ, pp. 293-328.

Kahle, P.J. et al. (2002). "Hyperphosphorylation and Insolubility of α-Synuclein in Transgenic Mouse Oligodendrocytes," *EMBO Reports* 3(6):583-588.

Kakimura, J. (2001). "BiP/GRP78-Induced Production of Cytokines and Uptake of Amyloid-J(1-42 Peptide in Microglia," *Biochemical and Biophysical Research Communications* 281(1):6-10.

Kaplitt, M. G. et al. (1994). "Long-Term Gene Expression and Phenotypic Correction Using Adeno-Associated Virus Vectors in the Mammalian Brain," *Nature Genetics* 8:148-153.

Karlsson, R. et al. (1994). "Kinetic and Concentration Analysis Using BIA Technology," *Methods: A Companion to Methods in Enzymology* 6:99-110.

Kenney, J. S. et al. (1989). "Influence of Adjuvants on the Quantity, Affinity, Isotype and Epitope Specificity of Murine Antibodies," *J. Immunol. Methods* 121(1):157-166.

Kim, J-K. et al. (1994). "Localization of the Site of the Murine IgG1 Molecule that is Involved in Binding to the Murine Intestinal Fc Receptor," *J. Immunol.* 24:2429-2434.

Kimura, O. et al. (1994). "Retroviral Delivery of DNA Into the Livers of Transgenic Mice Bearing Premalignant and Malignant Hepatocellular Carcinomas," *Human Gene Therapy* 5(7):845-852.

Klein, W.L. et al. (2001). "Targeting Small A Beta Oligomers: the Solution to an Alzheimers' Disease Conundrum," *Trends in Neurosciences* 24(4):219-224.

Klyubin, I. et al. (May 2005). "Amyloid β Protein Immunotherapy Neutralizes Aβ Oligomers That Disrupt Synaptic Plasticity in vivo," *Nature Medicine* 11(5):556-561.

Kohler, G. et al. (1975). "Continuous Cultures of Fused Cells Secreting Antibody of Predefined Specificity," *Nature* 256:495-497.

Kolls, J. et al. (1994). "Prolonged and Effective Blockade of Tumor Necrosis Factor Activity Though Adenovirus-Mediated Gene Transfer," *PNAS USA* 91:215-219.

Kortt, A. A. et al. (1997). "Single-Chain Fv Fragments of Anti-Neuraminidase Antibody NC10 Containing Five- and Ten-Residue Linkers Form Dimers and With Zero-Residue Linker a Trimer," *Protein Engineering* 10(4):423-433.

Kotilinek, L.A. et al. (2002). "Reversible Memory Loss in a Mouse Transgenic Model of Alzheimer's Disease," *J. Neurosci* 22(15):6331-6335.

Kril, J. J. (2001). "Alzheimer's Disease: It's Diagnosis and Pathogenesis," In *International Review of Neurobiology*, Bradley, R. J. et al., eds., Academic Press, Inc., vol. 48, pp. 167-217.

Lee, V.M.Y. (2001). "A Beta Immunization: Moving A Beta Peptide from Brain to Blood," *PNAS* 98(16):8931-8932.

Levites, Y. et al. (Jan. 2006). "Anti-$β_{42}$- and Anti-$β_{40}$-Specific mAbs Attenuate Amyloid Deposition in an Alzheimer Disease Mouse Model," *The Journal of Clinical Investigation*, 116(1):193-201.

Lin, Y. M. (2001). "Amyloid Fibril Formation in Microwell Plates for Screening of Inhibitors," *Amyloid-Journal of Protein Folding Disorders* 8(3):183-193.

Lobuglio, A. F. et al. (1989). "Mouse/Human Chimeric Monoclonal Antibody in Man: Kinetics and Immune Response," *PNAS USA* 86:4420-4224.

Lossos, A. et al. (2005). "Extended Phenotype in the Transthyretin Tyr77 Familial Amyloid Polyneuropathy," *Eur. Neurol.* 53(2):55-59.

Lund, J. et al. (1996). "Multiple Interactions of IgG with Its Core Oligosaccharide Can Modulate Recognition by Complement and Human Fcγ Receptor I and Influence the Synthesis of Its Oligosaccharide Chains," *J. Immunology* 157:4963-4969.

Maimone, D. et al. (2001). "Pharmacogenomics of Neurdegenerative Diseases," *European Journal of Phamacology* 413(1):11-29.

Maratea, D. et al. (1985). "Deletion and Fusion Analysis of the Phage >X174 Lysis Gene E," *Gene* 40:39-46.

Marks, J. D. et al. (1991). "By-Passing Immunization Human Antibodies from V-Gene Libraries Displayed on Phage," *J. Mol. Biol.* 222:581-597.

Marks, J.D. et al. (1992). "By-Passing Immunization: Building High Affinity Human Antibodies by Chain Shuffling," *Bio/Technology* 10:779-783.

Martin, F. J. et al. (1982). "Irreversible Coupling of Immunoglobulin Fragments to Preformed Vesicles," *J. Biol. Chem.* 257(1):286-288.

McCafferty, J. et al. (1990). "Phage Antibodies: Filamentous Phage Displaying Antibody Variable Domains," *Nature* 348:552-554.

McGowan, E. (1999). "Amyloid Phenotype Characterization of Transgenic Mice Overexpressing both Mutant Amyloid Precursor Protein and Mutant Presenilin 1 Transgenes," *Neurobiology of Disease* 6:231-244.

McLaurin, J. et al. (2002). "Therapeutically Effective Antibodies Against Amyloid-J Peptide Target Amyloid-J Residues 4-10 and Inhibit Cytotoxicity and Fibrillogenesis," *Nature Medicine* 8(11):1263-1269.

Merrifield, R. B. (1963). "Solid Phase Peptide Synthesis: I. the Synthesis of a Tetrapeptide," *J. Am. Chem. Soc.* 85:2149-2146.

Milstein, C. et al. (1983). "Hybrid Hybridomas and Their Use Immunohistochemistry," *Nature* 305:537-539.

Mitrasinovic, O.M. et al. (2001). "Overexpression of Macrophage Colony-Stimulating Factor Receptor on Microglial Cells Induces an Inflammatory Response," *Journal of Biological Chemistry* 276(32):30142-30149.

Mohajeri, M. H. et al. (2002). "Passive Immunization Against J-Amyloid Peptide Protects Central Nervous System (CNS) Neurons from Increased Vulnerability Associated with an Alzheimer's Disease Mutation," *The Journal of Biological Chemistry* 277(36):33012-33017.

Mohajeri, M.H. et al. (2004). "Assessment of the Bioactivity of Antibodies Against β-Amyloid Peptide in vitro and in vivo," *Neurodegenerative Dis.* 1:160-167.

Morgan, A. et al. (Oct. 1995). "The N-Terminal End of the $C_H2$ Domain of Chimeric Human IgG1 Anti-HLA-DR is Necessary for C1q, FcγRI and FcγRIII Binding," *Immunology* 86(2):319-324.

Morgan, D et al. (2000). "AJ Peptide Vaccination Prevents Memory Loss in an Animal Model of Alzheimer's Disease," *Nature* 408:982-985.

Morimoto, K. et al. (1992). "Single-Step Purification of F(ab')₂ Fragments of Mouse Monoclonal Antibodies (Immunoglobins G1) by Hydrophobic Interaction High Performance Liquid Chromatography Using TSKgel Phenyl-5PW," In *Journal of Biochemical and Biophysical Methods*, Chignell, C.F. et al., eds., Elsevier Science Publishers, B.V. vol. 24 pp. 107-117.

Moss, B. et al. (1989). "Vaccinia Virus Expression Vectors," *Annals of the New York Academy of Sciences: Biomedical Science and the Third World* 569:86-103.

Mullis, K.B. et al., eds. (1994). *The Polymerase Chain Reaction*, Birkäuser Press, pp. xv-xvii, (Table of Contents Only).

Münch, G. et al. (2002). "Potentional Neurotoxic Inflammatory Responses to AβVaccination in Humans," *J. Neural. Trans.* 109(7/8):1081-1087.

Murphy, C.L. et al. (2001). "Chemical Typing of Amyloid Protein Contained in Formalin-Fixed Paraffin-Embedded Biopsy Specimens," *American Journal of Clinical Pathology* 116(1):135-142.

Murphy, J. R. et al (1986). "Genetic Construction, Expression, and Melanoma-Selective Cytotoxicity of a Diphtheria Toxin-Related I-Melanocyte-Stimulating Hormone Fusion Protein," *PNAS USA* 83:8258-8262.

Myers, E.W. et al. (1988). "Optimal Alignments Linear Space," *CABIOS* 4(1):11-17.

Nanus, D.M. et al. (Dec. 2003). "Clinical Use of Monoclonal Antibody HuJ591 Therapy: Targeting Prostate Specific Membrane Antigen," *J. Urology* 170:S84-S89.

Nilsson, M. et al. (Jun. 4, 2004). "Prevention of Domain Swapping Inhibits Dimerization and Amyloid Fibril Formation of Cystatin C," *J. Biol. Chem.* 279(23):24236-24245.

Nunan, J. et al. (2001). "The C-Terminal Fragment of the Alzheimer's Disease Amyloid Protein Precursor is Degraded by Proteasome-Dependent Mechanism Distinct from Gamma-Secretase," *European Journal of Biochemistry* 268(20):5329-5336.

Omidfar, K. et al. (2004). "Production of a Novel Camel Single-Domain Antibody Specific for the Type III Mutuant EGFR," *Tumour Biol.* 25:296-305.

Orgogozo, J-M. et al. (Jul. 8, 2003). "Subacute Meningoencephalitis in a Subset of Patients with AD after Aβ42 Immunization," *Neurology* 61(1):46-54.

Ortega, S. et al. (1992). "Single-Step Purification on Deae-Sephacel of Recombinant Polypeptides Produced in *Escherichia coli*, " *Biotechnology* 10:795-798.

Pfeifer, M. et al. (2002). "Cerebral Hemorrhage After Passive Anti-AJ Immunotherapy," *Science* 298:1379.

Philip, R. et al. (1994). "Efficient and Sustained Gene Expression in Primary T. Lymphocytes and Primary and Cultured Tumor," *Mol. Cell. Biol.* 14(4):2411-2418.

Poljak, R. et al. (1994). "Production and Structure of Diabodies," *Structure* 2:1121-1123.

Price, D.L. et al. (Jul. 1993). "Alzheimer Disease and the Prion Disorders Amyloid β-Protein and Prion Protein Amyloidoses," *Proc. Natl. Acad. Sci. USA* 90:6381-6384.

Quadt, R. et al. (1993). "Characterization of a Host Protein Associated with Brome Mosaic Virus RNA-Dependent RNA Polymerase," *PNAS USA* 90:1498-1502.

Racke, M.M. et al. (Jan. 19, 2005). "Exacerbation of Cerebral Amyloid Angiopathy-Associated Microhemorrhage in Amyloid Precursor Protein Transgenic Mice by Immunotherapy Is Dependent on Antibody Recognition of Deposited Forms of Amyloid β," *J. Neurosci.* 25(3):629-636.

Ravetch, J. V. et al. (1991). "Fc Receptors," In *Annual Review of Immunology*, Paul, W. E. et al. , eds., Annual Reviews, Inc. Palo Alto, California, vol. 9 pp. 457-492. (Includes Table of Contents).

Rebe, S. et al. (Sep./Oct. 2005). "Deglycosylation of Anti-β Amyloid Antibodies Inhibits Microglia Activation in BV-2 Cellular Model," *American Journal of Alzheimer's Disease and Other Dementias* 20(5):303-313.

Reddy, M.P. et al. (2000). "Elimination of Fc Receptor-Dependent Effector Functions of a Modified IgG4 Monoclonal Antibody to Human CD4," *J. Immunology* 164:1925-1933.

Redpath, S. et al. (1998). "The Influence of the Hinge Region Length in Binding of Human IgG to Human Fcγ Receptors," *Human Immunology* 59:720-727.

Riechmann, L. et al. (1988). "Reshaping Human Antibodies for Therapy," *Nature* 332:323-327.

Robinson, E. D. (1971). "Comparison of Labeled Trees with Valency Three," *Comb. Theor.* 11:105-119.

Rolland, A. P. (1998). "From Genes to Gene Medicines: Recent Advances in Nonviral Gene Delivery," *Crit. Rev. Therap Drug Systems* 15(2):143-198.

Rosenfeld, M. A. et al. (1991). "Adenovirus-Mediated Transfer of a Recombinant II-Antitypsin Gene to the Lung Epithelium in Vivo," *Science* 252(5004):431-434.

Saido, T.C. et al. (May 27, 1994). "Spatial Resolution on the Primary β-Amyloidogenic Process Induced in Postischemic Hippocampus," *J. Bio. Chem.* 269(21):15253-15257.

Saitou, N. et al. (1987). "The Neighbor-Joining Method: A New Method for Reconstructing Phylogenetic Tree," *Mol. Biol. Evol.* 4(4):406-425.

Schenk, D. (2002). "Amyloid-β Immunotherapy for Alzheimer's Disease: the End of the Beginning," *Nature* 3:824-828.

Schenk, D. et al. (1999). "Immunization with Amyloid-β Attenuates Alzheimer Disease-Like Pathology in the PDAPP Mouse," *Nature* 400:173-177.

Schenk, D.B et al. (2000). "β-Peptide Immunization—A Possible New Treatment for Alzheimer Disease," *Archives of Neurology* 57(7):934-936.

Schier, R. et al. (1995). "Identification of Functional and Structural Amino-Acid Residues by Parsimonious Mutagenesis," *Gene* 169:147-155.

Schultz, D.R. (1985). "Monoclonal Antibodies and Detection of Malignancies" Chapter 17 In *Handbook of Monoclonal Antibodies: Applications in Biology and Medicine*, Ferrone, S. et al. eds., Noges Publications: Park Ridge: NJ, pp. 329-346.

Schwartz, R. M. et al. (1978). "Matrices for Detecting Distant Relationships," Chapter 23 In *Atlas of Protein Sequence and Structure*, Library of Congress Card Catalogue No. 65-29342, ISBN 0-912466-07-03, National Biomedical Research Foundation: Maryland, vol. 5, Supplement 3 pp. 353-358.

Selkoe, D. J. (2001). "Presenilin Notch, and the Genesis and Treatment of Alzheimer's Disease," *PNAS USA* 98(20):11039-11041.

Severino, K. A. et al. (1988). "Biosynthesis of Thyrotropinreleasing Hormone by a Rat Medullary Thyroid Carcinoma Cell Line," *J. Biol. Chem.* 263(2):620-623.

Shaw, D. R. et al. (1987). "Characterization of a Mouse/Human Chimiric Monoclonal Antibody (17-A) to a Colon Cancer Turmor-Associated Antigen," *J. Immunology* 138(12):4534-4538.

Sheets, M. D. et al. (1998). "Efficient Construction of a Large Nonimmune Phage Antibody Library: The Production of High-Affinity Human Single-Chain Antibodies to Protein Antigens," *PNAS USA* 95:6157-6162.

Smith, D.H. et al. (May 2003). "Amyloid β Accumulation in Axons After Traumatic Brain Injury in Humans," *J. Neurosurg.* 98(5):1072-1077.

Smith, T. W. et al. (1977). "Cardiac Glycoside-Specific Antibodies in the Treatment of Digitalis Intoxication," In *Antibodies in Human Diagnosis and Therapy*, Haber et al., eds, Raven Press, New York, pp. 365-389.

Sneath, P. H. A. et al., eds. (1973). *Numerical Taxonomy the Principles and Practice of Numerical Classification*, Freeman Press, San Francisco, pp. vi-ix (Table of Contents Only.).

Solomon, B. et al (1996). "Monoclonal Antibodies Inhibit in vitro Fibrillar Aggregation of the Alzheimer J-Amaloid Peptide," *Proc. National Acad. Sci* 93:452-455.

Solomon, B. et al. (1997). "Disaggregation of Alzheimer J-amyloid by Site-Directed mAb," *PNAS* 94:4109-4112.

Song, X. et al. (Sep. 2002). "Fcγ Receptor I- and III-Mediated Macrophage Inflammatory Protein 1α Induction in Primary Human and Murine Microglia," *Infection and Immunity* 70(9):5177-5184.

Spillantini, M.G. et al. (May 1990). "Different Configurational States of β-Amyloid and Their Distributions Relative to Plaques and Tangles in Alzheimer Disease," *Proc. Natl. Acad. Sci. USA* 87:3947-3951.

Stalder, M. et al. (2001). "3D-Reconstruction of Microglia and Amyloid in APP23 Transgenic Mice: No Evidence of Intracellular Amyloid," *Neurobiology of Aging* 22(3):427-434.

Steiner, H. et al. (2000). "Intramembrane Proteolysis by Presenillins," *Nature Reviews Molecular Cell Biology* 1(3):217-224.

Stoute, J.A. et al. (1997). "A Preliminary Evaluation of a Recombinant Circumsporozoite Protein Vaccine Against Plasmodium Faliciparum Malaria," *New Engl. J. Med.* 336(2):86-91.

Sturchler-Pierrat, C. et al. (1997). "Two Amyloid Precursor Protein Transgenic Mouse Models with Alzheimer Disease-Like Pathology," *PNAS USA* 94:13287-13292.

Sugarman, M.C. et al. (Apr. 30, 2002). "Inclusion Body Myositis-Like Phenotype Induced by Transgenic Overexpression of βAPP in Skeletal Muscle," *Proc. Natl. Acad. Sci. USA* 99(9):6334-6339:.

Suresh, M. R. et al. (1986). "Bispecific Monoclonal Antibodies from Hybrid Hybridomas," Chapter 17 In *Methods in Enzymology* vol. 121 pp. 211-229.

Tabatabai, G. et al. (Mar. 2005). "Primary Amyloidoma of the Brain Parenchyma," *Arch. Neurol.* 62(3):477-480.

Tanzi, R. E. et al. (1996). "The Gene Defects Responsible for Familial Suzanne Y. Guenette, and Wilma Wasco," *Neurobiol. Dis.* 3:159-168.

Tao, M-H. et al. (Oct. 15, 1989). "Studies of Aglycosylated Chimeric Mouse-Human IgG: Role of Carbohydrate in the Structure and Effector Functions Mediated by the Human IgG Constant Region," *J. Immunology* 143(8):2595-2601.

Town, T. et al. (2001). "Characterization of Murine Immunoglobulin G Antibodies Against Human Amyloid-β-42," *Neuroscience Letters* 307:101-104.

Trojanowski, J.Q. et al. (2003). "Parkinson's Disease and Related α-Synucleinopathies Are Brain Amyloidoses," *Ann. N.Y. Acad. Sci.* 991:107-110.

Turner, R. S. (2001). "Alzheimer's Disease in Man and Transgenic Mice—Females at Higher Risk," Article No. 0016 *American Journal of Pathology* 158(3):797-801.

Ulmer, J. B. et al. (1993). "Heterologous Protection Against Influenza by Injection of DNA Encoding a Viral Protein," *Science* 259:1745-1749.

Umana , P. et al. (1999). "Engineered Glycoforms of an Antieuroblastorama IgG1 with Optimized Antibody-Dependent Cellular Cytotoxic Activity," *Nature Biotech* 17:176-180.

Vaughan, T. J. et al. (1996). "Human Antibodies with Sub-Nanomolar Affinities Isolated from a Large Non-Immunized Phage Display Library," *Nature Biotechnology* 14:309-314.

Vehmas, A.K. et al. (2001). "β-Amyloid Peptide Vaccination Results in Marked Changes in Serum and Brain Aβ Levels in APPswe/ PS1AE9 Mice, as Detected by SELDI-TOF-Based ProteinChip® Technology," *DNA and Cell Biology* 20(11):713-721.

Verhoeyen, M. et al. (1988). "Reshaping Human Antibodies: Grafting and Antilysozyme Activity," *Science* 239:1534-1536.

Vickers, J.C. (2002). "A Vaccine Against Alzheimer's Disease," *Drugs & Aging* 19(7):487-494.

Walker, L.C et al. (2000). "The Cerebral Proteopahties—Neurodegenerative disorders of Protein Conformation and Assembly," *Molecular Neurobiology* 21(1-2):83-95.

Walker, L.C. et al. (Jul. 1994). "Labeling of Cerebral Amyloid in Vivo with a Monoclonal Antibody," *Journal of Neuropathology and Experimental Neurology* 53(4):377-383.

Waterhouse, P. et al. (1993). "Combinatorial Infection and In-Vivo Recombination: A Strategy for Making Large Phage Antibody Repertoires," *Nucl. Acids Res.* 21(9):2265-2266.

Weggen, S. et al. (2001). "A Subset of NSAIDs Lower Amyloidogenic Aβ42 Independently of Cyclooxygenase Activity," *Nature* 414:212-216.

Weninger, S.C. et al. (2001). "Inflammation and Alzheimer Disease: the Good, the Bad, and the Ugly," *Nature Medicine* 7(5):527-528.

Wicher, K. et al. (1989). "Immunogenicity of Three Recombinant *Treponema pallidum* Antigens Examined in Guinea Pigs," *Int. Arch. Allergy Appl. Immunol.* 89:128-135.

Wilbur, W. J. et al. (1983). "Rapid Similarity Searches of Nucleic Acid and Protein Data Banks," *PNAS USA* 80:726-730.

Wilcock, D. M. et al. (2001). "Number of AJ Inoculations in APP+PS1 Transgenic Mice Influences Antibody Titers, Microglial Activation, and Congophilic Plaque Levels," *DNA and Cell Biology* 20(11):731-736.

Wilcock, D.M. et al. (2004), "Passive Immunotherapy Against Aβ in Aged APP-Transgenic Mice Reverses Cognitive Deficits and Depletes Parenchymal Amyloid Deposits in Spite of Increased Vascular Amyloid and Microhemorrhage," *Journal of Neuroinflammation* 1:1-11.

Wilcock, D.M. et al. (Jul. 7, 2004). "Passive Amyloid Immunotherapy Clears Amyloid and Transiently Activates Microglia in a Transgenic Mouse Model of Amyloid Deposition," *The Journal of Neuroscience* 24(27):6144-6151.

Wilcock, D.M. et al. (May 1, 2003). "Intracranially Administered Anti-Aβ Antibodies Reduce β-Amyloid Deposition by Mechanisms Both Independent of and Associated with Microglial Activation," *The Journal of Neuroscience* 23(9):3745-3751.

Winkler, D.T. et al. (2001). "Spontaneous Hemorrhagic Stroke in a Mouse Model Cerebral Amyloid Angiopathy," *Journal of Neuroscience* 21(5):1619-1627.

Winter, G. et al. (1991). "Man-Made Antibodies," *Nature* 349:293-299.

Winter, G. et al. (1994). "Making Antibodies by Phage Display Technology," *Annu. Rev. Immunol.* 12:433-455.

Wittwer, A. J. et al. (1990). "Glycosylation at ASn-184 Inhibits the Conversation of Single-Chain to Two-Chain Tissue-Type Plasminogen Activator by Plasmin," *Biochem* 29(17):4175-4180.

Woffendin, C. et al. (1994). "Non Viral and Viral Delivery of a Human Immunodeficiency Virus Protective Gene Into Primary Human T Cells," *PNAS USA* 91:11581-11585.

Wright, A. et al. (1997). "Effect of Glycosylation on Antibody Function: Implacations for Genetic Engineering," *TibTech* 15:26-32.

Wright, A. et al. (1998). "Effect of C2-Associated Carbohydrate Structure on Ig Effector Function: Studies with Chimeric Mouse-Human IgG1 Antibodies in Glycosylation Mutants of Chinese Hamster Ovary Cells," *J. Immunol.* 160(7):3393-3402.

Wu, C. H. (1989). "Targeting Genes: Delivery and Persistent Expression of a Foreign Gene Driven by Mammalian Regulatory Elements in Vivo," *J. Biol. Chem.* 264(29):16985-16987.

Wu, G. Y. et al. (1991). "Receptor-Mediated Gene Delivery in Vivo," *The Journal of Biological Chemistry* 266(22):14338-14342.

Wu, G. Y. et al. (1994). "Incorporation of Adenovirus Into a Ligand-Based DNA Carrier System Results in Retention of Original Receptor Specificity and Enhances Targeted Gene Expression," *J. Biol. Chem* 269(15):11542-11546.

Wyss, D. F. et al. (1996). "The Structural Role of Sugars in Glycoproteins," *Current Opinion Biotech.* 7:409-416.

Yelton, D. E. et al. (1995). "Affinity Maturation of the BR96 Anti-Carcinoma Antibody by Codon-Based Mutagenesis," *J. Immunol.* 155:1994-2004.

Yocum, D.E. et al. (Jul. 1998). "Clinical and Immunologic Effects of a PRIMATIZED® Anti-CD4 Monoclonal Antibody in Active Rheumatoid Arthritis: Results of a Phase I, Single Dose, Dose Escalating Trial," *J. Rheumatol.* 25(7):1257-1262.

Zeitlin, L. et al. (2000). "Preventing Infectious Disease with Passive Immunization," *Microbes Infection* 2(6):701-708.

Zenke, M. et al. (1990). "Receptor-Mediated Endocytosis of Transferrin-Polycation Conjugates: An Efficient Way to Introduce DNA Into Hemapopoietic Cells," *PNAS USA* 87:3655-3659.

Zola, H. (1987). "Using Monoclonal Antibodies: Soluble Antigens," Chapter 6 In *Monoclonal Antibodies: A Manual of Techniques*, CRC Press, Inc. pp. 147-158.

Jan. 31, 2006 Non-Final Office Action issued in connection with U.S. Appl. No. 10/683,815.

Mar. 29, 2006, Examiner Interview Summary Record issued in connection with U.S. Appl. No. 10/683,815.

Jul. 21, 2006, Final Office Action issued in connection with U.S. Appl. No. 10/683,815.

Feb. 7, 2007 Non-Final Office Action issued in connection with U.S. Appl. No. 10/683,815.

Oct. 24, 2007, Final Office Action issued in connection with US Serial No. 10/683,815.

Mar. 16, 2009, Official Communication issued in connection with European Patent Application No. EP 03 770 790.8-2405.

International Search Report mailed May 3, 2006 for International Patent Application No. PCT/US2003/032080.

Aug. 25, 2006, International Preliminary Examination Report for International Patent Application No. PCT/US2003/32080.

Nov. 29, 2007, Official Communication issued in connection with European Patent Application No. EP 03 770 790.8-2405.

Jun. 22, 2007, Supplementary Search Report issued in connection with European Patent Application No. EP 03 770 790.8-2405.

Dec. 31, 2009, Final Office Action issued in connection with U.S. Appl. No. 11/652,821.

Mar. 16, 2009, Non-Final Office Action issued in connection with U.S. Appl. No. 11/652,821.

Mar. 14, 2008, Non-Final Office Action issued in connection with U.S. Appl. No. 11/194,989.

Jul. 6, 2009, Non-Final Office Action issued in connection with U.S. Appl. No. 11/194,989.

Oct. 13, 2009, Examiner Interview Summary Record (PTOL-413) issued in connection with U.S. Appl. No. 11/194,989.

International Search Report mailed Jul. 20, 2006 for International Patent Application No. PCT/US2005/027295.

International Preliminary Report on Patentability issued Jan. 30, 2007, for International Patent Application No. PCT/US2005/027295.

Written Opinion of the ISA issued Jan. 30, 2007, for International Patent Application No. PCT/US2005/027295.

Dec. 16, 2009, Notice of Allowance and Fees Due and Examiner Interview Record Summary PTOL-413 issued in connection with U.S. Appl. No. 11/413,817.

Jun. 1, 2009, Non-Final Office Action issued in connection with U.S. Appl. No. 11/413,817.

Dec. 9, 2008, Non-Final Office Action issued in connection with U.S. Appl. No. 11/413,817.

Aug. 27, 2009, Examiner Interview Summary Record (PTOL-413) issued in connection with U.S. Appl. No. 11/413,817.

International Search Report published May 10, 2007, for International Patent Application No. PCT/US2006/016071.

Written Opinion of the ISA issued Oct. 29, 2007, for International Patent Application No. PCT/US2006/016071.

International Preliminary Report on Patentability issued Oct. 30, 2007, for International Patent Application No. PCT/US2006/016071.

Feb. 15, 2008, Official Communication issued in connection with European Patent Application No. EP 05 778 628.7.

Mar. 12, 2008, Official Communication issued in connection with European Patent Application No. EP 06 751 677.3 -2402.

Jan. 6, 2010, Notice of Allowance and Fees Due issued in connection with U.S. Appl. No. 11/194,989.

FIGURE 1

Bold=Kabat CDR
Underline=Chothia CDR

9TL Heavy chain

```
                                                                          H1
 1         5          10         15         20         25         29
 Q V Q L V Q S G A E V K K P G A S V K V S C K A S G Y Y T
                                                                          H2
30        35         40         45         50         55         58
 E A Y Y I H W V R Q A P G Q G L E W M G R I D P A T G N T 59 60     65         70         75         80         85    87
 K Y A P R L Q D R V T M T R D T S T S T V Y M E L S S L R
                                      H3
88    90       95        100        105        110        115
 S E D T A V Y Y C A S L Y S L P V Y W G Q G T T V T V S S
```

9TL Light chain

```
                                                                          L1
 1         5          10         15         20         25         29
 D V V M T Q S P L S L P V T L G Q P A S I S C K S S Q S L
                                                                          L2
30        35         40         45         50         55         58
 L Y S D A K T Y L N W F Q Q R P G Q S P R R L I Y Q I S R 59 60     65         70         75         80         85    87
 L D P G V P D R F S G S G S G T D F T L K I S R V E A E D
                                      L3
88    90       95        100        105        110        114
 V G V Y Y C L Q G T H Y P V L F G Q G T R L E I K R T
```

FIGURE 6
A. Parenchymal Congo Red Frontal Cortex
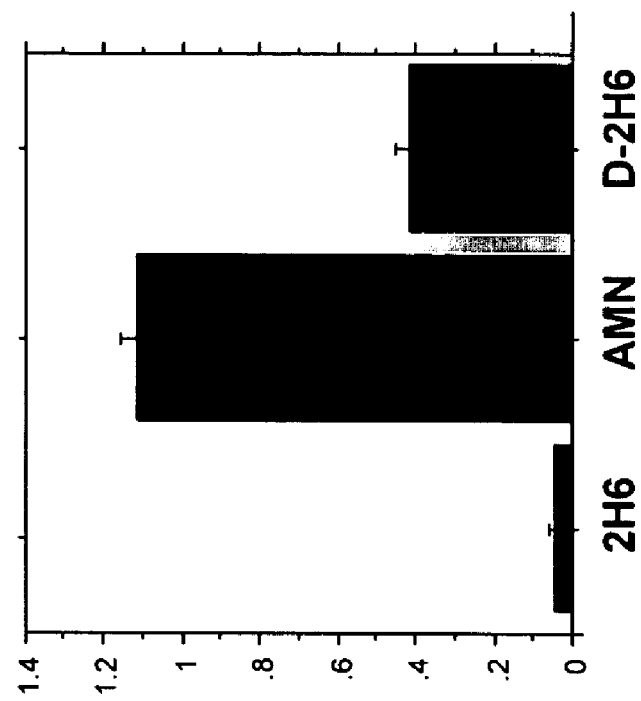
B. Parenchymal Congo Red Hippocampus
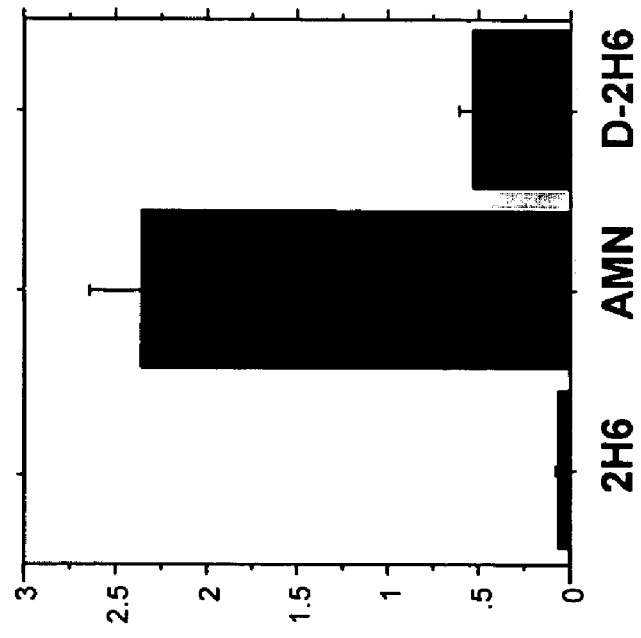

FIGURE 7
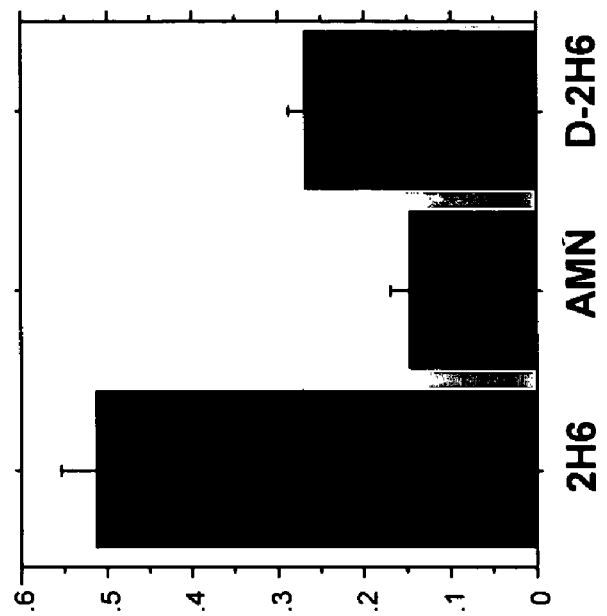
B. Vascular Congo Red Frontal Cortex
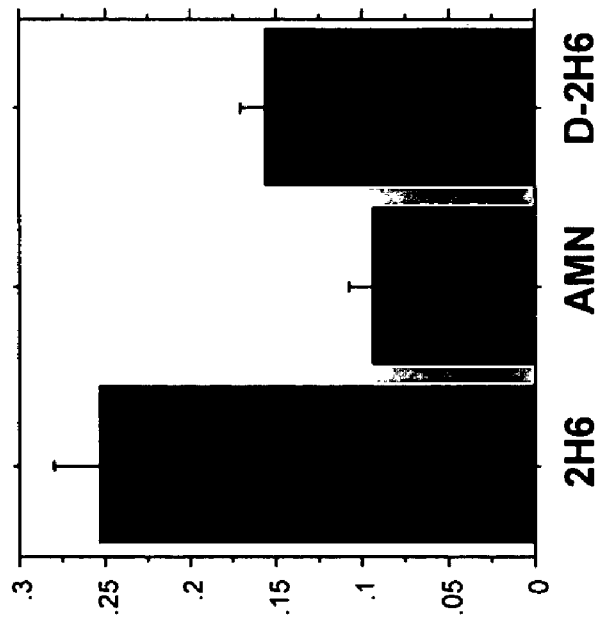
A. Vascular Congo Red Hippocampus Epitope mapping:

| 15 MER PEPTIDE | | 2294 | 6G |
|---|---|---|---|
| 19 | FFAEDVGSNKGAIIGG | NB | NB |
| 20 | FAEDVGSNKGAIIGLG | >3 | >3 |
| 21 | AEDVGSNKGAIIGLMG | 2.9 | >3 |
| 22 | EDVGSNKGAIIGLMVG | >3 | >3 |
| 23 | DVGSNKGAIIGLMVGG | >3 | 2.3 |
| 24 | VGSNKGAIIGLMVGGG | >3 | 2.1 |
| 25 | GSNKGAIIGLMVGGVG | >3 | 1.5 |
| 26 | SNKGAIIGLMVGGVVG | >3 | NB |
| 27 | NKGAIIGLMVGGVVIG | NB | NB |
| 28 | KGAIIGLMVGGVVIAG | NB | NB |

10 MER PEPTIDES BINDING DATA: MINIMUM EPITOPE TESTED

| | 2294 | 6G |
|---|---|---|
| VGSNKGAIIGG | NB | NB |
| GSNKGAIIGLG | 2 | >3 |
| SNKGAIIGLMG | NB | NB |

FIGURE 14

US 7,807,165 B2

ANTIBODIES DIRECTED AGAINST AMYLOID-BETA PEPTIDE AND METHODS USING SAME

CROSS-REFERENCE TO RELATED APPLICATIONS

This application claims the priority benefit of U.S. provisional application Ser. Nos. 60/592,494, filed Jul. 30, 2004; 60/653,197, filed Feb. 14, 2005; and 60/676,093, filed Apr. 29, 2005; all of which are incorporated herein by reference in their entirety.

FIELD OF THE INVENTION

The invention concerns antibodies to amyloid-beta peptide. The invention further concerns use of such antibodies in the treatment and/or prevention of diseases, such as Alzheimer's disease.

STATEMENT REGARDING FEDERALLY SPONSORED RESEARCH OR DEVELOPMENT

Not applicable.

BACKGROUND OF THE INVENTION

Alzheimer's disease (AD) is a degenerative brain disorder characterized clinically by progressive memory deficits, confusion, gradual physical deterioration and, ultimately, death. Approximately 15 million people worldwide are affected by Alzheimer's disease, and the number is expected to increase dramatically as lifespan increases. Histologically, the disease is characterized by neuritic plaques, found primarily in the association cortex, limbic system and basal ganglia. The major constituent of these plaques is amyloid beta peptide (A$\beta$), which is the cleavage product of beta amyloid precursor protein ($\beta$APP or APP). APP is a type I transmembrane glycoprotein that contains a large ectopic N-terminal domain, a transmembrane domain, and a small cytoplasmic C-terminal tail. Alternative splicing of the transcript of the single APP gene on chromosome 21 results in several isoforms that differ in the number of amino acids.

A$\beta$ appears to have a central role in the neuropathology of Alzheimer's disease. Familial forms of the disease have been linked to mutations in APP and the presenilin genes (Tanzi et al., 1996, Neurobiol. Dis. 3:159-168; Hardy, 1996, Ann. Med. 28:255-258). Diseased-linked mutations in these genes result in increased production of the 42-amino acid form of A$\beta$, the predominant form found in amyloid plaques. Moreover, immunization of transgenic mice that overexpress a disease-linked mutant form of APP with human A$\beta$ reduces plaque burden and associated pathologies (Schenk et al., 1999, Nature 400:173-177; WO 99/27944), and peripheral administration of antibodies directed against A$\beta$ also reduces plaque burden in the brain (Bard et al., 2000, Nature Medicine 6(8):916-919; WO 2004/032868; WO 00/72880).

It has been reported that Fc-mediated phagocytosis by microglial cells and/or macrophages is important to the process of plaque clearance in vivo. Bard et al., Proc. Natl. Acad. Sci. USA 100, 2023-2028 (2003). However, it has also been reported that non-Fc-mediated mechanisms are involved in clearance of amyloid-$\beta$ in vivo by immunotherapy. Bacskai et al., J. Neurosci. 22:7873-7878 (2002); Das et al., J. Neurosci. 23:8532-8538 (2003).

Antibody therapy therefore provides a promising approach to the treatment and prevention of Alzheimer's disease. However, human clinical trials with a vaccine including A$\beta$1-42 were suspended due to meningoencephalititis in a subset of patients. Orgogozo et al., Neruology 61:7-8 (2003); Ferrer et al., Brain Pathol. 14:11-20 (2004). It has been reported that passive immunization with an N-terminal specific anti-A$\beta$ antibody results in a significant reduction of mainly diffuse amyloid, but induces an increase of cerebral microhemorrhage frequency in transgenic mice that exhibit the age-related development of amyloid plaques and neurodegeneration as well as cerebral amyloid angiopathy (CAA) similar to that observed in the human AD brain. Pfeifer et al., Science 298:1379 (2002). It has been suggested that exacerbation of cerebral amyloid angiopathy (CAA)-associated microhemorrhage in APP transgenic mice by passive immunization with antibody directed to beta-amyloid is dependent on antibody recognition of deposited forms of amyloid beta peptide. Racke et al., J. Neurosci. 25:629-636 (2005). Passive immunization with antibodies against a peptide component of an amyloid deposit, which antibodies are devoid of Fc regions, has been suggested in order to decrease the risk of inflammation. WO 03/086310. There remains a need for antibodies and other immunotherapeutic agents directed against A$\beta$ having improved efficacy and safety profile, and which are suitable for use with human patients.

Throughout this application various publications (including patents and patent applications) are referenced. The disclosures of these publications in their entireties are hereby incorporated by reference.

BRIEF SUMMARY OF THE INVENTION

Section I

The present invention provides methods for treating a disease characterized by aberrant deposition of a protein in the brain of a subject. The methods comprise administering to the subject an effective amount of a pharmaceutical composition comprising an antibody that specifically binds to the protein or the protein deposit, or a polynucleotide encoding the antibody, wherein the antibody has impaired effector function.

The invention also provides methods for treating or preventing diseases associated with amyloid deposit of A$\beta$ (e.g., deposit in the brain tissue and cerebral vasculature) in a subject, such as Alzheimer's disease, Down's syndrome, multi-infarct dementia, mild cognitive impairment, and cerebral amyloid angiopathy. The method comprises administering to the subject an effective amount of a pharmaceutical composition comprising an antibody that specifically binds to a beta-amyloid peptide or an aggregated form of a beta-amyloid peptide, or a polynucleotide encoding the antibody, wherein the antibody has impaired effector function.

The invention also provides methods of delaying development of a symptom associated with diseases associated with amyloid deposit of A$\beta$ in a subject, such as Alzheimer's disease, comprising administering to the subject an effective dosage of a pharmaceutical composition comprising an antibody that specifically binds to a beta-amyloid peptide or an aggregated form of a beta-amyloid peptide, or a polynucleotide encoding the antibody, wherein the antibody has impaired effector function.

The invention also provides methods of suppressing formation of amyloid plaques and/or amyloid accumulation in a subject comprising administering to the subject an effective dosage of a pharmaceutical composition comprising an antibody that specifically binds to a beta-amyloid peptide or an aggregated form of a beta-amyloid peptide, or a polynucleotide encoding the antibody, wherein the antibody has impaired effector function. In some embodiments, the amyloid plaques are in the brain (brain tissue) of the subject. In some embodiments, the amyloid plaques are in the cerebral vasculature. In some embodiments, the amyloid accumulation is in the circulatory system.

The invention also provides methods of reducing amyloid plaques and/or amyloid accumulation in a subject comprising administering to the subject an effective dosage of a pharmaceutical composition comprising an antibody that specifically binds to a beta-amyloid peptide or an aggregated form of a beta-amyloid peptide, or a polynucleotide encoding the antibody, wherein the antibody has impaired effector function. In some embodiments, the amyloid plaques are in the brain (brain tissue) of the subject. In some embodiments, the amyloid plaques are in the cerebral vasculature. In some embodiments, the amyloid accumulation is in the circulatory system.

The invention also provides methods of removing or clearing amyloid plaques and/or amyloid accumulation in a subject comprising administering to the subject an effective dosage of a pharmaceutical composition comprising an antibody that specifically binds to a beta-amyloid peptide or an aggregated form of a beta-amyloid peptide, or a polynucleotide encoding the antibody, wherein the antibody has impaired effector function. In some embodiments, the amyloid plaques are in the brain (brain tissue) of the subject. In some embodiments, the amyloid plaques are in the cerebral vasculature. In some embodiments, the amyloid accumulation is in the circulatory system.

The invention also provides methods for inhibiting the accumulation of Aβ peptide in a tissue comprising contacting the tissue with an antibody that specifically binds to a beta-amyloid peptide or an aggregated form of a beta-amyloid peptide, wherein the antibody has impaired effector function.

The invention also provides methods of reducing Aβ peptide (such as soluble, oligomeric, and deposited form) in a subject comprising administrating to the subject an effective amount of an antibody that specifically binds to a beta-amyloid peptide or an aggregated form of a beta-amyloid peptide, or a polynucleotide encoding the antibody, wherein the antibody has impaired effector function. In some embodiments, the accumulation of Aβ peptide is inhibited and/or reduced in the brain. In some embodiments, the toxic effects of Aβ peptide are inhibited and/or reduced. Thus, the method of the invention can be used to treat any disease in which accumulation of Aβ peptide is present or suspected, such as Alzheimer's disease, Down's syndrome, Parkinson's disease, and multi-infarct dementia.

The invention also provides methods of improving cognition or reversing cognitive decline associated with diseases associated with amyloid deposit of Aβ in a subject, such as Alzheimer's disease, comprising administering to the subject an effective dosage of a pharmaceutical composition comprising an antibody that specifically binds to a beta-amyloid peptide or an aggregated form of a beta-amyloid peptide, or a polynucleotide encoding the antibody, wherein the antibody has impaired effector function.

The invention also provides methods for treating or preventing diseases associated with amyloid deposit of Aβ, comprising administering to the subject an effective dosage of a pharmaceutical composition comprising an antibody that specifically binds to a beta-amyloid peptide or an aggregated form of a beta-amyloid peptide, wherein the antibody comprises an Fc region with a variation from a naturally occurring Fc region, wherein the variation results in impaired effector function. In some embodiments, the administration of the antibody causes less cerebral microhemorrhage than administration of an antibody without the variation.

Polypeptides that specifically bind to an Aβ peptide or an aggregated form of an Aβ peptide and comprises a heavy chain constant region having impaired effector function may also be used for any of the methods described herein. In some embodiments, the polypeptide comprises a sequence (e.g., one or more CDRs) derived from antibody 9TL or its variants shown in Table 3. In some embodiments, the polypeptide comprises a sequence (e.g., one or more CDRs) derived from antibody 6G.

The antibody and polypeptide used for the methods of the invention specifically bind to an Aβ peptide or an aggregated form of an Aβ peptide, but have impaired effector function. In some embodiments, the antibody or polypeptide is not a F(ab')$_2$ fragment. In some embodiments, the antibody or polypeptide is not a Fab fragment. In some embodiments, the antibody or polypeptide is not a single chain antibody scFv.

In some embodiments, the antibody or the polypeptide comprises a heavy chain constant region having impaired effector function, wherein the heavy chain constant region comprises an Fc region. In some embodiments, the N-glycosylation in the Fc region is removed. In some embodiments, the Fc region comprises a mutation within the N-glycosylation recognition sequence, whereby the Fc region of the antibody or polypeptide is not N-glycosylated. In some embodiments, the Fc region is PEGylated. In some embodiments, the heavy chain constant region of the antibody or the polypeptide is a human heavy chain IgG2a constant region containing the following mutations: A330P331 to S330S331 (amino acid numbering with reference to the wildtype IgG2a sequence). In some embodiments, the antibody or the polypeptide comprises a constant region of IgG4 comprising the following mutations: E233F234L235 to P233V234A235.

In some embodiments, the antibody or polypeptide specifically binds to an epitope within residues 1-16 of Aβ peptide. In some embodiments, the antibody or polypeptide specifically binds to the N-terminus of the Aβ peptide. In some embodiments, the antibody or the polypeptide specifically binds to an epitope within residues 16-28 of Aβ peptide. In some embodiments, the antibody specifically binds to an epitope on the C-terminal side of an Aβ peptide, such as an epitope starting from amino acid 25 or later. The antibody may specifically bind to the free C-terminus amino acid of C-terminus truncated Aβ peptide, for example, Aβ 1-37, 1-38, 1-39, 1-40, 1-41, 1-42, 1-43. In some embodiments, the antibody or the polypeptide specifically binds to an epitope within residues 28-40 of A$β_{1-40}$ peptide. In some embodiments, the antibody or the polypeptide specifically binds to an epitope within residues 28-42 of A$β_{1-42}$ peptide. In some embodiments, the antibody or the polypeptide specifically binds to an epitope within residues 28-43 of A$β_{1-43}$ peptide. In some embodiments, the antibody or the polypeptide specifically binds to Aβ peptide without binding to full-length amyloid precursor protein (APP). In some embodiments, the antibody or the polypeptide specifically binds to the aggregated form of Aβ without binding to the soluble form. In some embodiments, the antibody or the polypeptide specifically binds to the soluble form of Aβ without binding to the aggregated form. In some embodiments, the antibody or the polypeptide specifically binds to both aggregated form and soluble forms of Aβ.

In some embodiments, the antibody or the polypeptide specifically binds to a C-terminal peptide 33-40 of A$β_{1-40}$. In some embodiments, the antibody or the polypeptide specifically binds to an epitope on A$β_{1-40}$ that includes amino acid 35-40. In some embodiments, the antibody or the polypeptide specifically binds to an epitope on A$β_{1-40}$ that includes amino acid 36-40. In some embodiments, the antibody or the polypeptide specifically binds to an epitope on $A\beta_{1-40}$ that includes amino acid 39 and/or 40. In some embodiments, the antibody or the polypeptide specifically binds to $A\beta_{1-40}$ but do not specifically bind to $A\beta_{1-42}$ and/or $A\beta_{1-43}$. In some embodiments, the antibody comprises the variable region of antibody 9TL or an antibody derived from 9TL described herein. In some embodiments, the antibody or polypeptide competitively inhibits binding of antibody 9TL and/or antibody or polypeptide derived from 9TL to $A\beta_{1-40}$.

In some embodiments, the antibody or the polypeptide binds to $A\beta_{1-40}$ with higher affinity than its binding to $A\beta_{1-42}$ and $A\beta_{1-43}$. In some embodiments, the antibody binds to an epitope on $A\beta_{1-40}$ that includes amino acids 25-34 and 40. In some embodiments, the antibody comprises the variable region of antibody 6G or an antibody derived from 6G described herein. In some embodiments, the antibody or polypeptide competitively inhibits binding of antibody 6G and/or antibody or polypeptide derived from 6G to $A\beta$.

Administration of antibody or polypeptide that specifically binds to an $A\beta$ peptide and has impaired effector function may be by any means known in the art, including: intravenously, subcutaneously, via inhalation, intraarterially, intramuscularly, intracardially, intraventricularly, parenteral, intrathecally, and intraperitoneally. Administration may be systemic, e.g. intravenously, or localized. This also generally applies to polypeptides and polynucleotides of the invention.

The invention also provides pharmaceutical composition comprising an effective amount of any of the antibodies or polypeptides that specifically bind to an $A\beta$ peptide or an aggregated form of an $A\beta$ peptide and have impaired effector function, or polynucleotides encoding the antibodies or polypeptides, and a pharmaceutical acceptable excipient.

The invention also provides kits and compositions comprising any one or more of the compositions comprising an effective amount of any of the antibodies or polypeptides that specifically bind to an $A\beta$ peptide or an aggregated form of an $A\beta$ peptide and have impaired effector function, or polynucleotides encoding the antibodies or polypeptides. These kits, generally in suitable packaging and provided with appropriate instructions, are useful for any of the methods described herein.

The invention also provides a method of producing a therapeutic humanized antibody for treatment of a disease associated with amyloid deposits of $A\beta$ peptide in the brain of a human subject, comprising selecting a first humanized antibody that specifically binds to $A\beta$ peptide; and altering the Fc region of the antibody to provide a therapeutic humanized antibody having impaired effector function relative to the first humanized antibody.

Section II

The invention disclosed herein concerns antibodies that bind to C-terminus of $A\beta_{1-40}$ peptide (SEQ ID NO:15 shown in Table 4). Accordingly, in one aspect, the invention is an antibody 9TL (interchangeably termed "9TL") that is produced by expression vectors having ATCC Accession Nos. PTA-6124 and PTA-6125. The amino acid sequences of the heavy chain and light chain variable regions of 9TL are shown in FIG. 1. The complementarity determining region (CDR) portions of antibody 9TL (including Chothia and Kabat CDRs) are also shown in FIG. 1. It is understood that reference to any part of or entire region of 9TL encompasses sequences produced by the expression vectors having ATCC Accession Nos. PTA-6124 and PTA-6125, and/or the sequences depicted in FIG. 1.

In another aspect, the invention also provides antibody variants of 9TL with amino acid sequences depicted in Table 3.

In another aspect, the invention is an antibody comprising a fragment or a region of the antibody 9TL or its variants shown in Table 3. In one embodiment, the fragment is a light chain of the antibody 9TL. In another embodiment, the fragment is a heavy chain of the antibody 9TL. In yet another embodiment, the fragment contains one or more variable regions from a light chain and/or a heavy chain of the antibody 9TL. In yet another embodiment, the fragment contains one or more variable regions from a light chain and/or a heavy chain shown in FIG. 1. In yet another embodiment, the fragment contains one or more CDRs from a light chain and/or a heavy chain of the antibody 9TL.

In another aspect, the invention provides polypeptides (which may or may not be an antibody) comprising any one or more of the following: a) one or more CDR(s) of antibody 9TL or its variants shown in Table 3; b) CDR H3 from the heavy chain of antibody 9TL or its variants shown in Table 3; c) CDR L3 from the light chain of antibody 9TL or its variants shown in Table 3; d) three CDRs from the light chain of antibody 9TL or its variants shown in Table 3; e) three CDRs from the heavy chain of antibody 9TL or its variants shown in Table 3; f) three CDRs from the light chain and three CDRs from the heavy chain of antibody 9TL or its variants shown in Table 3. The invention further provides polypeptides (which may or may not be an antibody) comprising any one or more of the following: a) one or more (one, two, three, four, five, or six) CDR(s) derived from antibody 9TL or its variants shown in Table 3; b) a CDR derived from CDR H3 from the heavy chain of antibody 9TL; and/or c) a CDR derived from CDR L3 from the light chain of antibody 9TL. In some embodiments, the CDR is a CDR shown in FIG. 1. In some embodiments, the one or more CDRs derived from antibody 9TL or its variants shown in Table 3 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of 9TL or its variants.

In some embodiments, the CDR is a Kabat CDR. In other embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined.

In some embodiments, the polypeptide (such as an antibody) comprises an amino acid sequence shown in SEQ ID NO:5, wherein L1 is L, V, or I; wherein Y2 is Y or W; wherein S3 is S, T, or G; wherein L4 is L, R, A, V, S, T, Q, or E; wherein V6 is V, I, T, P, C, Q, S, N, or F; and wherein Y7 is Y, H, F, W, S, I, V, or A. In some embodiments, the amino acid sequence is a CDR3 in a heavy chain variable region. For convenience herein, "is" in this context or reference to an amino acid refers to choices of amino acid(s) for a given position with reference to the position in the SEQ ID. For example, "L1 is L, V, or I" refers to amino acid L at position 1 in SEQ ID NO:5 may be substituted with V or I.

In some embodiments, the polypeptide (such as an antibody) comprises an amino acid sequence shown in SEQ ID NO:6, wherein Y8 is Y, A, or H; and wherein A11 is A or S; and wherein K12 is K or A. In some embodiments, the amino acid sequence is a CDR1 in a light chain variable region.

In some embodiments, the polypeptide (such as an antibody) comprises an amino acid sequence shown in SEQ ID NO:8, wherein L1 is L, M, N, C, F, V, K, S, Q, G, S; wherein G3 is G, S, or T; wherein T4 is T or S; wherein H5 is H or L; wherein Y6 is Y, P, A, W, Q, M, S, or E; wherein V8 is V, L, K, H, T, A, E, or M; and wherein L9 is L, I, T, S, or V. In some embodiments, the amino acid sequence is a CDR3 in a light chain variable region.

In some embodiments, the polypeptide (such as an antibody) comprises a heavy chain variable region comprising (a) a CDR1 region shown in SEQ ID NO:3; (b) a CDR2 region shown in SEQ ID NO:4; and (c) a CDR3 region shown in SEQ ID NO:5, wherein L1 is L, V, or I; wherein Y2 is Y or W; wherein S3 is S, T, or G; wherein L4 is L, R, A, V, S, T, Q, or E; wherein V6 is V, I, T, P, C, Q, S, N, or F; and wherein Y7 is Y, H, F, W, S, I, V, or A.

In some embodiments, the polypeptide (such as an antibody) comprises a light chain variable region comprising (a) a CDR1 region shown in SEQ ID NO:6, wherein Y8 is Y, A, or H; and wherein A11 is A or S; and wherein K12 is K or A; (b) a CDR2 region shown in SEQ ID NO:7; and (c) a CDR3 region shown in SEQ ID NO:8, wherein L1 is L, M, N, C, F, V, K, S, Q, G, S; wherein G3 is G, S, or T; wherein T4 is T or S; wherein H5 is H or L; wherein Y6 is Y, P, A, W, Q, M, S, or E; wherein V8 is V, L, K, H, T, A, E, or M; and wherein L9 is L, I, T, S, or V.

In some embodiments, the antibody of the invention is a human antibody. In other embodiments, the antibody of the invention is a humanized antibody. In some embodiments, the antibody is monoclonal. In some embodiments, the antibody (or polypeptide) is isolated. In some embodiments, the antibody (or polypeptide) is substantially pure.

The heavy chain constant region of the antibodies may be from any types of constant region, such as IgG, IgM, IgD, IgA, and IgE; and any isotypes, such as IgG1, IgG2, IgG3, and IgG4.

In some embodiments, the antibody comprises a modified constant region, such as a constant region that is immunologically inert (which includes partially immunologically inert, and is used interchangeably with the term "having impaired effector function"), e.g., does not trigger complement mediated lysis, does not stimulate antibody-dependent cell mediated cytotoxicity (ADCC), or does not activate microglia. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2a constant region comprising the following mutations: A330P331 to S330S331 (amino acid numbering with reference to the wildtype IgG2a sequence). Eur. J. Immunol. (1999) 29:2613-2624. In some embodiments, the antibody comprises a constant region of IgG4 comprising the following mutations: E233F234L235 to P233V234A235. In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

In another aspect, the invention provides a polynucleotide (which may be isolated) comprising a polynucleotide encoding a fragment or a region of the antibody 9TL or its variants shown in Table 3. In one embodiment, the fragment is a light chain of the antibody 9TL. In another embodiment, the fragment is a heavy chain of the antibody 9TL. In yet another embodiment, the fragment contains one or more variable regions from a light chain and/or a heavy chain of the antibody 9TL. In yet another embodiment, the fragment contains one or more (i.e., one, two, three, four, five, six) complementarity determining regions (CDRs) from a light chain and/or a heavy chain of the antibody 9TL.

In another aspect, the invention is a polynucleotide (which may be isolated) comprising a polynucleotide that encodes for antibody 9TL or its variants shown in Table 3. In some embodiments, the polynucleotide comprises either or both of the polynucleotides shown in SEQ ID NO:9 and SEQ ID NO:10.

In another aspect, the invention provides polynucleotides encoding any of the antibodies (including antibody fragments) or polypeptides described herein.

In another aspect, the invention provides vectors (including expression and cloning vectors) and host cells comprising any of the polynucleotide disclosed herein. In some embodiments, the vector is pDb.9TL.hFc2a having ATCC No. PTA-6124. In other embodiments, the vector is pEb.9TL.hK having ATCC No. PTA-6125.

In another aspect, the invention is a host cell comprising a polynucleotide encoding any of the antibodies described herein.

In another aspect, the invention is a complex of Aβ$_{1-40}$ bound by antibody 9TL or its variants shown in Table 3.

In another aspect, the invention is a complex of Aβ$_{1-40}$ bound by any of the antibodies or polypeptides described herein.

In another aspect, the invention is a pharmaceutical composition comprising an effective amount of any of the polypeptides (including antibodies, such as an antibody comprising one or more CDRs of antibody 9TL) or polynucleotides described herein, and a pharmaceutically acceptable excipient.

In another aspect, the invention is a method of generating antibody 9TL comprising culturing a host cell or progeny thereof under conditions that allow production of antibody 9TL, wherein the host cell comprises an expression vector that encodes for antibody 9TL; and, in some embodiments, purifying the antibody 9TL. In some embodiments, the expression vector comprises one or both of the polynucleotide sequences shown in SEQ ID NO:9 and SEQ ID NO:10.

In another aspect, the invention provides methods of generating any of the antibodies or polypeptides described herein by expressing one or more polynucleotides encoding the antibody (which may be separately expressed as a single light or heavy chain, or both a light and a heavy chain are expressed from one vector) or the polypeptide in a suitable cell, generally followed by recovering and/or isolating the antibody or polypeptides of interest.

The invention also provides a method for preventing, treating, inhibiting, or delaying the development of Alzheimer's disease and other diseases associated with altered Aβ or βAPP expression, or accumulation of Aβ peptide, such as Down's syndrome, Parkinson's disease, multi-infarct dementia, mild cognitive impairment, cerebral amyloid angiopathy, and AIDS. The method comprises administering an effective dosage a pharmaceutical composition comprising an antibody, a polypeptide, or a polynucleotide of the invention to a subject.

The invention also provides a method of delaying development of a symptom associated with Alzheimer's disease or other diseases related to accumulation of Aβ peptide in a subject comprising administering an effective dosage of a pharmaceutical composition comprising an antibody, a polypeptide, or a polynucleotide of the invention to the subject.

The invention also provides a method of suppressing formation of amyloid plaques and/or amyloid accumulation in a subject comprising administering an effective dosage of a pharmaceutical composition comprising an antibody, a polypeptide, or a polynucleotide of the invention to the subject. In some embodiments, the amyloid plaques are in the brain (brain tissue) of the subject. In some embodiments, the amyloid plaques are in the cerebral vasculature. In other embodiments, the amyloid accumulation is in the circulatory system.

The invention also provides a method of reducing amyloid plaques and/or amyloid accumulation in a subject comprising administering an effective dosage of a pharmaceutical composition comprising an antibody, a polypeptide, or a polynucleotide of the invention to the subject. In some embodiments, the amyloid plaques are in the brain (brain tissue) of the subject. In some embodiments, the amyloid plaques are in the cerebral vasculature. In other embodiments, the amyloid accumulation is in the circulatory system.

The invention also provides a method of removing or clearing amyloid plaques and/or amyloid accumulation in a subject comprising administering an effective dosage of a pharmaceutical composition comprising an antibody, a polypeptide, or a polynucleotide of the invention to the subject. In some embodiments, the amyloid plaques are in the brain (brain tissue) of the subject. In some embodiments, the amyloid plaques are in the cerebral vasculature. In other embodiments, the amyloid accumulation is in the circulatory system.

Additionally, the invention provides a method for inhibiting the accumulation of Aβ peptide in a tissue comprising contacting the tissue with an antibody or a polypeptide of the invention.

The invention also provides a method of reducing Aβ peptide (such as soluble, oligomeric and deposited form) in the brain of an individual comprising administering to the individual an effective amount of an antibody or a polypeptide of the invention. In some embodiments, the accumulation of Aβ peptide is inhibited and/or reduced in the brain. In some embodiments, the toxic effects of Aβ peptide are inhibited and/or reduced. Thus, the method of the invention can be used to treat any disease in which accumulation of Aβ peptide is present or suspected, such as Alzheimer's disease, Down's syndrome, Parkinson's disease, multi-infarct dementia, mild cognitive impairment, and cerebral amyloid angiopathy.

The invention also provides methods of improving cognition or reversing cognitive decline associated with diseases associated with amyloid deposit of Aβ in the brain of an individual, such as Alzheimer's disease, comprising administering an effective dosage of a pharmaceutical composition comprising an antibody, a polypeptide, or a polynucleotide of the invention to the individual.

Any antibodies, polypeptides, or polynucleotides described herein may be used for the methods of the invention. In some embodiments, the antibody is antibody 9TL.

Antibodies and polypeptides of the invention can further be used in the detection, diagnosis and monitoring of Alzheimer's disease and other diseases associated with altered Aβ or βAPP expression, such as Down's syndrome, and AIDS. The method comprises contacting a specimen of a patient suspected of having altered Aβ or βAPP expression with an antibody of the invention and determining whether the level of Aβ or βAPP differs from that of a control or comparison specimen. In some embodiments, serum level of Aβ is measured before and after administration of an anti-Aβ antibody; and any increase of serum level of Aβ is assessed.

Administration of any antibody or polypeptide of the invention may be by any means known in the art, including: intravenously, subcutaneously, via inhalation, intraarterially, intramuscularly, intracardially, intraventricularly, parenteral, intrathecally, and intraperitoneally. Administration may be systemic, e.g. intravenously, or localized. This also generally applies to polypeptides and polynucleotides of the invention.

In another aspect, the invention provides kits and compositions comprising any one or more of the compositions described herein. These kits, generally in suitable packaging and provided with appropriate instructions, are useful for any of the methods described herein.

BRIEF DESCRIPTION OF THE SEVERAL VIEWS OF THE DRAWING(S)

FIG. 1 shows the amino acid sequence of the heavy chain variable region (SEQ ID NO:1) and light chain variable region (SEQ ID NO:2) of the 9TL antibody. The Kabat CDRs are in bold text, and the Chothia CDRs are underlined. The amino acid residues for the heavy chain and light chain variable region are numbered sequentially.

FIG. 2 shows epitope mapping of antibody 9TL by peptide competition. $A\beta_{1-40}$ peptide was immobilized on the SA chip. Monoclonal antibody 2289 and 9TL Fab fragment (50 nM each), each of which was preincubated for 1 h with 10 µM various peptide (amino acids 28-40, 1-40, 1-28, 28-42, 22-35, 1-16, 1-43, 33-40, 1-38, or 17-40 of Aβ) or no peptide, and was then flowed onto the chip. Binding of the antibody Fab fragment to immobilized $A\beta_{1-40}$ peptide was measured.

Figure 3:
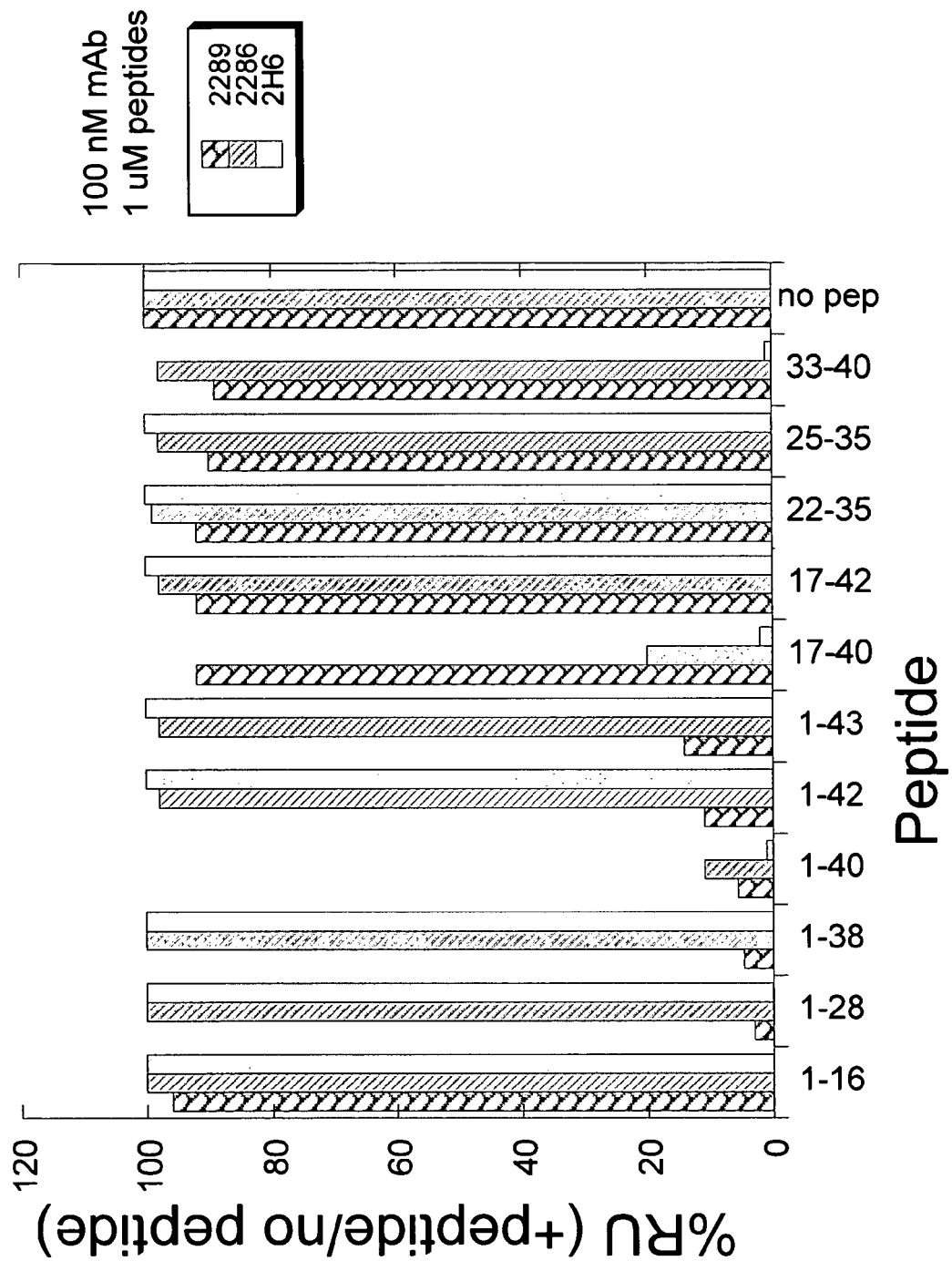

FIG. 3 is a graph showing epitope mapping of antibody 2H6 by peptide competition. $A\beta_{1-40}$ peptide was immobilized on the SA chip. Monoclonal antibody 2289, 2286, or 2H6 (100 nM each), each of which was preincubated for 1 h with 16 µM various peptide (amino acids 1-16, 1-28, 1-38, 1-40, 1-42, 1-43, 17-40, 17-42, 22-35, 25-35, or 33-40 of Aβ) or no peptide, was flowed onto the chip. Binding of the antibody to immobilized $A\beta_{1-40}$ peptide was measured.

Figure 4:
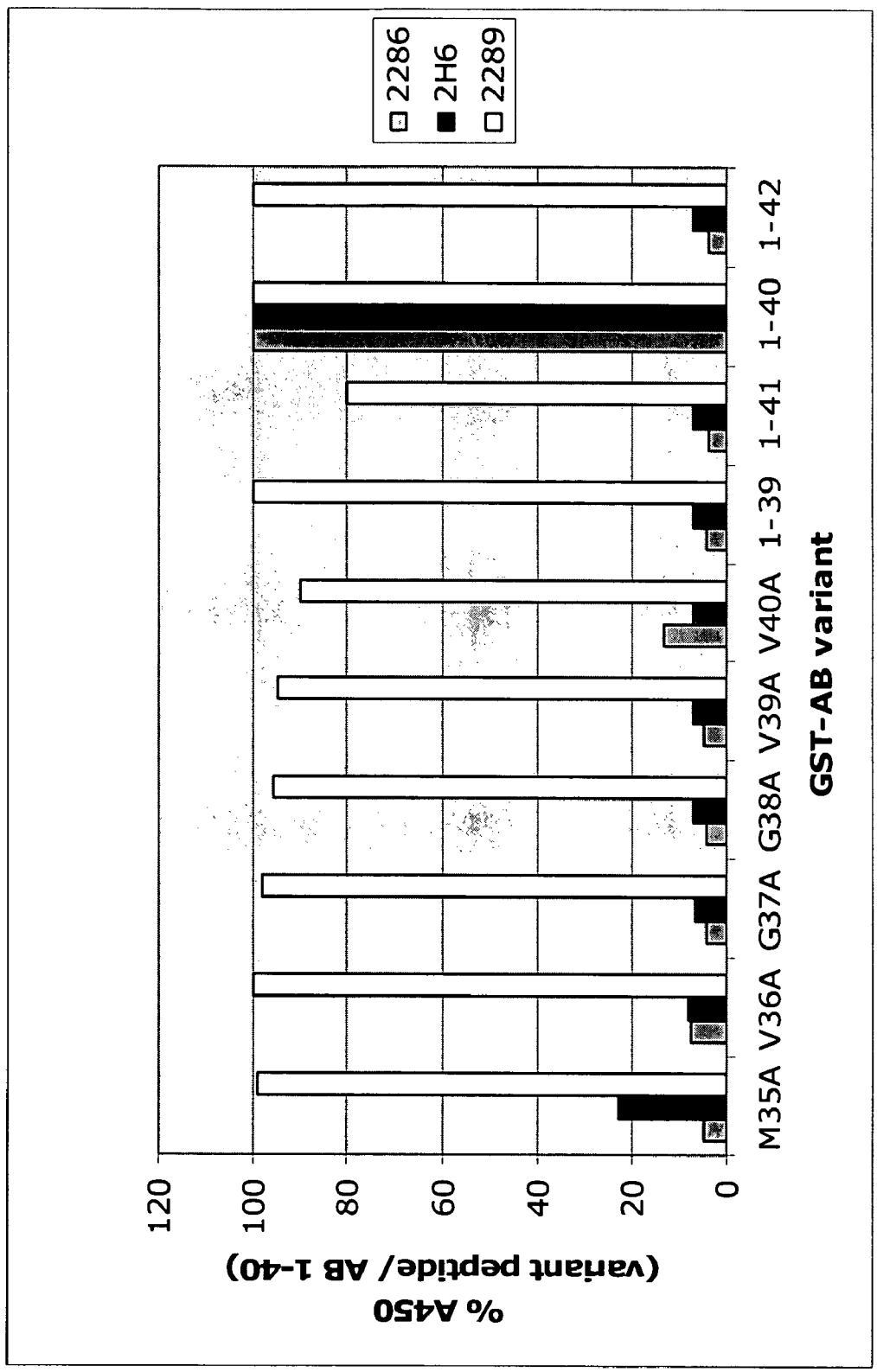

FIG. 4 is a graph showing binding of antibody 2H6, 2286, and 2289 to different Aβ peptide C-terminal variants. GST-Aβ variants (M35A, V36A, G37A, G38A, V39A, or V40A), or GST-Aβ peptide 1-39, 1-41, 1-40, 1-42 were immobilized on ELISA plate. Monoclonal antibody 2286, 2H6, or 2289 (0.3 nM each mAb) was incubated with each of the immobilized peptides, and their binding was detected by further incubating with biotinylated anti-mouse IgG (H+ L) and followed by Sterptavidin-HRP.

Figure 5:
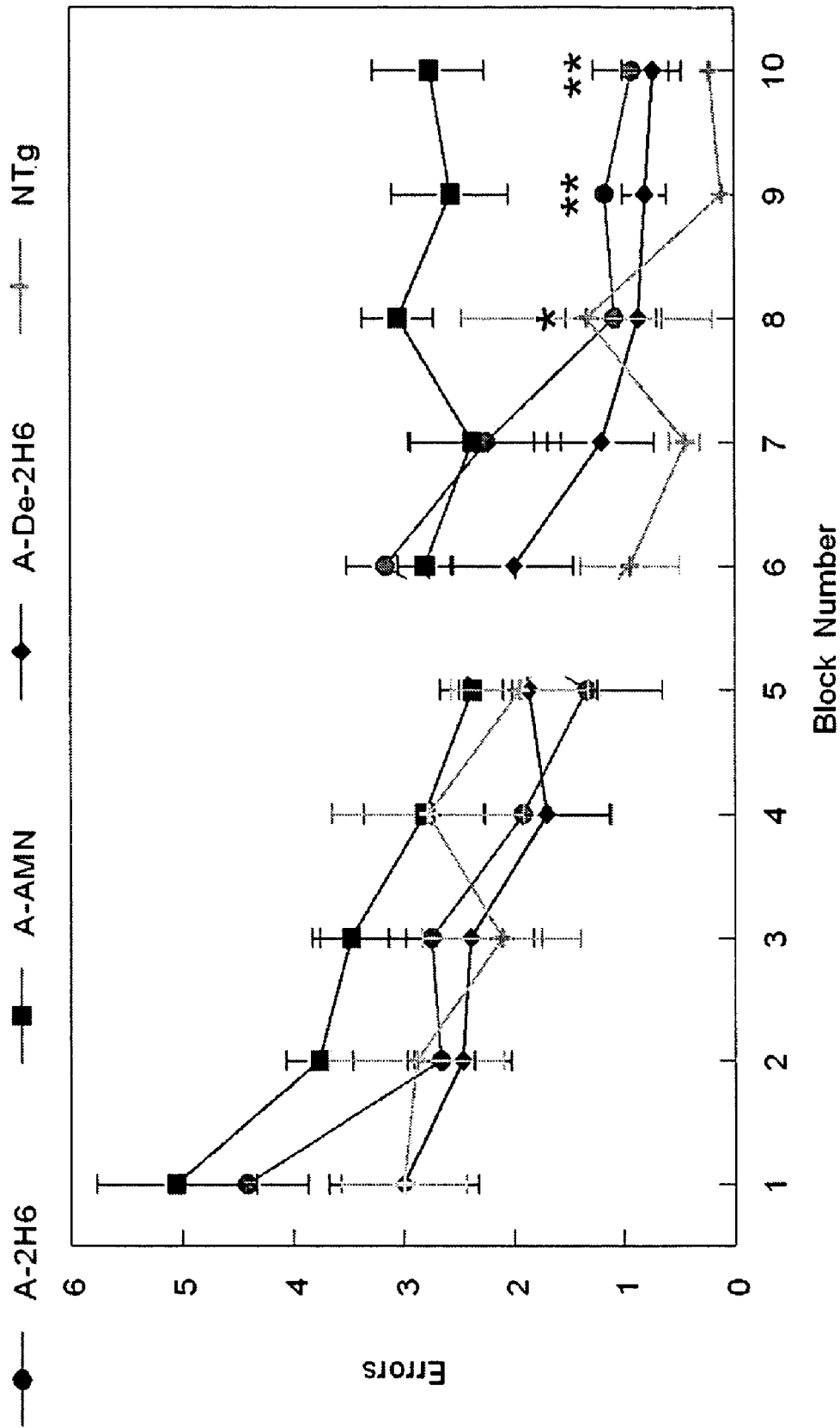

FIG. 5 is a graph showing spatial learning deficits in APP-transgenic mice were reversed following 16 weeks of antibody treatment with 2H6 and deglycosylated 2H6. Mice were tested in a two-day version of the radial-arm water maze. Y axis represents mean number of errors made over the 2-day trial period. Block numbers 1-5 represent tests in day 1; and block numbers 6-10 represent tests in day 2. "*" indicates p<0.05 for both 2H6 (A-2H6) and deglycosylated 2H6 (A-De-2H6) treated mice when compared with anti-AMN antibody treated mice (A-AMN). "**" indicates p<0.01 for both 2H6 (A-2H6) and deglycosylated 2H6 (A-De-2H6) treated mice when compared with anti-AMN antibody treated mice (A-AMN).

FIGS. 6A and 6B are graphs showing decreases of parenchymal Congo-red stained amyloid-beta peptide in hippocampus (FIG. 6B) and frontal cortex (FIG. 6A) after 16 weeks of antibody treatment with 2H6, anti-AMN (referred to as AMN), and deglycosylated 2H6 (referred to as D-2H6) antibody. Y-axes in FIGS. 6A and 6B represent mean of percent area positive for Congo-red staining. X-axes in FIGS. 6A and 6B represent type of antibody administered.

FIGS. 7A and 7B are graphs showing increases of vascular Congo-red stained amyloid-beta peptide in hippocampus (FIG. 7A) and frontal cortex (FIG. 7B) after 16 weeks of antibody treatment with 2H6, anti-AMN (referred to as AMN), and deglycosylated 2H6 (referred to as D-2H6) antibody. Y-axes in FIGS. 7A and 7B represent mean of percent area positive for Congo-red staining. X-axes in FIGS. 7A and 7B represent type of antibody administered.

Figure 8:
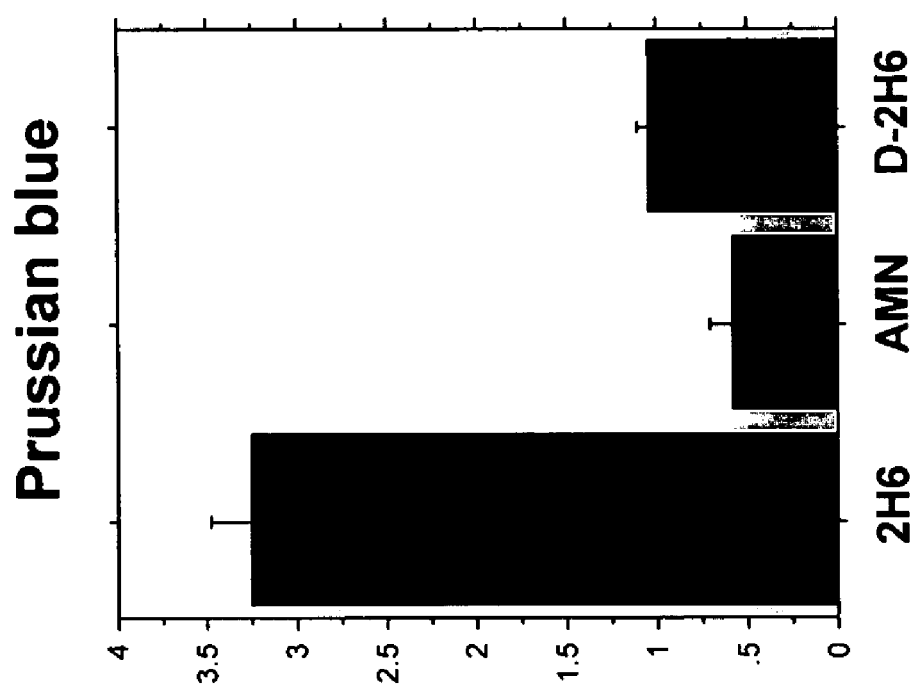

FIG. 8 is a graph showing number of Prussian blue positive profiles after 16 weeks of antibody treatment with 2H6, anti-AMN (referred to as AMN), and deglycosylated 2H6 (referred to as D-2H6) antibody. Y-axis represents positive profiles per section. X-axis represents type of antibody administered.

Figure 9:
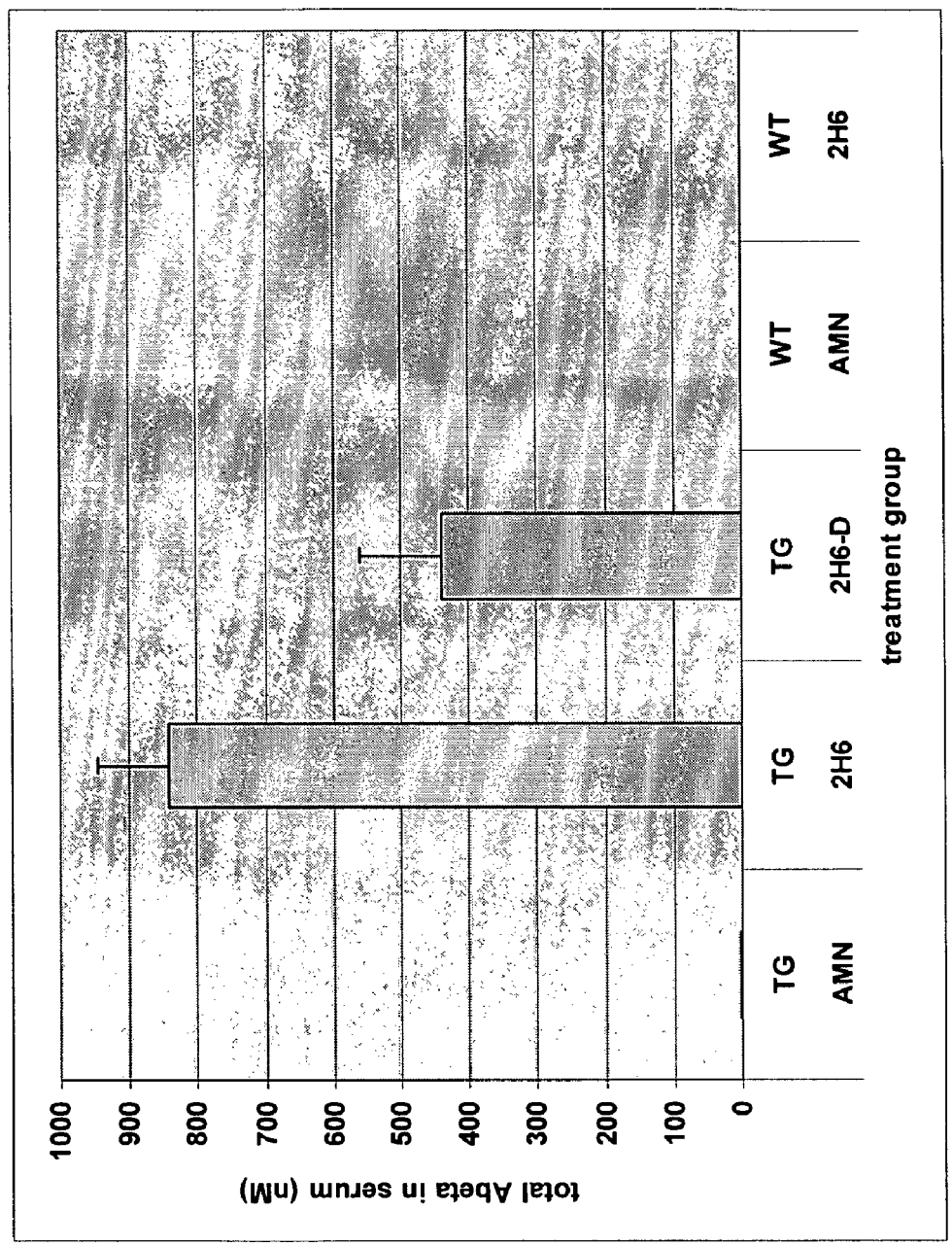

FIG. 9 is a graph showing serum level of Aβ peptide after administration of anti-AMN antibody (referred to as AMN), antibody 2H6 (referred to as 2H6), deglycosylated 2H6 (referred to as 2H6-D) in APP Tg2576 mice, and after administration of anti-AMN antibody and antibody 2H6 in wild type (WT) mice.

Figure 10:
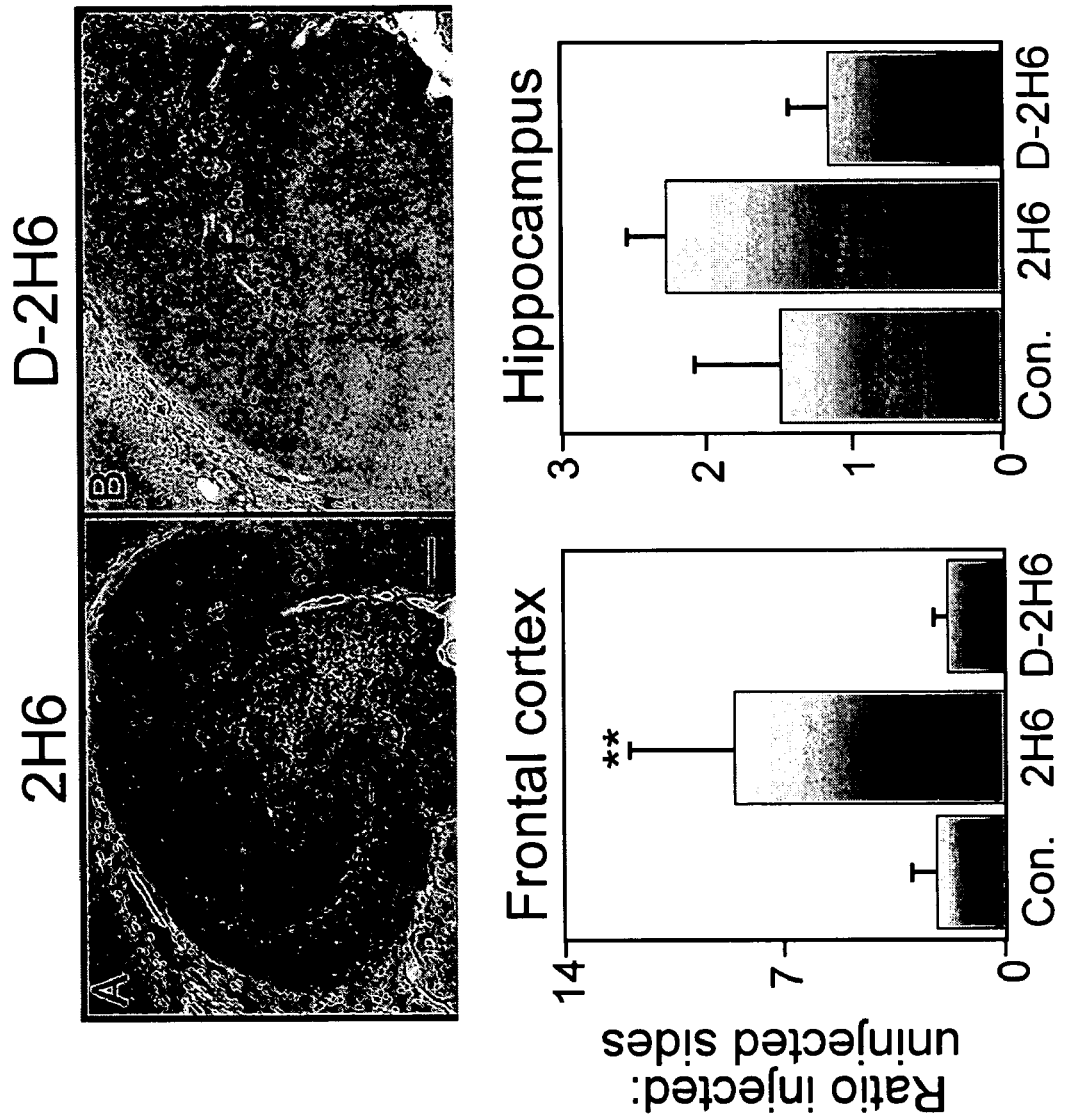

FIG. 10 shows immunostaining of CD45 in the hippocampus of a mouse after intracranial administration of 2H6 antibody (A) or deglycosylated 2H6 antibody (B). The bottom panel shows that the ratio of the average area occupied CD45 positive staining of injected side over uninjected side in the frontal cortex and hippocampus after intracranial administration of the control antibody, 2H6 antibody, or deglycosylated 2H6 antibody. "**" indicates P<0.01 as compared to the control antibody.

Figure 11:
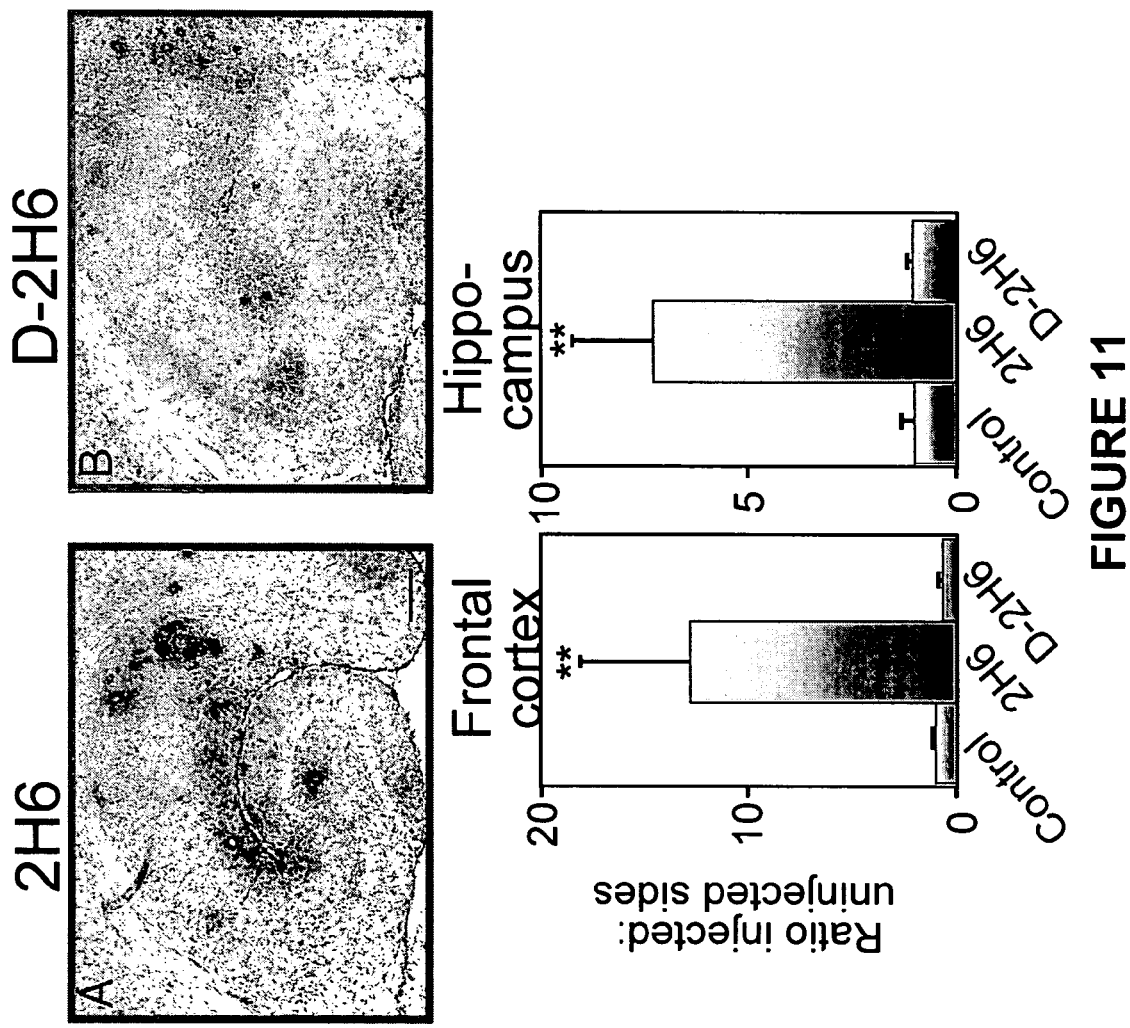

FIG. 11 shows immunostaining of Fcγ receptor in the hippocampus of a mouse after intracranial administration of 2H6 antibody (A) or deglycosylated 2H6 antibody (B). The bottom panel shows that the ratio of the average area occupied by Fcγ receptor positive staining of injected side over uninjected side in the frontal cortex and hippocampus after intracranial administration of the control antibody, 2H6 antibody, or deglycosylated 2H6 antibody. "**" indicates P<0.01 as compared to the control antibody.

Figure 12:
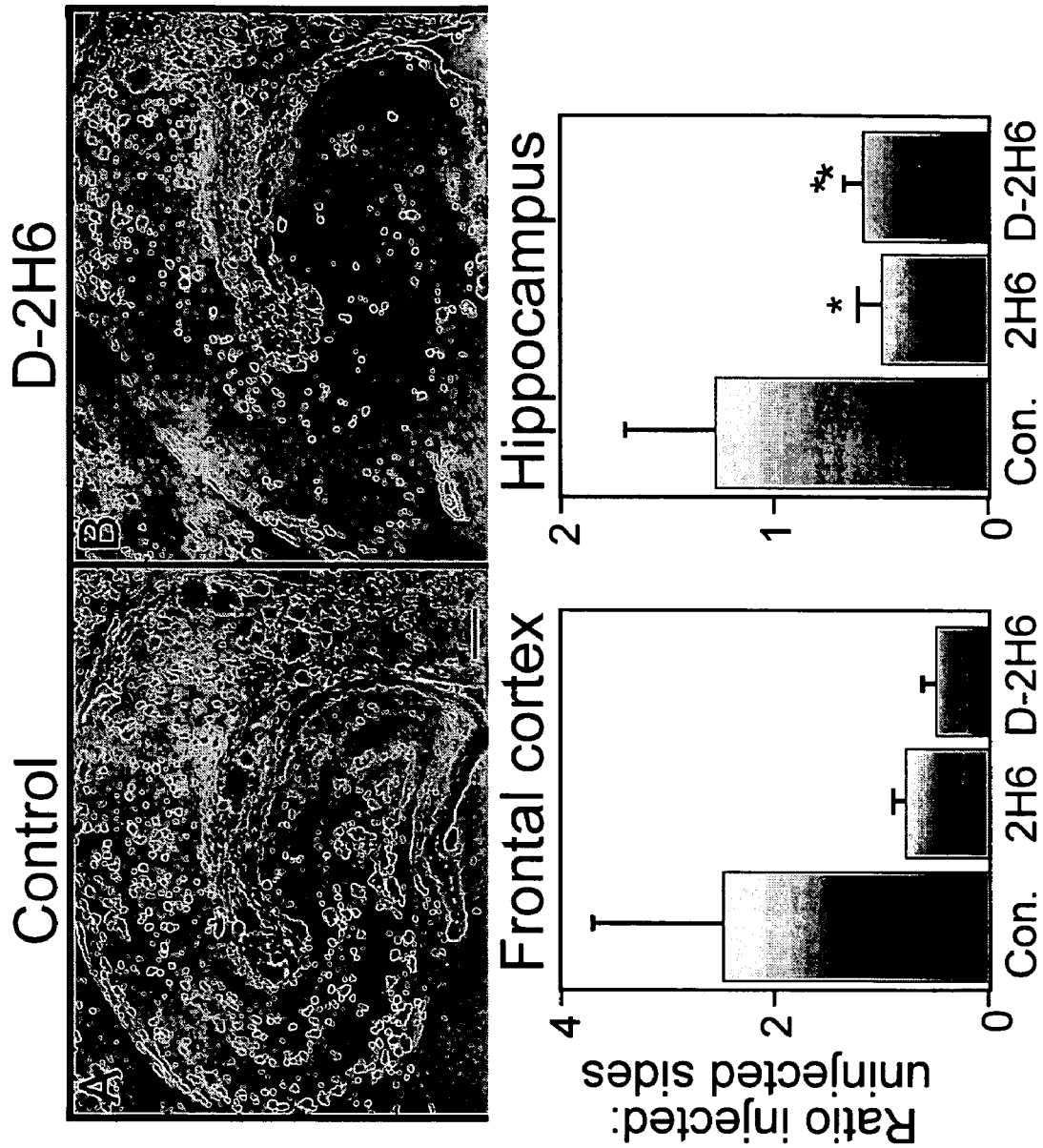

FIG. 12 shows immunostaining of Aβ peptide in the hippocampus of a mouse after intracranial administration of 2H6 antibody (A) or deglycosylated 2H6 antibody (B). The bottom panel shows that the ratio of the average area occupied by Aβ positive staining of injected side over uninjected side in the frontal cortex and hippocampus after intracranial administration of the control antibody, 2H6 antibody, or deglycosylated 2H6 antibody. "**" indicates P<0.01 as compared to the control antibody. "*" indicates P<0.05 as compared to the control antibody.

Figure 13:
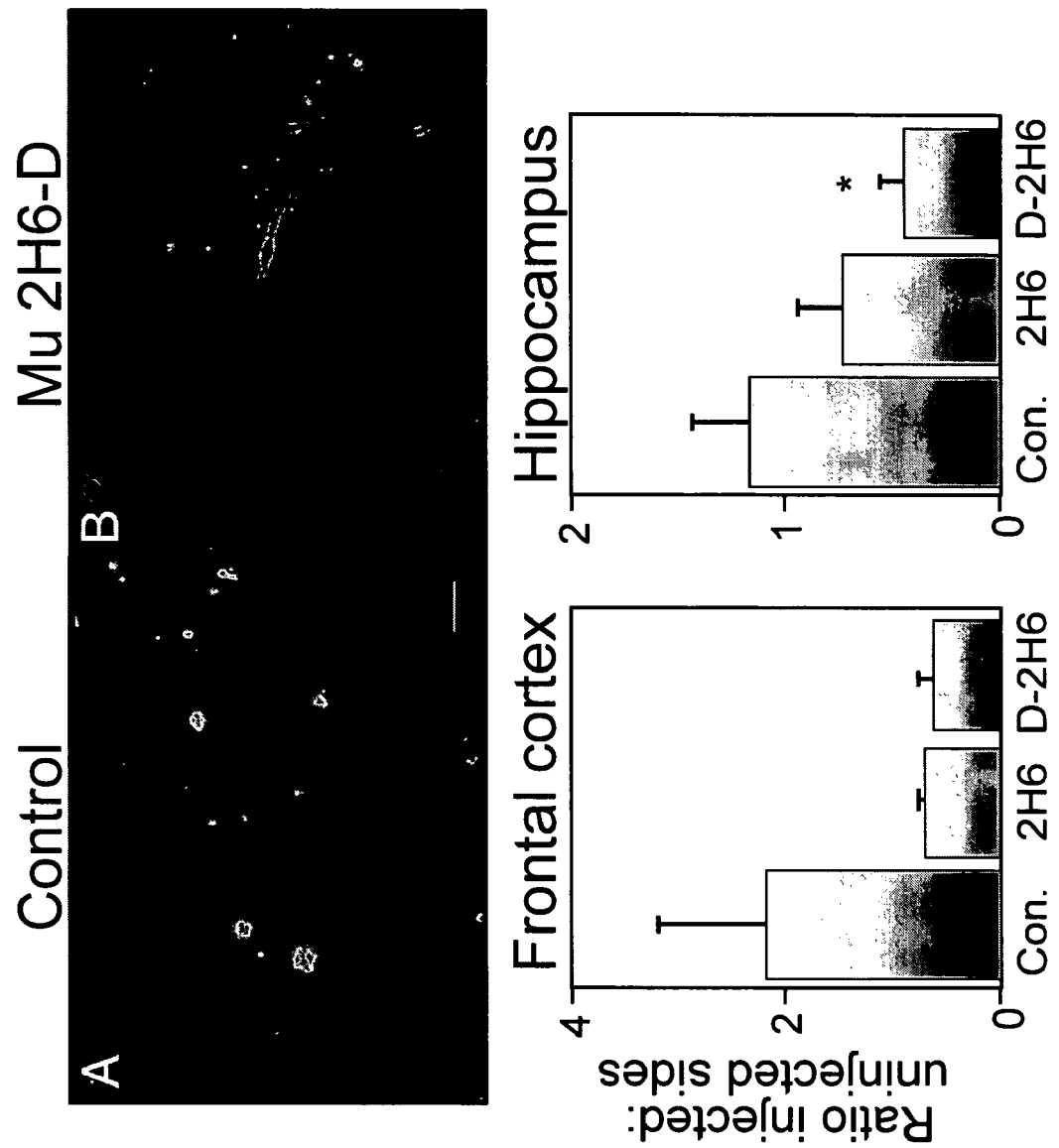

FIG. 13 shows thioflavine-S in the hippocampus of a mouse after intracranial administration of 2H6 antibody (A) or deglycosylated 2H6 antibody (B). The bottom panel shows that the ratio of the average area occupied by thioflavine-S positive staining of injected side over uninjected side in the frontal cortex and hippocampus after intracranial administration of the control antibody, 2H6 antibody, or deglycosylated 2H6 antibody. "*" indicates P<0.05 as compared to the control antibody.

FIG. 14 shows epitope mapping of antibody 2294 and 6G by ELISA. Various Aβ peptides were immobilized on ELISA plates. Antibodies were incubated for 1 hour with various immobilized peptides. Antibody 6G bound to immobilized Aβ peptides were measured using goat anti-human kappa HRP conjugated secondary antibody. Antibody 2294 bound to immobilized Aβ peptides were measured using goat anti-mouse that binds to both heavy and light chain and is HRP conjugated secondary antibody. "NB" refers to no binding detected. The numbers in the columns under "2294" and "6G" represent absorbance at 450 nm. Aβ peptides from the top to the bottom are assianed SEQ ID NOS: 41-53, respectively.

DETAILED DESCRIPTION OF THE INVENTION

The invention disclosed herein provides antibodies and polypeptides that bind to C-terminus of $A\beta_{1-40}$. These antibodies and polypeptides are derived from 9TL or its variants shown in Table 3. The invention also provides methods of making and using these antibodies. In some embodiments, the invention provides antibody 9TL, and methods of making and using this antibody. The invention also provides 9TL polypeptides (including antibodies) that bind $A\beta_{1-40}$, and polynucleotides encoding 9TL antibody and/or polypeptide.

The invention disclosed herein also provides methods for preventing and/or treating Aβ-associated diseases, such as Alzheimer's disease, Down's syndrome, Parkinson's disease, multi-infarct dementia, mild cognitive impairment, cerebral amyloid angiopathy, vascular disorder caused by deposit of Aβ peptide in blood vessels (such as stroke and HCHWA-D) in an individual by administration of a therapeutically effective amount of an antibody 9TL, or antibody or polypeptide derived from 9TL.

The invention also provides methods for treating or preventing diseases associated with β-amyloid deposit in an individual, such as Alzheimer's disease, Down's syndrome, multi-infarct dementia, mild cognitive impairment, and cerebral amyloid angiopathy in an individual by administering to the individual an effective amount of a pharmaceutical composition comprising an antibody or a polypeptide that specifically binds to a β-amyloid peptide or an aggregated form of an Aβ peptide, or a polynucleotide encoding the antibody or the polypeptide, wherein the antibody or the polypeptide has impaired effector function.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

As used herein, the terms "9TL" and "antibody 9TL" are used interchangeably to refer to an antibody produced by expression vectors having deposit numbers of ATCC PTA-6124 and ATCC PTA-6125. The amino acid sequence of the heavy chain and light chain variable regions are shown in FIG. 1. The CDR portions of antibody 9TL (including Chothia and Kabat CDRs) are diagrammatically depicted in FIG. 1. The polynucleotides encoding the heavy and light chain variable regions are shown in SEQ ID NO:9 and SEQ ID NO:10. The characterization of 9TL is described in the Examples.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an $A\beta_{1-40}$ epitope is an antibody that binds this epitope with greater affinity, avidity, more readily, and/or with greater duration than it binds to other $A\beta_{1-40}$ epitopes or non-$A\beta_{1-40}$ epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Imunological Interest, 5th Ed. Public Health Service, National Institutes of Health, Bethesda, Md., 1991. The Fc region of an immunoglobulin generally comprises two constant domains, CH2 and CH3.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, at least about 99% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, PNAS (USA), 95:652-656.

As used herein, an "effective dosage" or "effective amount" drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as inhibiting, suppressing or reducing the formation of amyloid plaques, reducing, removing, clearing amyloid plaques, improving cognition, reversing or slowing cognitive decline, sequestering or increasing soluble Aβ peptide circulating in biological fluids, decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: inhibiting, suppressing or reducing the formation of amyloid plaques, reducing, removing, or clearing amyloid plaques, improving cognition, reversing or slowing cognitive decline, sequestering soluble Aβ peptide circulating in biological fluids, reducing Aβ peptide (including soluble, oligomeric and deposited) in a tissue (such as brain), inhibiting, slowing and/or reducing accumulation of Aβ peptide in the brain, inhibiting, slowing and/or reducing toxic effects of Aβ peptide in a tissue (such as brain), decreasing symptoms resulting from the disease, increasing the quality of life of those suffering from the disease, decreasing the dose of other medications required to treat the disease, delaying the progression of the disease, and/or prolonging survival of patients.

As used herein, "delaying" development of Alzheimer's disease means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of Alzheimer's disease is a method that reduces probability of disease development in a given time frame and/or reduces extent of the disease in a given time frame, when compared to not using the method. Such comparisons are typically based on clinical studies, using a statistically significant number of subjects.

"Development" of Alzheimer's disease means the onset and/or progression of Alzheimer's disease within an individual. Alzheimer's disease development can be detectable using standard clinical techniques as described herein. However, development also refers to disease progression that may be initially undetectable. For purposes of this invention, progression refers to the biological course of the disease state, in this case, as determined by a standard neurological examination, patient interview, or may be determined by more specialized testing. A variety of these diagnostic tests include, but not limited to, neuroimaging, detecting alterations of levels of specific proteins in the serum or cerebrospinal fluid (e.g., amyloid peptides and Tau), computerized tomography (CT), and magnetic resonance imaging (MRI). "Development" includes occurrence, recurrence, and onset. As used herein "onset" or "occurrence" of Alzheimer's disease includes initial onset and and/or recurrence.

As used herein, administration "in conjunction" includes simultaneous administration and/or administration at different times. Administration in conjunction also encompasses administration as a co-formulation or administration as separate compositions. As used herein, administration in conjunction is meant to encompass any circumstance wherein an anti-Aβ antibody and another agent are administered to an individual, which can occur simultaneously and/or separately. As further discussed herein, it is understood that an anti-Aβ antibody and the other agent can be administered at different dosing frequencies or intervals. For example, an anti-Aβ antibody can be administered weekly, while the other agent can be administered less frequently. It is understood that the anti-Aβ antibody and the other agent can be administered using the same route of administration or different routes of administration.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes: cells in culture, cell supernatants, cell lysates, serum, plasma, biological fluid, and tissue samples.

An "individual" (alternatively referred to as a "subject") is a mammal, more preferably a human. Mammals also include, but are not limited to, farm animals (such as cows), sport animals, pets (such as cats, dogs, horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000).

The term "$k_{on}$", as used herein, is intended to refer to the on rate constant for association of an antibody to an antigen.

The term "$k_{off}$", as used herein, is intended to refer to the off rate constant for dissociation of an antibody from the antibody/antigen complex.

The term "$K_D$", as used herein, is intended to refer to the equilibrium dissociation constant of an antibody-antigen interaction.

Compositions and Methods of Making the Compositions

Antibody 9TL and 9TL Derived Antibodies and Polypeptides

This invention encompasses compositions, including pharmaceutical compositions, comprising antibody 9TL and its variants shown in Table 3 or polypeptide derived from antibody 9TL and its variants shown in Table 3; and polynucleotides comprising sequences encoding 9TL antibody and its variants or the polypeptide. As used herein, compositions comprise one or more antibodies or polypeptides (which may or may not be an antibody) that bind to C-terminus of $A\beta_{1-40}$, and/or one or more polynucleotides comprising sequences encoding one or more antibodies or polypeptides that bind to C-terminus of $A\beta_{1-40}$. These compositions may further comprise suitable excipients, such as pharmaceutically acceptable excipients including buffers, which are well known in the art.

The antibodies and polypeptides of the invention are characterized by any (one or more) of the following characteristics: (a) binds to C-terminal peptide 28-40 of of $A\beta_{1-40}$, but does not significantly bind to Aβ1-42 or Aβ1-43; (b) binds to C-terminal peptide 33-40 of $A\beta_{1-40}$; (c) suppresses formation of amyloid plaques in a subject; (d) reduces amyloid plaques in a subject; (e) treats, prevents, ameliorates one or more symptoms of Alzheimer's disease; (f) improves cognitive function. The antibodies and polypeptides of the invention may also exhibit a desirable safety profile in contrast to other reported anti-Aβ antibodies. For example, the compositions of the invention may not cause significant or unacceptable levels of any one or more of: bleeding in the brain vasculature (cerebral hemorrhage); meningoencephalitis (including changing magnetic resonance scan); elevated white blood count in cerebral spinal fluid; central nervous system inflammation.

Accordingly, the invention provides any of the following, or compositions (including pharmaceutical compositions) comprising any of the following: (a) antibody 9TL or its variants shown in Table 3; (b) a fragment or a region of antibody 9TL or its variants shown in Table 3; (c) a light chain of antibody 9TL or its variants shown in Table 3; (d) a heavy chain of antibody 9TL or its variants shown in Table 3; (e) one or more variable region(s) from a light chain and/or a heavy chain of antibody 9TL or its variants shown in Table 3; (f) one or more CDR(s) (one, two, three, four, five or six CDRs) of antibody 9TL or its variants shown in Table 3; (g) CDR H3 from the heavy chain of antibody 9TL; (h) CDR L3 from the light chain of antibody 9TL or its variants shown in Table 3; (i) three CDRs from the light chain of antibody 9TL or its variants shown in Table 3; (j) three CDRs from the heavy chain of antibody 9TL or its variants shown in Table 3; (k) three CDRs from the light chain and three CDRs from the heavy chain, of antibody 9TL or its variants shown in Table 3; and (l) an antibody comprising any one of (b) through (k). The invention also provides polypeptides comprising any one or more of the above.

The CDR portions of antibody 9TL (including Chothia and Kabat CDRS) are diagrammatically depicted in FIG. 1. Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

In some embodiments, the invention provides a polypeptide (which may or may not be an antibody) which comprises at least one CDR, at least two, at least three, or at least four, at least five, or all six CDRs that are substantially identical to at least one CDR, at least two, at least three, at least four, at least five or all six CDRs of 9TL or its variants shown in Table 3. Other embodiments include antibodies which have at least two, three, four, five, or six CDR(s) that are substantially identical to at least two, three, four, five or six CDRs of 9TL or derived from 9TL. In some embodiments, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of 9TL or its variants shown in Table 3. It is understood that, for purposes of this invention, binding specificity and/or overall activity is generally retained, although the extent of activity may vary compared to 9TL or its variants shown in Table 3 (may be greater or lesser).

The invention also provides a polypeptide (which may or may not be an antibody) which comprises an amino acid sequence of 9TL or its variants shown in Table 3 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of 9TL or its variants shown in Table 3, wherein at least 3 of the amino acids are from a variable region of 9TL (FIG. 1) or its variants shown in Table 3. In one embodiment, the variable region is from a light chain of 9TL. In another embodiment, the variable region is from a heavy chain of 9TL. An exemplary polypeptide has contiguous amino acid (lengths described above) from both the heavy and light chain variable regions of 9TL. In another embodiment, the 5 (or more) contiguous amino acids are from a complementarity determining region (CDR) of 9TL shown in FIG. 1. In some embodiments, the contiguous amino acids are from a variable region of 9TL.

The binding affinities of the antibodies and polypeptides of the invention may vary, and need not be (but can be) a particular value or range, as the exemplary embodiments described below. The binding affinity of the antibodies and polypeptides of the invention to $A\beta_{1-40}$ can be about 0.10 to about 0.80 nM, about 0.15 to about 0.75 nM and about 0.18 to about 0.72 nM. In some embodiments, the binding affinity is about 2 pM, about 5 pM, about 10 pM, about 15 pM, about 20 pM, about 40 pM, or greater than about 40 pM. In one embodiment, the binding affinity is between about 2 pM and 22 pM. In other embodiments, the binding affinity is less than about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 0.30 pM, about 10 pM. In some embodiment, the binding affinity is about 10 nM. In other embodiments, the binding affinity is less than about 10 nM, less than about 50 nM, less than about 100 nM, less than about 150 nM, less than about 200 nM, less than about 250 nM, less than about 500 nM, or less than about 1000 nM. In other embodiments, the binding affinity is less than about 5 nM. In other embodiments, the binding affinity is less than about 1 nM. In other embodiments, the binding affinity is about 0.1 nM or about 0.07 nM. In other embodiments, the binding affinity is less than about 0.1 nM or less than about 0.07 nM. In other embodiments, the binding affinity is from any of about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM to any of about 2 pM, about 5 pM, about 10 pM, about 15 pM, about 20 pM, or about 40 pM. In some embodiments, the binding affinity is any of about 10 nM, about 5 nM, about 1 nM, about 900 pM, about 800 pM, bout 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In still other embodiments, the binding affinity is about 2 pM, about 5 pM, about 10 pM, about 15 pM, about 20 pM, about 40 pM, or greater than about 40 pM.

The invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody 9TL shown in SEQ ID NO:9 and SEQ ID NO:10. In another embodiment, the polynucleotide comprising the nucleotide sequence shown in SEQ ID NO:9 and SEQ ID NO:10 are cloned into one or more vectors for expression or propagation. The sequence encoding the antibody of interest may be maintained in a vector in a host cell and the host cell can then be expanded and frozen for future use. Vectors (including expression vectors) and host cells are further described herein.

The invention also encompasses single chain variable region fragments ("scFv") of antibodies of this invention, such as 9TL. Single chain variable region fragments are made by linking light and/or heavy chain variable regions by using a short linking peptide. Bird et al. (1988) Science 242:423-426. An example of a linking peptide is (GGGGS)$_3$ (SEQ ID NO:40) which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibody 9TL or one or more CDRs derived from antibody 9TL can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

In the recombinant humanized antibodies, the Fc portion can be modified to avoid interaction with Fcγ receptor and the complement immune system. This type of modification was designed by Dr. Mike Clark from the Department of Pathology at Cambridge University, and techniques for preparation of such antibodies are described in WO 99/58572, published Nov. 18, 1999.

For example, the constant region may be engineered to more resemble human constant regions to avoid immune response if the antibody for use in clinical trials and treatments in humans. See, for example, U.S. Pat. Nos. 5,997,867 and 5,866,692.

The invention encompasses modifications to antibody 9TL, including functionally equivalent antibodies which do not significantly affect their properties and variants which have enhanced or decreased activity and/or affinity. For example, the amino acid sequence of antibody 9TL may be mutated to obtain an antibody with the desired binding affinity to Aβ$_{1-40}$ peptide. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) Non-polar: Norleucine, Met, Ala, Val, Leu, Ile;
  (2) Polar without charge: Cys, Ser, Thr, Asn, Gln;
  (3) Acidic (negatively charged): Asp, Glu;
  (4) Basic (positively charged): Lys, Arg;
  (5) Residues that influence chain orientation: Gly, Pro; and
  (6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of $\beta(1,4)$-N-acetyl-glucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H), N-glycosidase F as described in Example 3, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified 9TL polypeptides are made using established procedures in the art and can be screened using standard assays known in the art, some of which are described below and in the Examples.

In some embodiments of the invention, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., *Immunology* 86:319-324 (1995); Lund et al., *J. Immunology* 157:4963-9 157:4963-4969 (1996); Idusogie et al., *J. Immunology* 0.164:4178-4184 (2000); Tao et al., *J. Immunology* 143: 2595-2601 (1989); and Jefferis et al., *Immunological Reviews* 163:59-76 (1998). In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2a constant region comprising the following mutations: A330P331 to S330S331 (amino acid numbering with reference to the wildtype IgG2a sequence). Eur. J. Immunol. (1999) 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., *J. Immunology* 143: 2595-2601 (1989); and Jefferis et al., *Immunological Reviews* 163:59-76 (1998). In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified. Methods for determining binding affinity are well-known in the art. Binding affinity may be determined using BIAcore surface plasmon resonance analysis, which detects differences in binding affinity of about 2-fold or greater. BIAcore is particularly useful when the starting antibody already binds with a relatively high affinity, for example a $K_D$ of about 10 nM or lower. Screening using BIAcore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., (1993) Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acid (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using BIAcore surface plasmon resonance analysis, and selection using any method known in the art for selection, including phage display, yeast display, and ribosome display.

The invention also encompasses fusion proteins comprising one or more fragments or regions from the antibodies (such as 9TL) or polypeptides of this invention. In one embodiment, a fusion polypeptide is provided that comprises at least 10 contiguous amino acids of the variable light chain region shown in SEQ ID NO:2 (FIG. 1) and/or at least 10 amino acids of the variable heavy chain region shown in SEQ ID NO:1 (FIG. 1). In other embodiments, a fusion polypeptide is provided that comprises at least about 10, at least about 15, at least about 20, at least about 25, or at least about 30 contiguous amino acids of the variable light chain region shown in SEQ ID NO:2 (FIG. 1) and/or at least about 10, at least about 15, at least about 20, at least about 25, or at least about 30 contiguous amino acids of the variable heavy chain region shown in SEQ ID NO:1 (FIG. 1). In another embodiment, the fusion polypeptide comprises a light chain variable region and/or a heavy chain variable region of 9TL, as shown in SEQ ID NO:2 and SEQ ID NO:1 of FIG. 1. In another embodiment, the fusion polypeptide comprises one or more CDR(s) of 9TL. In still other embodiments, the fusion polypeptide comprises CDR H3 and/or CDR L3 of antibody 9TL. For purposes of this invention, an 9TL fusion protein contains one or more 9TL antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A 9TL fusion polypeptide can be created by methods known in the art, for example, synthetically or recombinantly. Typically, the 9TL fusion proteins of this invention are made by preparing an expressing a polynucleotide encoding them using recombinant methods described herein, although they may also be prepared by other means known in the art, including, for example, chemical synthesis.

This invention also provides compositions comprising 9TL antibodies or polypeptides conjugated (for example, linked) to an agent that facilitate coupling to a solid support (such as biotin or avidin). For simplicity, reference will be made generally to 9TL or antibodies with the understanding that these methods apply to any of the $A\beta_{1-40}$ binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent (alternatively termed "label") such as a fluorescent molecule, a radioactive molecule or any others labels known in the art. Labels are known in the art which generally provide (either directly or indirectly) a signal.

The invention also provides compositions (including pharmaceutical compositions) and kits comprising antibody 9TL, and, as this disclosure makes clear, any or all of the antibodies and/or polypeptides described herein.

Anti-Aβ Peptide Antibodies and Polypeptides Having Impaired Effector Function

The methods of the invention use antibodies or polypeptides (including pharmaceutical compositions comprising the antibodies or polypeptides) that specifically bind to a beta-amyloid peptide and have impaired effector function. The antibodies and polypeptides are further characterized by any (one or more) of the following characteristics: (a) suppresses formation of amyloid plaques in a subject; (b) reduces amyloid plaques in a subject; (c) treats, prevents, ameliorates one or more symptoms of Alzheimer's disease; (d) improves cognitive function. The antibodies and polypeptides described herein may exhibit a desirable safety profile, for example, the compositions of the invention do not cause significant or unacceptable levels or have a reduced level of any one or more of: bleeding in the brain vasculature (cerebral hemorrhage); meningoencephalitis (including changing magnetic resonance scan); elevated white blood count in cerebral spinal fluid; central nervous system inflammation. As shown in Example 4, an anti-Aβ antibody having N-linked glycosylation removed in the Fc region was effective in removing amyloid plaques in the brain and improving cognitive function with significantly less microhemorrhage than the intact antibody in an animal model for Alzheimer's disease.

As used herein, an antibody or a polypeptide having an "impaired effector function" (used interchangeably with "immunologically inert" or "partially immunologically inert") refers to antibodies or polypeptides that do not have any effector function or have reduced activity or activities of effector function (compared to antibody or polypeptide having an unmodified or a naturally occurring constant region), e.g., having no activity or reduced activity in any one or more of the following: a) triggering complement mediated lysis; b) stimulating antibody-dependent cell mediated cytotoxicity (ADCC); and c) activating microglia. The effector function activity may be reduced by about any of 10%, 20%, 30%, 40%, 50%, 60%, 70%, 80%, 90%, 95%, 99%, and 100%. In some embodiments, the antibody binds to a beta-amyloid peptide without triggering significant complement dependent lysis, or cell mediated destruction of the target. For example, the Fc receptor binding site on the constant region may be modified or mutated to remove or reduce binding affinity to certain Fc receptors, such as FcγRI, FcγRII, and/or FcγRIII. For simplicity, reference will be made to antibodies with the understanding that embodiments also apply to polypeptides. EU numbering system (Kabat et al., Sequences of Proteins of Immunological Interest; 5th ed. Public Health Service, National Institutes of Healthy, Bethesda, Md., 1991) is used to indicate which amino acid residue(s) of the constant region (e.g., of an IgG antibody) are altered or mutated. The numbering may be used for a specific type of antibody (e.g., IgG1) or a species (e.g., human) with the understanding that similar changes can be made across types of antibodies and species.

In some embodiments, the antibody that specifically binds to the an Aβ peptide comprises a heavy chain constant region having impaired effector function. The heavy chain constant region may have naturally occurring sequence or is a variant. In some embodiments, the amino acid sequence of a naturally occurring heavy chain constant region is mutated, e.g., by amino acid substitution, insertion and/or deletion, whereby the effector function of the constant region is impaired. In some embodiments, the N-glycosylation of the Fc region of a heavy chain constant region may also be changed, e.g., may be removed completely or partially, whereby the effector function of the constant region is impaired.

In some embodiments, the effector function is impaired by removing N-glycosylation of the Fc region (e.g., in the CH 2 domain of IgG) of the anti-Aβ peptide. In some embodiments, N-glycosylation of the Fc region is removed by mutating the glycosylated amino acid residue or flanking residues that are part of the glycosylation recognition sequence in the constant region. The tripeptide sequences asparagine-X-serine (N-X-S), asparagine-X-threonine (N-X-T) and asparagine-X-cysteine (N-X-C), where X is any amino acid except proline, are the recognition sequences for enzymatic attachment of the carbohydrate moiety to the asparagine side chain for N-glycosylation. Mutating any of the amino acid in the tripeptide sequences in the constant region yields an aglycosylated IgG. For example, N-glycosylation site N297 of human IgG1 and IgG3 may be mutated to A, D, Q, K, or H. See, Tao et al., *J. Immunology* 143: 2595-2601 (1989); and Jefferis et al., *Immunological Reviews* 163:59-76 (1998). It has been reported that human IgG1 and IgG3 with substitution of Asn-297 with Gln, His, or Lys do not bind to the human FcγRI and do not activate complement with C1q binding ability completely lost for IgG1 and dramatically decreased for IgG3. In some embodiments, the amino acid N in the tripeptide sequences is mutated to any one of amino acid A, C, D, E, F, G, H, I, K, L, M, P, Q, R, S, T, V, W, Y. In some embodiments, the amino acid N in the tripeptide sequences is mutated to a conservative substitution. In some embodiments, the amino acid X in the tripeptide sequences is mutated to proline. In some embodiments, the amino acid S in the tripeptide sequences is mutated to A, D, E, F, G, H, I, K, L, M, N, P, Q, R, V, W, Y. In some embodiments, the amino acid T in the tripeptide sequences is mutated to A, D, E, F, G, H, I, K, L, M, N, P, Q, R, V, W, Y. In some embodiments, the amino acid C in the tripeptide sequences is mutated to A, D, E, F, G, H, I, K, L, M, N, P, Q, R, V, W, Y. In some embodiments, the amino acid following the tripeptide is mutated to P. In some embodiments, the N-glycosylation in the constant region is removed enzymatically (such as N-glycosidase F as described in Example 3, endoglycosidase F1, endoglycosidase F2, endoglycosidase F3, and englycosidase H). Removing N-glycosylation may also be achieved by producing the antibody in a cell line having deficiency for N-glycosylation. Wright et al., J. Immunol. 160(7):3393-402 (1998).

In some embodiments, amino acid residue interacting with oligosaccharide attached to the N-glycosylation site of the constant region is mutated to reduce binding affinity to FcγRI. For example, F241, V264, D265 of human IgG3 may be mutated. See, Lund et al., *J. Immunology* 157:4963-4969 (1996).

In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000). Antibodies described in PCT WO 99/58572 and Armour et al. comprise, in addition to a binding domain directed at the target molecule, an effector domain having an amino acid sequence substantially homologous to all or part of a constant region of a human immunoglobulin heavy chain. These antibodies are capable of binding the target molecule without triggering significant complement dependent lysis, or cell-mediated destruction of the target. In some embodiments, the effector domain has a reduced affinity for FcγRI, FcγRIIa, and FcγRIII. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy. In some embodiments, the heavy chain constant region of the antibody is a human heavy chain IgG1 with any of the following mutations: 1) A327A330P331 to G327S330S331; 2) E233L234L235G236 to P233V234A235 with G236 deleted; 3) E233L234L235 to P233V234A235; 4) E233L234L235G236A327A330P331 to P233V234A235G327S330S331 with G236 deleted; 5) E233L234L235A327A330P331 to P233V234A235G327S330S331; and 6) N297 to A297 or any other amino acid except N. In some embodiments, the heavy chain constant region of the antibody is a human heavy chain IgG2 with the following mutations: A330P331 to S330S331. In some embodiments, the heavy chain constant region of the antibody is a human heavy chain IgG4 with any of the following mutations: E233F234L235G236 to P233V234A235 with G236 deleted; E233F234L235 to P233V234A235; and S228L235 to P228E235.

The constant region of the antibodies may also be modified to impair complement activation. For example, complement activation of IgG antibodies following binding of the C1 component of complement may be reduced by mutating amino acid residues in the constant region in a C1 binding motif (e.g., C1q binding motif). It has been reported that Ala mutation for each of D270, K322, P329, P331 of human IgG1 significantly reduced the ability of the antibody to bind to C1q and activating complement. For murine IgG2b, C1q binding motif constitutes residues E318, K320, and K322. Idusogie et al., *J. Immunology* 164:4178-4184 (2000); Duncan et al., *Nature* 322: 738-740 (1988).

C1q binding motif E318, K320, and K322 identified for murine IgG2b is believed to be common for other antibody isotypes. Duncan et al., *Nature* 322: 738-740 (1988). C1q binding activity for IgG2b can be abolished by replacing any one of the three specified residues with a residue having an inappropriate functionality on its side chain. It is not necessary to replace the ionic residues only with Ala to abolish C1q binding. It is also possible to use other alkyl-substituted non-ionic residues, such as Gly, Ile, Leu, or Val, or such aromatic non-polar residues as Phe, Tyr, Trp and Pro in place of any one of the three residues in order to abolish C1q binding. In addition, it is also be possible to use such polar non-ionic residues as Ser, Thr, Cys, and Met in place of residues 320 and 322, but not 318, in order to abolish C1q binding activity.

The invention also provides antibodies having impaired effector function wherein the antibody has a modified hinge region. Binding affinity of human IgG for its Fc receptors can be modulated by modifying the hinge region. Canfield et al., *J. Exp. Med.* 173:1483-1491 (1991); Hezareh et al., *J. Virol.* 75:12161-12168 (2001); Redpath et al., *Human Immunology* 59:720-727 (1998). Specific amino acid residues may be mutated or deleted. The modified hinge region may comprise a complete hinge region derived from an antibody of different antibody class or subclass from that of the CH1 domain. For example, the constant domain (CH1) of a class IgG antibody can be attached to a hinge region of a class IgG4 antibody. Alternatively, the new hinge region may comprise part of a natural hinge or a repeating unit in which each unit in the repeat is derived from a natural hinge region. In some embodiments, the natural hinge region is altered by converting one or more cysteine residues into a neutral residue, such as alanine, or by converting suitably placed residues into cysteine residues. U.S. Pat. No. 5,677,425. Such alterations are carried out using art recognized protein chemistry and, preferably, genetic engineering techniques and as described herein.

Polypeptides that specifically bind to an Aβ peptide and fused to a heavy chain constant region having impaired effector function may also be used for the methods described herein. In some embodiments, the polypeptide comprises a sequence derived from antibody 9TL or its variants shown in Table 3. In some embodiments, the polypeptide is derived from a single domain antibody that binds to an Aβ peptide. Single domain antibodies can be generated using methods known in the art. Omidfar et al., *Tumour Biol.* 25:296-305 (2004); Herring et al., *Trends in Biotechnology* 21:484-489 (2003).

In some embodiments, the antibody or polypeptide is not a F(ab')$_2$ fragment. In some embodiments, the antibody or polypeptide is not a Fab fragment. In some embodiments, the antibody or polypeptide is not a single chain antibody scFv. In some embodiments, the antibody or polypeptide is a PEGylated F(ab')$_2$ fragment. In some embodiments, the antibody or polypeptide is a PEGylated Fab fragment. In some embodiments, the antibody or polypeptide is a PEGylated single chain antibody scFv.

Other methods to make antibodies having impaired effector function known in the art may also be used.

Antibodies and polypeptides with modified constant regions can be tested in one or more assays to evaluate level of effector function reduction in biological activity compared to the starting antibody. For example, the ability of the antibody or polypeptide with an altered Fc region to bind complement or Fc receptors (for example, Fc receptors on microglia), or altered hinge region can be assessed using the assays disclosed herein as well as any art recognized assay. PCT WO 99/58572; Armour et al., *Molecular Immunology* 40: 585-593 (2003); Reddy et al., J. Immunology 164:1925-1933 (2000); Song et al., *Infection and Immunity* 70:5177-5184 (2002).

In some embodiments, the antibody that specifically binds to beta-amyloid peptide is a polyclonal antibody. In some embodiments, the antibody is a monoclonal antibody. In some embodiments, the antibody is a human antibody. In some embodiments, the antibody is a chimeric antibody. In some embodiments, the antibody is a humanized antibody. In some embodiments, the antibody is a primatized antibody. See, e.g., Yocum et al., *J. Rheumatol.* 25:1257-62 (1998); Bugelski et al., *Human & Experimental Toxicoloy* 19:230-243 (2000). In some embodiments, the antibody is deimmunized by mutation so that the antibody does not activate human immune system. See, e.g., Nanus, et al., *J. Urology* 170:S84-S89 (2003).

As used herein, Aβ peptide includes any fragments of the enzymatic cleavage products of amyloid precursor protein. For example, Aβ peptide includes any fragments of $A\beta_{1-40}$, $A\beta_{1-42}$, or $A\beta_{1-43}$; and peptides which are truncated with various number of amino acids at the N-terminus or the C-terminus of $A\beta_{1-40}$, $A\beta_{1-42}$, or $A\beta_{1-43}$. Amino acid numbering used herein is based on the numbering for Aβ1-43 (SEQ ID NO:17).

In some embodiments, the antibody or polypeptide specifically binds to an epitope within residues 1-16 of Aβ peptide. In some embodiments, the antibody or polypeptide specifically binds to an epitope within residues 16-28 of Aβ peptide. In some embodiments, the antibody or polypeptide specifically binds to an epitope within residues 28-40 of $A\beta_{1-40}$ peptide. In some embodiments, the antibody or polypeptide specifically binds to an epitope within residues 28-42 of $A\beta_{1-42}$ peptide. In some embodiments, the antibody or polypeptide specifically binds to an epitope within residues 28-43 of $A\beta_{1-43}$ peptide. In some embodiments, the antibody or polypeptide specifically binds to an Aβ peptide without binding to full-length amyloid precursor protein (APP). In some embodiments, the antibody or the polypeptide specifically binds to the aggregated form of Aβ without binding to the soluble form. In some embodiments, the antibody or the polypeptide specifically binds to the soluble form of Aβ without binding to the aggregated form. In some embodiments, the antibody or the polypeptide specifically binds to both aggregated form and soluble forms of Aβ. Antibodies that bind to various aggregated form of Aβ are known in the art, for example, antibodies that bind to amyloid beta-derived diffusible ligands (ADDLs); antibodies that bind to amyloid fibrils and/or deposit. WO 03/104437; U.S. Pub. No. 2003/0147887; U.S. Pub. No. 2004/0219146.

In some embodiments, the antibody or polypeptide comprises one, two, or three CDRs from the 3D6 immunoglobulin light chain (SEQ ID NO:2 in U.S. Pub. Nos. 2003/0165496, or 2004/0087777), and/or one, two, or three CDRs from the 3D6 immunoglobulin heavy chain (SEQ ID NO:4 in U.S. Pub. Nos. 2003/0165496, or 2004/0087777). In some embodiments, the antibody or polypeptide comprises a variable heavy chain region as set forth in SEQ ID NO:8 in U.S. Pub. No. 2003/0165496 and a variable light chain region as set forth in SEQ ID NO:5 in U.S. Pub. No. 2003/0165496. In some embodiments, the antibody or polypeptide comprises a variable heavy chain region as set forth in SEQ ID NO:12 in U.S. Pub. No. 2003/0165496 and a variable light chain region as set forth in SEQ ID NO:11 in U.S. Pub. No. 2003/0165496. In some embodiments, the antibody or polypeptide comprises one, two, or three CDRs from the 10D5 immunoglobulin light chain (SEQ ID NO:14 in U.S. Pub. Nos. 2003/0165496, or 2004/0087777), and/or one, two, or three CDRs from the 10D5 immunoglobulin heavy chain (SEQ ID NO:16 in U.S. Pub. Nos. 2003/0165496, or 2004/0087777).

In some embodiments, the antibody or polypeptide specifically binds to an epitope within residues 33-40 of A$\beta_{1-40}$. In some embodiments, the antibody or polypeptide specifically binds to an epitope on A$\beta_{1-40}$ that includes amino acid 35-40. In some embodiments, the antibody or polypeptide specifically binds to an epitope on A$\beta_{1-40}$ that includes amino acid 36-40. In some embodiments, the antibody or polypeptide specifically binds to an epitope on A$\beta_{1-40}$ that includes amino acid 39 and/or 40. In some embodiments, the antibody or polypeptide specifically binds to A$\beta_{1-40}$ but does not specifically bind to A$\beta_{1-42}$ and/or A$\beta_{1-43}$. In some embodiments, the antibody or polypeptide is antibody 9TL or an antibody or a polypeptide derived from 9TL described herein. In some embodiments, the antibody or polypeptide competitively inhibits binding of antibody 9TL and/or antibody or polypeptide derived from 9TL to A$\beta_{1-40}$. In some embodiments, the antibody is not antibody 2286 described in PCT WO 2004/032868.

The binding affinities of the antibodies and polypeptides of the invention may vary, and need not be (but can be) a particular value or range, as the exemplary embodiments described below. The binding affinity of the antibodies and polypeptides of the invention to A$\beta_{1-40}$, A$\beta_{1-40}$, or A$\beta_{1-40}$ can be about 0.10 to about 0.80 nM, about 0.15 to about 0.75 nM and about 0.18 to about 0.72 nM. In some embodiments, the binding affinity is about 2 pM, about 5 pM, about 10 pM, about 15 pM, about 20 pM, about 40 pM, or greater than about 40 pM. In one embodiment, the binding affinity is between about 2 pM and 22 pM. In other embodiments, the binding affinity is less than about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In some embodiments, the binding affinity is about 10 nM. In other embodiments, the binding affinity is less than about 10 nM, less than about 50 nM, less than about 100 mM, less than about 150 nM, less than about 200 nM, less than about 250 nM, less than about 500 nM, or less than about 1000 nM. In other embodiments, the binding affinity is less than about 5 nM. In other embodiments, the binding affinity is less than about 1 nM. In other embodiments, the binding affinity is about 0.1 nM or about 0.07 nM. In other embodiments, the binding affinity is less than about 0.1 nM or less than about 0.07 nM. In other embodiments, the binding affinity is from any of about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM to any of about 2 pM, about 5 pM, about 10 pM, about 15 pM, about 20 pM, or about 40 pM. In some embodiments, the binding affinity is any of about 10 nM, about 5 nM, about 1 nM, about 900 pM, about 800 pM, bout 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In still other embodiments, the binding affinity is about 2 pM, about 5 pM, about 10 pM, about 15 pM, about 20 pM, about 40 pM, or greater than about 40 pM.

Methods of making antibodies and polypeptides are known in the art and described herein.

Competition assays can be used to determine whether two antibodies bind the same epitope by recognizing identical or sterically overlapping epitopes or one antibody competitively inhibits binding of another antibody to the antigen. These assays are known in the art. Typically, antigen is immobilized on a multi-well plate and the ability of unlabeled antibodies to block the binding of labeled antibodies is measured. Common labels for such competition assays are radioactive labels or enzyme labels.

Antibodies and polypeptides that specifically bind to A$\beta$ can be screened for efficacy in removing amyloid deposit and other beneficial effects, such as improving cognition. For example, antibodies or polypeptides may be administered to an animal having Alzheimer's pathology. Various animal models for Alzheimer's disease are known in the art. Following administration, level of compact and diffuse amyloid plaques, behavior analysis for cognition, and microglia activation and microhemorrhage may tested using methods known in the art and described in detail in Example 2. PCT WO 2004/032868; Wilcock et al., *J. Neurosci.* 23:3745-3751 (2003); Wilcock et al., *J. Neuroinflammation* 1:24 (2004).

Polynucleotides, Vectors and Host Cells

The invention also provides isolated polynucleotides encoding the antibodies and polypeptides of the invention (including an antibody comprising the polypeptide sequences of the light chain and heavy chain variable regions shown in FIG. 1), and vectors and host cells comprising the polynucleotide.

Accordingly, the invention provides polynucleotides (or compositions, including pharmaceutical compositions), comprising polynucleotides encoding any of the following: (a) antibody 9TL or its variants shown in Table 3; (b) a fragment or a region of antibody 9TL or its variants shown in Table 3; (c) a light chain of antibody 9TL or its variants shown in Table 3; (d) a heavy chain of antibody 9TL or its variants shown in Table 3; (e) one or more variable region(s) from a light chain and/or a heavy chain of antibody 9TL or its variants shown in Table 3; (f) one or more CDR(s) (one, two, three, four, five or six CDRs) of antibody 9TL or its variants shown in Table 3; (g) CDR H3 from the heavy chain of antibody 9TL; (h) CDR L3 from the light chain of antibody 9TL or its variants shown in Table 3; (i) three CDRs from the light chain of antibody 9TL or its variants shown in Table 3; (j) three CDRs from the heavy chain of antibody 9TL or its variants shown in Table 3; (k) three CDRs from the light chain and three CDRs from the heavy chain, of antibody 9TL or its variants shown in Table 3; and (l) an antibody comprising any one of (b) through (k). In some embodiments, the polynucleotide comprises either or both of the polynucleotide(s) shown in SEQ ID NO:9 and SEQ ID NO:10.

In another aspect, the invention provides polynucleotides encoding any of the antibodies (including antibody fragments) and polypeptides described herein, such as antibodies and polypeptides having impaired effector function. Polynucleotides can be made by procedures known in the art.

In another aspect, the invention provides compositions (such as a pharmaceutical compositions) comprising any of the polynucleotides of the invention. In some embodiments, the composition comprises an expression vector comprising a polynucleotide encoding the 9TL antibody as described herein. In other embodiment, the composition comprises an expression vector comprising a polynucleotide encoding any of the antibodies or polypeptides described herein. In still other embodiments, the composition comprises either or both of the polynucleotides shown in SEQ ID NO:9 and SEQ ID NO:10. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to $A\beta_{1-40}$ is effected by an immunoassay or FACS. A cell overexpressing the antibody or protein of interest can be identified.

Diagnostic Uses of 9TL Derived Antibodies and Anti-Aβ Antibodies Having Impaired Effector Function Antibody 9TL which binds to C-terminus of $A\beta_{1-40}$ may be used to identify or detect the presence or absence of $A\beta_{1-40}$. For simplicity, reference will be made generally to 9TL or antibodies with the understanding that these methods apply to any of $A\beta_{1-40}$ binding embodiments (such as polypeptides) described herein. Detection generally involves contacting a biological sample with an antibody described herein that binds to $A\beta_{1-40}$ and the formation of a complex between $A\beta_{1-40}$ and an antibody (e.g., 9TL) which binds specifically to $A\beta_{1-40}$. The formation of such a complex can be in vitro or in vivo. The term "detection" as used herein includes qualitative and/or quantitative detection (measuring levels) with or without reference to a control.

Any of a variety of known methods can be used for detection, including, but not limited to, immunoassay, using antibody that binds the polypeptide, e.g. by enzyme-linked immunosorbent assay (ELISA), radioimmunoassay (RIA) and the like; and functional assay for the encoded polypeptide, e.g. binding activity or enzymatic assay. In some embodiments, the antibody is detectably labeled. Other embodiments are known in the art and described herein.

Antibodies and polypeptides of the invention can be used in the detection, diagnosis and monitoring of a disease, condition, or disorder associated with altered or aberrant Aβ or βAPP expression, such as Alzheimer's disease and Down's syndrome. Thus, in some embodiments, the invention provides methods comprises contacting a specimen (sample) of an individual suspected of having altered or aberrant Aβ expression with an antibody or polypeptide of the invention and determining whether the level of $A\beta_{1-40}$ differs from that of a control or comparison specimen. In other embodiments, the invention provides methods comprises contacting a specimen (sample) of an individual and determining level of $A\beta_{1-40}$ expression.

For diagnostic applications, the antibody may be labeled with a detectable moiety including but not limited to radioisotopes, fluorescent labels, and various enzyme-substrate labels. Methods of conjugating labels to an antibody are known in the art. In other embodiment of the invention, antibodies of the invention need not be labeled, and the presence thereof can be detected using a labeled antibody which binds to the antibodies of the invention.

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987).

The antibodies may also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized using immunoscintiography.

The antibody may also be used as staining reagent in pathology, following techniques well known in the art.

Anti-Aβ antibodies having impaired effector function may be used for measuring brain amyloid burden for diagnosis of subject at risk of or diagnosed with AD, and assessing progress of any treatment and disease stage. It has been reported that peripheral administration of a monoclonal anti-Aβ antibody results in a rapid increase in plasma Aβ and the magnitude of this increase is highly correlated with amyloid burden in the hippocampus and cortex. DeMattos et al., *Science* 295:2264-2267 (2002). In some embodiments, an anti-Aβ antibody having impaired effector function is administered to a subject, and level of Aβ in the plasma is measured, whereby an increase in plasma Aβ indicates presence and/or level of brain amyloid burden in the subject. These methods may be used to monitor effectiveness of the treatment and disease stage and to determine future dosing and frequency. Antibodies having impaired effector function may have a better safety profile and provide advantage for these diagnostic uses.

Methods of Using Anti-Aβ Antibody for Therapeutic Purposes

The antibodies (including polypeptides), polynucleotides, and pharmaceutical compositions described herein can be used in methods for treating, preventing and inhibiting the development of a disease characterized by aberrant deposition of a protein in the brain of a subject. The methods comprise administering to the subject an effective amount of an antibody that specifically binds to the protein or the protein deposit or a polynucleotide encoding the antibody, wherein the antibody has impaired effector function. For example, an antibody which specifically binds to prion protein or aggregated form of prion protein and has impaired effector function may be administered to a subject for prophylactic and/or therapeutic treatment of Prion diseases; an antibody which specifically binds to synuclein (e.g., alpha-synuclein) or aggregated form of synuclein and has impaired effector function may be administered to a subject for prophylactic and/or therapeutic treatment of Parkinson's disease.

The antibodies (including polypeptides), polynucleotides, and pharmaceutical compositions described herein can be used in methods for treating, preventing and inhibiting the development of Alzheimer's disease and other diseases associated with altered Aβ or βAPP expression, or accumulation or deposit of Aβ peptide (collectively termed "Aβ-associated diseases"), such as Down's syndrome, Parkinson's disease, multi-infarct dementia, mild cognitive impairment, cerebral amyloid angiopathy, vascular disorder caused by deposit of Aβ peptide in blood vessels (such as stroke and HCHWA-D). Such methods comprise administering the antibodies, polypeptides, or polynucleotides, or a pharmaceutical composition to the subject. In prophylactic applications, pharmaceutical compositions or medicaments are administered to a patient susceptible to, or otherwise at risk of, Alzheimer's disease (or other Aβ-associated disease) in an amount sufficient to eliminate or reduce the risk, lessen the severity, or delay the outset of the disease, including biochemical, histological and/or behavioral symptoms of the disease, its complications and intermediate pathological phenotypes presenting during development of the disease. In therapeutic applications, compositions or medicaments are administered to a patient suspected of, or already suffering from such a disease in amount sufficient to cure, or at least partially arrest, the symptoms of the disease (biochemical, histological and/or behavioral), including its complications and intermediate pathological phenotypes in development of the disease.

The invention also provides a method of delaying development of a symptom associated with Alzheimer's disease (or other Aβ-associated disease) in a subject comprising administering an effective dosage of a pharmaceutical composition comprising an antibody, a polypeptide, or a polynucleotide described herein to the subject. Symptoms associated with Alzheimer disease includes, but not limited to, abnormalities of memory, problem solving, language, calculation, visuospatial perception, judgment, and behavior.

This invention also provides methods of inhibiting or suppressing the formation of amyloid plaques and/or Aβ accumulation in a subject comprising administering an effective dose of a pharmaceutical composition comprising an antibody, a polypeptide, or a polynucleotide described herein described herein to the subject. In some embodiments, the amyloid plaques are in the brain of the subject. In some embodiments, the amyloid plaques are in the cerebral vasculature of the subject. In other embodiments, the Aβ accumulation is in the circulatory system of the subject.

This invention also provides methods of reducing amyloid plaques and/or reducing or slowing Aβ accumulation in a subject comprising administering an effective dose of a pharmaceutical composition comprising an antibody, a polypeptide, or a polynucleotide described herein to the subject. In some embodiments, the amyloid plaques are in the brain of the subject. In some embodiments, the amyloid plaques are in the cerebral vasculature of the subject. In other embodiments, the Aβ accumulation is in the circulatory system of the subject.

This invention also provides methods of removing or clearing amyloid plaques and/or Aβ accumulation in a subject comprising administering an effective dose of a pharmaceutical composition comprising an antibody, a polypeptide, or a polynucleotide described herein to the subject. In some embodiments, the amyloid plaques are in the brain of the subject. In some embodiments, the amyloid plaques are in the cerebral vasculature of the subject. In other embodiments, the Aβ accumulation is in the circulatory system of the subject.

This invention also provides methods of reducing Aβ peptide in a tissue (such as brain), inhibiting and/or reducing accumulation of Aβ peptide in a tissue (such as brain), and inhibiting and/or reducing toxic effects of Aβ peptide in a tissue (such as brain) in a subject comprising administering an effective dose of a pharmaceutical composition comprising an antibody, a polypeptide, or a polynucleotide described herein to the subject. Aβ polypeptide may be in soluble, oligomeric, or deposited form. Oligomeric form of Aβ may be composed of 2-50 Aβ polypeptides, which can be a mixture of full length 1-40 and 1-42 peptides and/or any truncated version of the these peptides.

The invention also provides methods of improving cognition or reversing cognitive decline associated with diseases associated with amyloid deposit of Aβ in a subject, such as Alzheimer's disease, comprising administering an effective dosage of a pharmaceutical composition comprising an antibody, a polypeptide, or a polynucleotide described herein to the subject.

The invention also provides methods for treating or preventing diseases associated with amyloid deposit of Aβ, comprising administering to the subject an effective dosage of a pharmaceutical composition comprising an antibody that specifically binds to a beta-amyloid peptide or an aggregated form of a beta-amyloid peptide, wherein the antibody comprises an Fc region with a variation from a naturally occurring Fc region, wherein the variation results in impaired effector function, whereby the administration of the antibody causes less cerebral microhemorrhage than administration of an antibody without the variation.

Aberrant deposition of proteins in the brain is associated with a number of disorders, some of which can also be characterized as amyloid diseases or amyloidoses, due to concurrent deposition of amyloid-forming proteins.

Amyloidoses are disorders that are characterized by extracellular deposition of protein fibrils, which form amyloid deposits. While the majority of these conditions are associated with amyloid deposition in the periphery, there are a number of amyloidoses in which central nervous system fibril deposition predominates. WO 00/72876 describes a number of central and peripheral amyloidoses.

Alzheimer's disease is the most well-known and probably the most common amyloid disease of the central nervous system. This condition is characterized by A-beta-containing plaques and neurofibrillatory tangles, as summarized elsewhere. Various forms of senile dementia are also associated with similar, but less progressive, A-beta plaque formation, as is Down's syndrome.

Aberrant deposition of endostatin (a 20 kDa C-terminal fragment of collagen XVIII) has been observed in brains of Alzheimer's patients, where it co-localizes with amyloid-beta(1-40). Deininger, M. H., et al., (2003) J. Neurosci 22(24): 10621-10626.

A variant of the amyloidogenic protein cystatin C, L68Q cystatin C, is associated with massive cerebral amyloidosis leading to brain hemorrhage and death in early adult life in a hereditary form of amyloid angiopathy (hereditary cystatin C amyloid angiopathy). A normal variant of cystatin C (wt[1] cystatin C) can be found associated with A-beta peptide as a component of amyloid plaques in Alzheimer's disease.

In studies to determine whether exogenous agents could suppress formation of dimers of cystatin C (either L68Q or wt[1] cystatin C), Nilsson and co-workers incubated antibodies directed to wt[1] cystatin C with monomeric forms of the two variant proteins in solution and observed decreased dimerization of the proteins. Nilsson, M. et al. (2004) J. Biol. Chem. 279(3): 24236-45.

Down syndrome is characterized by A-beta peptide plaque deposition, apoptotic cell death and aberrant dendritic arborization, in part due to constitutively increased expression of genes that include amyloid precursor protein (APP) and other proteins (superoxide dismutase I, and S100-beta)—all located within the Down locus. There is also aberrant expression of genes that are not linked to the Down locus (genes w/in a segment of chromosome 21)—GAP-43, nitric oxide synthase 3, neuronal thread protein, pro-apoptosis genes such as p53, Bax and LI-1 beta-converting enzyme. Expression of these non-Down locus genes correlates with proliferation of dystrophic neuritis and apoptotic cell death. de la Monte, S. M. 1999, J. Neural Transm. Suppl. 57: 1-19.

Brain deposition of amyloid plaques formed from A-beta peptide is a also a common pathologic feature in HIV-AIDS patients. Green, D. A., et al. (2005) AIDS 19(4): 407-11. Similarly, deposition of A-beta peptide-containing plaques have also been observed shortly following traumatic brain injury in humans, where A-beta co-localizes with APP and neurofilament proteins in swollen axons. Smith, D. H., et al. (2003): 98(5): 1072-7. Brains of patients with end-stage acquired immunodeficiency syndrome (AIDS) were also shown to have increased levels of ubiquitin-stained dotlike deposits (Ub-dots). Gelman, B. B., and Schuenke, K. (2004) J. Neurovirol 10(2): 98-108.

Amyloidoma is a relatively rare form of CNS amyloidosis, presenting in the form of an amyloid tumor, usually in the choroid plexus, with secondary extensions into white matter. Primary amyloidomas of the brain parenchyma comprise lesions composed of amyloid AL lambda light chain. Tabatbai, G., et al. (2005) Arch Neurol. 62(3): 477-80.

Multifocal white matter lesions have been observed in brain MRIs in patients carrying the gene(s) for the transthyretin Tyr77 (Tyr77 FAP) variant of familial amyloid polyneuropathy (FAP). Lossos, A., et al J. Eur. Neurol. 2005. 53(2): 55-9.

Familial leptomeningeal amyloidosis is associated with a genetic abnormality of the transthyretin (TTR) variant Asp18Gly (D18G). Jin, K., et al J. Neurol. Neurosurg. Psychiatry (2004) 75(10): 1463-66. The D18G variant form of TTR has been also shown to lead to CNS amyloidosis in Hungarian patients. According to one report, small molecule stabilizers of a tetrameric form of the protein may prevent amyloidogenesis. Hammarstrom, P. et al. (2003) Biochemistry 42(22): 6656-63.

Mutations in genes encoding alpha-synuclein have been found to be responsible for at least some familial forms of Parkinson's disease, where alpha-synuclein has been shown to be abnormally derivatized and to form neuronal and glial inclusions. Alpha synuclein also forms fibrils in vitro, leading to the categorization of Parkinson's disease as a brain amyloidosis. Trojanowski, J. Q. and Lee, V. M. (2003) Ann NY Acad. Sci. 991: 107-110.

Alpha-synuclein inclusions in oligodendroglia characterize multiple system atrophy (MSA). Kahle, P. M., et al. 2002. EMBO rep. 3(6): 583-8.

$PrP^{Sc}$ is aberrant form of cellular prion protein ($PrP^{C}$), a copper-binding glycoprotein attached to the cell membrane of neurons and other cells. PrP amyloid accumulation is commonly associated with PrP cerebral amyloid angiopathy (PrP-CAA), where the accumulation is in neurofibrillary tangles and vascular amyloid, and in Gerstmann-Straussler-Scheinker disease, where parenchymal amyloidosis may be present in association with spongiform degeneration of neurofibrillary tangles. Ghetti, B., et al. Clin. Lab. Med. (2003) 23(1): 65-85. $PrP^{Sc}$ deposition is also found in human spongiform encephalopathy (variant Creutzfeld-Jacob Disease). Paracrine inhibition of prion propagation by anti-PrP single-chain Fv miniantibodies has been reported. Heppner et al., J. Viol. 79:8330-8; 2005.

The following table provides a summary of examples of diseases associated with aberrant brain protein deposition and protein components for the deposit. Antibody against these components may be generated using methods known in the art and methods described herein, or antibodies known in the art.

| Condition | Protein component(s) |
| --- | --- |
| Alzheimer's disease | A-beta peptide |
| | wt[1] Cystatin C |
| | Endostatin |
| Amyloidoma | A-lambda light chain |
| Cerebral amyloid angiopathy (CAA) | 1. A-beta peptide |
| | 2. L68Q Cystatin C |
| | 3. $PrP^{Sc}$ |
| Spongiform encephalopathy (variant Creutzfeld-Jacob Disease) | $PrP^{Sc}$ |
| Familial amyloid polyneuropathy | Transthyretin variant Tyr77 |
| AIDS | 1. A-beta peptide |
| | 2. Ubiquitin |
| Traumatic brain injury | A-beta peptide |

-continued

| Condition | Protein component(s) |
|---|---|
| Familial leptomeningeal amyloidosis | Transthyretin variant Asp18Gly (D18G) |
| Parkinson's Disease | Alpha synuclein |
| Gerstmann-Straussler-Scheinker disease | PrP$^{Sc}$ |
| Down Syndrome | A-beta peptide |
| | Superoxide dismutase |
| | S100-beta |
| | GAP-43 |
| | Nitric oxide synthase 3 |
| | Neuronal thread protein |
| | P53 |
| | Bax |
| | LI-1 beta-converting enzyme |
| Multiple System Atrophy | Alpha-synuclein |

The methods described herein (including prophylaxis or therapy) can be accomplished by a single direct injection at a single time point or multiple time points to a single or multiple sites. Administration can also be nearly simultaneous to multiple sites. Frequency of administration may be determined and adjusted over the course of therapy, and is base on accomplishing desired results. In some cases, sustained continuous release formulations of antibodies (including polypeptides), polynucleotides, and pharmaceutical compositions of the invention may be appropriate. Various formulations and devices for achieving sustained release are known in the art.

Patients, subjects, or individuals include mammals, such as human, bovine, equine, canine, feline, porcine, and ovine animals. The subject is preferably a human, and may or may not be afflicted with disease or presently show symptoms. In the case of Alzheimer's disease, virtually anyone is at risk of suffering from Alzheimer's disease if he or she lives long enough. Therefore, the present methods can be administered prophylactically to the general population without the need for any assessment of the risk of the subject patient. The present methods are useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively (see Hardy (1997) Trends Neurosci. 20:154-9). Other markers of risk are mutations in the presenilin genes, PS 1 and PS2, and ApoE4, family history of AD, hypercholesterolemia or atherosclerosis. Individuals presently suffering from Alzheimer's disease can be recognized from characteristic dementia, as well as the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by ADRDA (Alzheimer's Disease and Related Disorders Association) criteria. In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by various ways known in the art over time. In the case of potential Down's syndrome patients, treatment can begin antenatally by administering therapeutic agent to the mother or shortly after birth.

The pharmaceutical composition that can be used in the above methods include, any of the antibodies, polypeptides, and/or polynucleotides described herein. In some embodiments, antibody is antibody 9TL or its variants shown in Table 3. In some embodiments, the antibody is an antibody that specifically binds to an Aβ peptide and comprises a constant region having impaired effector function.

Administration and Dosage

The antibody is preferably administered to the mammal in a carrier; preferably a pharmaceutically-acceptable carrier. Suitable carriers and their formulations are described in *Remington's Pharmaceutical Sciences,* 18th edition, A. Gennaro, ed., Mack Publishing Co., Easton, Pa., 1990; and *Remington, The Science and Practice of Pharmacy* 20th Ed. Mack Publishing, 2000. Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibody can be administered to the mammal by injection (e.g., systemic, intravenous, intraperitoneal, subcutaneous, intramuscular, intraportal, intracerebral, intracerebralventricular, and intranasal), or by other methods, such as infusion, which ensure its delivery to the bloodstream in an effective form. The antibody may also be administered by isolated perfusion techniques, such as isolated tissue perfusion, to exert local therapeutic effects. Intravenous injection is preferred.

Effective dosages and schedules for administering the antibody may be determined empirically, and making such determinations is within the skill in the art. Those skilled in the art will understand that the dosage of antibody that must be administered will vary depending on, for example, the mammal that will receive the antibody, the route of administration, the particular type of antibody used and other drugs being administered to the mammal. Guidance in selecting appropriate doses for antibody is found in the literature on therapeutic uses of antibodies, e.g., *Handbook of Monoclonal Antibodies*, Ferrone et al., eds., Noges Publications, Park Ridge, N.J., 1985, ch. 22 and pp. 303-357; Smith et al., *Antibodies in Human Diagnosis and Therapy*, Haber et al., eds., Raven Press, New York, 1977, pp. 365-389. A typical daily dosage of the antibody used alone might range from about 1 µg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 ug/kg body weight; at least about 100 µg/kg body weight; at least about 50 µg/kg body weight; at least about 10 ug/kg body weight; at least about 1 µg/kg body weight, or more, is administered. Antibodies may be administered at lower doses or less frequent at the beginning of the treatment to avoid potential side effect, such as temporary cerebral amyloid angiopathy (CAA).

In some embodiments, more than one antibody may be present. Such compositions may contain at least one, at least two, at least three, at least four, at least five different antibodies (including polypeptides) of the invention.

The antibody may also be administered to the mammal in combination with effective amounts of one or more other therapeutic agents. The antibody may be administered sequentially or concurrently with the one or more other therapeutic agents. The amounts of antibody and therapeutic agent depend, for example, on what type of drugs are used, the pathological condition being treated, and the scheduling and routes of administration but would generally be less than if each were used individually.

Following administration of antibody to the mammal, the mammal's physiological condition can be monitored in various ways well known to the skilled practitioner.

The above principles of administration and dosage can be adapted for polypeptides described herein.

A polynucleotide encoding an antibody or a polypeptide described herein may also be used for delivery and expression of the antibody or the polypeptide in a desired cell. It is apparent that an expression vector can be used to direct expression of the antibody. The expression vector can be administered systemically, intraperitoneally, intravenously, intramuscularly, subcutaneously, intrathecally, intraventricularly, orally, enterally, parenterally, intranasally, dermally, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding an antibody of the invention can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (*USA*) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0 524 968. Additional approaches are described in Philip, *Mol. Cell Biol.* (1994) 14:2411, and in Woffendin, *Proc. Natl. Acad. Sci.* (1994) 91:1581.

Kits

The invention also provides articles of manufacture and kits containing materials useful for treating pathological conditions described herein, such as Alzheimer's disease or other Aβ-associated diseases (such as Down's syndrome, Parkinson's disease, multi-infarct dementia, mild cognitive impairment, cerebral amyloid angiopathy, vascular disorder caused by deposit of Aβ peptide in blood vessels (such as stroke and HCHWA-D)), or detecting or purifying Aβ or βAPP. The article of manufacture comprises a container with a label. Suitable containers include, for example, bottles, vials, and test tubes. The containers may be formed from a variety of materials such as glass or plastic. The container holds a composition having an active agent which is effective for treating pathological conditions or for detecting or purifying Aβ or βAPP. The active agent in the composition is an antibody and preferably, comprises monoclonal antibodies specific for Aβ or βAPP. In some embodiments, the active agent comprises antibody 9TL or any antibodies or polypeptides derived from antibody 9TL. In some embodiments, the active agent comprises an anti-Aβ antibody or polypeptide having impaired effector function. In some embodiments, the anti-Aβ antibody or polypeptide comprises a heavy chain constant region, wherein the constant region has impaired effector function. The label on the container indicates that the composition is used for treating pathological conditions such as Alzheimer's disease or detecting or purifying Aβ or βAPP, and may also indicate directions for either in vivo or in vitro use, such as those described above.

The invention also provides kits comprising any of the antibodies (such as 9TL), polypeptides, polynucleotides described herein. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein (such as methods for treating Alzheimer's disease, and methods for inhibiting or reducing accumulation of Aβ peptide in the brain). In kits to be used for detecting or purifying Aβ or βAPP, the antibody is typically labeled with a detectable marker, such as, for example, a radioisotope, fluorescent compound, bioluminescent compound, a chemiluminescent compound, metal chelator or enzyme.

In some embodiments, the invention provides compositions (described herein) for use in any of the methods described herein, whether in the context of use as a medicament and/or use for manufacture of a medicament.

The following examples are provided to illustrate, but not to limit, the invention.

EXAMPLES

Example 1

Binding Affinity Determination of Antibody 9TL and its Variants

A. General Methods

The following general methods were used in this example.

Expression Vector Used in Clone Characterization

Expression of the Fab fragment of the antibodies was under control of an IPTG inducible lacZ promotor similar to that described in Barbas (2001) *Phage display: a laboratory manual*, Cold Spring Harbor, N.Y., Cold Spring Harbor Laboratory Press pg 2.10. Vector pComb3X), however, modifications included addition and expression of the following additional domains: the human Kappa light chain constant domain and the CHI constant domain of IgG2a human immunoglobulin, Ig gamma-2 chain C region, protein accession number P01859; Immunoglobulin kappa light chain (homosapiens), protein accession number CAA09181.

Small Scale Fab Preparation

Small scale expression of Fabs in 96 wells plates was carried out as follows. Starting from *E. coli* transformed with a Fab library, colonies were picked to inoculate both a master plate (agar LB+Ampicillin (50 µg/ml)+2% Glucose) and a working plate (2 ml/well, 96 well/plate containing 1.5 mL of LB+Ampicillin (50 µg/ml)+2% Glucose). Both plates were grown at 30° C. for 8-12 hours. The master plate was stored at 4° C. and the cells from the working plate were pelleted at 5000 rpm and resuspended with 1 mL of LB+Ampicillin (50 µg/ml)+1 mM IPTG to induce expression of Fabs. Cells were harvested by centrifugation after 5 h expression time at 30° C., then resuspended in 500 µL of buffer HBS-P (10 mM HEPES buffer pH 7.4, 150 mM NaCl, 0.005% P20). Lysis of HBS-P resuspended cells was attained by one cycle of freezing (−80° C.) then thawing at 37° C. Cell lysates were centrifuged at 5000 rpm for 30 min to separate cell debris from supernatants containing Fabs. The supernatants were then injected into the BIAcore plasmon resonance apparatus to obtain affinity information for each Fab. Clones expressing Fabs were rescued from the master plate to sequence the DNA and for large scale Fab production and detailed characterization as described below.

Large Scale Fab Preparation

To obtain detailed kinetic parameters, Fabs were expressed and purified from large cultures. Erlenmeyer flasks containing 200 mL of LB+Ampicillin (50 µg/ml)+2% Glucose were inoculated with 5 mL of over night culture from a selected Fab-expressing *E. coli* clone. Clones were incubated at 30° C. until an $OD_{550\ nm}$ of 1.0 was attained and then induced by replacing the media for 200 ml, of LB+Ampicillin (50 µg/ml)+1 mM IPTG. After 5 h expression time at 30° C., cells were pelleted by centrifugation, then resuspended in 10 mL PBS (pH 8). Lysis of the cells was obtained by two cycles of freeze/thaw (at −80° C. and 37° C., respectively). Supernatant of the cell lysates were loaded onto Ni-NTA superflow sepharose (Qiagen, Valencia. Calif.) columns equilibrated with PBS, pH 8, then washed with 5 column volumes of PBS, pH 8. Individual Fabs eluted in different fractions with PBS (pH 8)+300 mM Imidazol. Fractions containing Fabs were pooled and dialized in PBS, then quantified by ELISA prior to affinity characterization.

Full Antibody Preparation

For expression of full antibodies, heavy and light chain variable regions were cloned in mammalian expression vectors and transfected using lipofectamine into HEK 293 cells for transient expression. Antibodies were purified using protein A using standard methods.

Vector pDb.9TL.hFc2a is an expression vector comprising the heavy chain of the 9TL antibody, and is suitable for transient or stable expression of the heavy chain. Vector pDb.9TL.hFc2a has nucleotide sequences corresponding to the following regions: the murine cytomegalovirus promoter region (nucleotides 1-612); a synthetic intron (nucleotides 619-1507); the DHFR coding region (nucleotides 707-1267); human growth hormone signal peptide (nucleotides 1525-1602); heavy chain variable region of 9TL (nucleotides 1603-1951); human heavy chain IgG2a constant region containing the following mutations: A330P331 to S330S331 (amino acid numbering with reference to the wildtype IgG2a sequence; see Eur. J. Immunol. (1999) 29:2613-2624); SV40 late polyadenylation signal (nucleotides 2960-3203); SV40 enhancer region (nucleotides 3204-3449); phage f1 region (nucleotides 3537-4992) and beta lactamase (AmpR) coding region (nucleotides 4429-5286). Vector pDb.9TL.hFc2a was deposited at the ATCC on Jul. 20, 2004, and was assigned ATCC Accession No. PTA-6124.

Vector pEb.9TL.hK is an expression vector comprising the light chain of the 9TL antibody, and is suitable for transient expression of the light chain. Vector pEb.9TL.hK has nucleotide sequences corresponding to the following regions: the murine cytomegalovirus promoter region (nucleotides 1-612); human EF-1 intron (nucleotides 619-1142); human growth hormone signal peptide (nucleotides 1173-1150); antibody 9TL light chain variable region (nucleotides 1251-1593); human kappa chain constant region (nucleotides 1594-1914); SV40 late polyadenylation signal (nucleotides 1932-2175); SV40 enhancer region (nucleotides 2176-2421); phage f1 region (nucleotides 2509-2964) and beta lactamase (AmpR) coding region (nucleotides 3401-4258). Vector pEb.9TL.hK was deposited at the ATCC on Jul. 20, 2004, and was assigned ATCC Accession No. PTA-6125.

Biacore Assay

Affinities of 9TL monoclonal antibody were determined using the BIAcore3000™ surface plasmon resonance (SPR) system (BIAcore, INC, Piscaway N.J.). One way of determining the affinity was immobilizing of 9TL on CM5 chip and measuring binding kinetics of $A\beta_{1-40}$ peptide to the antibody. CM5 chips were activated with N-ethyl-N'-(3-dimethylaminopropyl)-carbodiimide hydrochloride (EDC) and N-hydroxysuccinimide (NHS) according to the supplier's instructions. Antibody 9TL or its variants was diluted into 10 mM sodium acetate pH 4.0 or 5.0 and injected over the activated chip at a concentration of 0.005 mg/mL. Using variable flow time across the individual chip channels, a range of antibody density was achieved: 1000-2000 or 2000-3000 response units (RU). The chip was blocked with ethanolamine. Regeneration studies showed that a solution containing 2 volumes of PIERCE elution buffer and 1 volumes of 4 M NaCl effectively removed the bound $A\beta_{1-40}$ peptide while keeping the activity of 9TL on the chip for over 200 injections. HBS-EP buffer (0.01M HEPES, pH 7.4, 0.15 M NaCl, 3 mM EDTA, 0.005% Surfactant P20) was used as running buffer for all the BIAcore assays. Serial dilutions (0.1-10× estimated $K_D$) of purified $A\beta_{1-40}$ synthetic peptide samples were injected for 1 min at 100 µL/min and dissociation times of 10 min were allowed. Kinetic association rates ($k_{on}$) and dissociation rates ($k_{off}$) were obtained simultaneously by fitting the data to a 1:1 Langmuir binding model (Karlsson, R. Roos, H. Fagerstam, L. Petersson, B. (1994). Methods Enzymology 6.99-110) using the BIAevaluation program. Equilibrium dissociation constant ($K_D$) values were calculated as $k_{off}/k_{on}$.

Alternatively, affinity was determined by immobilizing $A\beta_{1-40}$ peptide on SA chip and measuring binding kinetics of 9TL Fab and Fab of 9TL variants to the immobilized $A\beta_{1-40}$ peptide. Affinities of 9TL Fab fragment and its variants Fab fragments were determined by Surface Plasmon Resonance (SPR) system (BIAcore 3000™, BIAcore, Inc., Piscaway, N.J.). SA chips (streptavidin) were used according to the supplier's instructions. Biotinylated Aβ peptide 1-40 was diluted into HBS-EP (10 mM HEPES pH 7.4, 150 mM NaCl, 3 mM EDTA, 0.005% P20) and injected over the chip at a concentration of 0.005 mg/mL. Using variable flow time across the individual chip channels, two ranges of antigen density were achieved: 10-200 response units (RU) for detailed kinetic studies and 500-600 RU for concentration studies and screening. Regeneration studies showed that 100 mM phosphoric acid (may also be followed by a solution containing 2 volumes of 50 mM NaOH and 1 volume of 70% ethanol) effectively removed the bound Fab while keeping the activity of Aβ peptide on the chip for over 200 injections. HBS-EP buffer was used as running buffer for all the BIAcore assays. Serial dilutions (0.1-10× estimated KD) of purified Fab samples were injected for 2 min at 100 µL/min and dissociation times of 10 min were allowed. The concentrations of the Fab proteins were determined by ELISA and/or SDS-PAGE electrophoresis using a standard Fab of known concentration (determined by amino acid analysis). Kinetic association rates ($k_{on}$) and dissociation rates ($k_{off}$) were obtained simultaneously by fitting the data to a 1:1 Langmuir binding model (Karlsson, R. Roos, H. Fagerstam, L. Petersson, B. (1994). Methods Enzymology 6.99-110) using the BIAevaluation program. Equilibrium dissociation constant ($K_D$) values were calculated as $k_{off}/k_{on}$.

B. Binding Affinity of Antibody 9TL and its Variants to $A\beta_{1-40}$

The amino acid sequences of the heavy chain and light chain variable regions of antibody 9TL is shown in FIG. 1. The binding affinity of 9TL antibody to $A\beta_{1-40}$ determined using both methods of Biacore described above is shown in Table 2 below.

TABLE 2

Binding affinity of antibody 9TL and Fab fragment

| | $k_{on}$ (1/Ms) | $K_{off}$ (1/s) | $K_D$ (nM) |
|---|---|---|---|
| 9TL mAb on CM5 chip, $A\beta_{1-40}$ flowed onto it | $4.25 \times 10^5$ | $3.89 \times 10^{-4}$ | 0.9 |
| $A\beta_{1-40}$ on SA chip, 9TL Fab flowed onto it | $3.18 \times 10^5$ | $3.59 \times 10^{-4}$ | 1.13 |

The amino acid sequence of the variants of 9TL is shown in Table 3 below. All amino acid substitutions of the variants shown in Table 3 are described relative to the sequence of 9TL. The binding affinity of Fab fragment of 9TL variants are also shown in Table 3. $K_D$ and other kinetic parameters were determined by BIAcore analysis described above with $A\beta_{1-40}$ immobilized on SA chip.

TABLE 3

Amino acid sequences and kinetic data for antibody 9TL variants.

| Clone | H1 (1) | H2 | H3 | L1 | L2 | L3 | $k_{on\,(Ms^{-1})}$ (2) | $k_{off}$ $(s^{-1})$ | $K_D$ (nM) (3) |
|---|---|---|---|---|---|---|---|---|---|
| 9TL | | | | | | | $3.18 \times 10^5$ | $3.59 \times 10^{-4}$ | 1.13 |
| 22-T/I | | | | | | L102I | $3.18 \times 10^5$ | $4.60 \times 10^{-4}$ | 1.45 |
| C6 new | | | | | | L102T | $3.56 \times 10^5$ | $9.20 \times 10^{-4}$ | 2.58 |
| W1 | | | | Y31A, A34S | | L102T | $3.18 \times 10^5$ | $9.00 \times 10^{-3}$ | 28.30 |
| W8 | | | | Y31H, A34S, K35A | | L102T | $3.18 \times 10^5$ | $3.80 \times 10^{-3}$ | 11.95 |
| W5 | | | | Y31H, K35A | | L102T | $3.18 \times 10^5$ | $4.00 \times 10^{-3}$ | 12.58 |
| M1 | | | | | | L94M | $3.18 \times 10^5$ | $8.60 \times 10^{-4}$ | 2.70 |
| M2 | | | | | | L94N | $3.18 \times 10^5$ | $1.10 \times 10^{-3}$ | 3.46 |
| M3 | | | | | | L94C | $3.18 \times 10^5$ | $1.30 \times 10^{-3}$ | 4.09 |
| M4 | | | | | | L94F | $3.18 \times 10^5$ | $9.95 \times 10^{-4}$ | 3.13 |
| M5 | | | | | | L94V | $3.18 \times 10^5$ | $1.65 \times 10^{-3}$ | 5.19 |
| M6 | | | | | | L94K | $3.18 \times 10^5$ | $4.10 \times 10^{-3}$ | 12.89 |
| M7 | | | | | | L94S | $3.18 \times 10^5$ | $6.00 \times 10^{-3}$ | 18.87 |
| M8 | | | | | | L94Q | $3.18 \times 10^5$ | $6.80 \times 10^{-3}$ | 21.38 |
| M9 | | | | | | L94G | $3.18 \times 10^5$ | $7.80 \times 10^{-3}$ | 24.53 |
| M10 | | | | | | L94S | $3.18 \times 10^5$ | $8.30 \times 10^{-3}$ | 26.10 |
| M11 | | | | | | G96S | $3.18 \times 10^5$ | $2.00 \times 10^{-3}$ | 6.29 |
| M12 | | | | | | G96T | $3.18 \times 10^5$ | $3.30 \times 10^{-3}$ | 10.38 |
| M13 | | | | | | T97S | $3.18 \times 10^5$ | $3.90 \times 10^{-4}$ | 1.23 |
| M14 | | | | | | H98L | $3.18 \times 10^5$ | $1.60 \times 10^{-3}$ | 5.03 |
| M15 | | | | | | Y99P | $3.18 \times 10^5$ | $6.70 \times 10^{-4}$ | 2.11 |
| M16 | | | | | | Y99A | $3.18 \times 10^5$ | $7.00 \times 10^{-4}$ | 2.20 |
| M17 | | | | | | Y99W | $3.18 \times 10^5$ | $1.00 \times 10^{-3}$ | 3.14 |
| M18 | | | | | | Y99Q | $3.18 \times 10^5$ | $1.50 \times 10^{-3}$ | 4.72 |
| M19 | | | | | | Y99M | $3.18 \times 10^5$ | $1.70 \times 10^{-3}$ | 5.35 |

TABLE 3-continued

Amino acid sequences and kinetic data for antibody 9TL variants.

| Clone | H1 (1) | H2 | H3 | L1 | L2 | L3 | $k_{on\,(Ms^{-1})}$ (2) | $k_{off}$ $(s^{-1})$ | $K_D$ (nM) (3) |
|---|---|---|---|---|---|---|---|---|---|
| M20 | | | | | | Y99S | $3.18 \times 10^5$ | $2.00 \times 10^{-3}$ | 6.29 |
| M21 | | | | | | Y99E | $3.18 \times 10^5$ | $5.00 \times 10^{-3}$ | 15.72 |
| M22 | | | | | | V101L | $3.18 \times 10^5$ | $4.00 \times 10^{-3}$ | 12.58 |
| M23 | | | | | | V101K | $3.18 \times 10^5$ | $5.00 \times 10^{-3}$ | 15.72 |
| M24 | | | | | | V101H | $3.18 \times 10^5$ | $6.00 \times 10^{-3}$ | 18.87 |
| M25 | | | | | | V101T | $3.18 \times 10^5$ | $8.00 \times 10^{-3}$ | 25.16 |
| M26 | | | | | | V101A | $3.18 \times 10^5$ | $9.00 \times 10^{-3}$ | 28.30 |
| M27 | | | | | | V101E | $3.18 \times 10^5$ | $1.20 \times 10^{-2}$ | 37.74 |
| M28 | | | | | | V101M | $3.18 \times 10^5$ | $1.40 \times 10^{-2}$ | 44.03 |
| M29 | | | | | | L102S | $3.18 \times 10^5$ | $7.60 \times 10^{-4}$ | 2.39 |
| M30 | | | | | | L102V | $3.18 \times 10^5$ | $6.80 \times 10^{-4}$ | 2.14 |
| M31 | | L99V | | | | | $3.18 \times 10^5$ | $1.00 \times 10^{-2}$ | 31.45 |
| M32 | | L99I | | | | | $3.18 \times 10^5$ | $2.00 \times 10^{-2}$ | 62.89 |
| M33 | | Y100W | | | | | $3.18 \times 10^5$ | $6.30 \times 10^{-4}$ | 1.98 |
| M34 | | S101T | | | | | $3.18 \times 10^5$ | $8.00 \times 10^{-4}$ | 2.52 |
| M35 | | S101G | | | | | $3.18 \times 10^5$ | $9.00 \times 10^{-3}$ | 28.30 |
| M36 | | L102R | | | | | $3.18 \times 10^5$ | $9.00 \times 10^{-4}$ | 2.83 |
| M37 | | L102A | | | | | $3.18 \times 10^5$ | $9.20 \times 10^{-4}$ | 2.89 |
| M38 | | L102V | | | | | $3.18 \times 10^5$ | $1.50 \times 10^{-3}$ | 4.72 |
| M39 | | L102S | | | | | $3.18 \times 10^5$ | $2.30 \times 10^{-3}$ | 7.23 |
| M40 | | L102T | | | | | $3.18 \times 10^5$ | $4.50 \times 10^{-3}$ | 14.15 |
| M41 | | L102Q | | | | | $3.18 \times 10^5$ | $1.00 \times 10^{-2}$ | 31.45 |
| M42 | | L102E | | | | | $3.18 \times 10^5$ | $1.50 \times 10^{-2}$ | 47.17 |
| M43 | | V104I | | | | | $3.18 \times 10^5$ | $3.00 \times 10^{-4}$ | 0.94 |
| M44 | | V104T | | | | | $3.18 \times 10^5$ | $3.00 \times 10^{-3}$ | 9.43 |
| M45 | | V104P | | | | | $3.18 \times 10^5$ | $1.50 \times 10^{-2}$ | 47.17 |
| M46 | | V104C | | | | | $3.18 \times 10^5$ | $2.00 \times 10^{-2}$ | 62.89 |
| M47 | | V104Q | | | | | $3.18 \times 10^5$ | $2.00 \times 10^{-2}$ | 62.89 |
| M48 | | V104S | | | | | $3.18 \times 10^5$ | $2.60 \times 10^{-2}$ | 81.76 |
| M49 | | V104N | | | | | $3.18 \times 10^5$ | $2.60 \times 10^{-2}$ | 81.76 |
| M50 | | V104F | | | | | $3.18 \times 10^5$ | $2.70 \times 10^{-2}$ | 84.91 |
| M51 | | Y105H | | | | | $3.18 \times 10^5$ | $8.60 \times 10^{-4}$ | 2.70 |
| M52 | | Y105F | | | | | $3.18 \times 10^5$ | $1.30 \times 10^{-3}$ | 4.09 |
| M53 | | Y105W | | | | | $3.18 \times 10^5$ | $1.30 \times 10^{-3}$ | 4.09 |
| M54 | | Y105S | | | | | $3.18 \times 10^5$ | $2.40 \times 10^{-3}$ | 7.55 |
| M55 | | Y105I | | | | | $3.18 \times 10^5$ | $3.00 \times 10^{-3}$ | 9.43 |
| M56 | | Y105V | | | | | $3.18 \times 10^5$ | $3.50 \times 10^{-3}$ | 11.01 |
| M57 | | Y105A | | | | | $3.18 \times 10^5$ | $3.90 \times 10^{-3}$ | 12.26 |

1 = All CDRs are extended CDRs including both Kabat and Chothia CDRs. Amino acid residues are numbered sequentially.
2 = underlined $k_{on}$ were experimentally determined. Others were estimated to be the same as 9TL.
3 = $K_D$ values were calculated as $K_D = k_{off}/k_{on}$.

Example 2

Characterization of Epitope on Aβ1-40 Peptide that Antibody 9TL Binds

To determine the epitope on Aβ polypeptide that is recognized by antibody 9TL, Surface Plasmon Resonance (SPR, Biacore 3000) binding analysis was used. Aβ$_{1-40}$ polypeptide coupled to biotin (Global Peptide Services, CO) was immobilized on a streptavidin-coated chip (SA chip). The binding of Aβ antibodies Fab fragments (at 50 nM) to the immobilized Aβ$_{1-40}$ in the absence or presence of different soluble fragments of the Aβ peptide (at 10 μM, from American Peptide Company Inc., CA). Amino acid sequences of Aβ$_{1-40}$, Aβ$_{1-42}$, and Aβ$_{1-43}$ are shown in below in Table 4. The Aβ peptides which displaced binding of antibody 9TL Fab fragment to Aβ$_{1-40}$ were Aβ$_{28-40}$, Aβ$_{1-40}$, Aβ$_{33-40}$, and Aβ$_{17-40}$, respectively (FIG. 2). Thus, antibody 9TL binds to a C-terminal peptide (33-40) of Aβ$_{1-40}$. As shown in FIG. 2, the Aβ$_{1-28}$, Aβ$_{28-42}$, Aβ$_{22-35}$, Aβ$_{1-16}$, Aβ$_{1-43}$, and Aβ$_{1-38}$ peptide did not inhibit the binding of antibody 9TL Fab fragment, suggesting that antibody 9TL binds to the C-terminus of Aβ$_{1-40}$ peptide.

In addition, Aβ$_{28-42}$ and Aβ$_{1-43}$ peptide did not inhibit binding of antibody 9TL to Aβ$_{1-40}$ although they could readily inhibit Aβ$_{1-40}$ binding to control antibody (antibody 2289, this antibody is described in U.S. Appl. Pub. No. 2004/0146512 and WO04/032868) which bind to 16-28 of Aβ$_{1-40}$. These results show that antibody 9TL preferentially binds to Aβ$_{1-40}$, but not to Aβ$_{1-42}$ and Aβ$_{1-43}$.

TABLE 4

Amino acid sequences of beta amyloid peptides 1-40 (WT) DAEFRHDSGYEVHHQKLVFFAEDVGS (SEQ ID NO: 15)
NKGAIIGLMVGGVV 1-42 (WT) DAEFRHDSGYEVHHQKLVFFAEDVGS (SEQ ID NO: 16)
NKGAIIGLMVGGVVIA 1-43 (WT) DAEFRHDSGYEVHHQKLVFFAEDVGS (SEQ ID NO: 17)
NKGAIIGLMVGGVVIAT

Example 3

Generation of Monoclonal Antibody 2H6 and Deglycosylated 2H6

A. Generation and Characterization of Monoclonal Antibody 2H6

Mice were immunized with 25-100 µg of a peptide (amino acid 28-40 of Aβ$_{1-40}$) conjugated to KLH in adjuvant (50 µl per footpad, 100 µl total per mouse) at about 16 consecutive week intervals as described in Geerligs H J et al., 1989, J. Immunol. Methods 124:95-102; Kenney J S et al., 1989, J. Immunol. Methods 121:157-166; and Wicher K et al., 1989, Int. Arch. Allergy Appl. Immunol. 89:128-135. Mice were first immunized with 50 µg of the peptide in CFA (complete Freud's adjuvant). After 21 days, mice were secondly immunized with 25 µg of the peptide in IFA (incomplete Freud's adjuvant). Twenty three days later after the second immunization, third immunization was performed with 25 µg of the peptide in IFA. Ten days later, antibody titers were tested using ELISA. Forth immunization was performed with 25 µg of the peptide in IFA 34 days after the third immunization. Final booster was performed with 100 µg soluble peptide 32 days after the forth immunization.

Splenocytes were obtained from the immunized mouse and fused with NSO myeloma cells at a ratio of 10:1, with polyethylene glycol 1500. The hybrids were plated out into 96-well plates in DMEM containing 20% horse serum and 2-oxaloacetate/pyruvate/insulin (Sigma), and hypoxanthine/aminopterin/thymidine selection was begun. On day 8, 100 µl of DMEM containing 20% horse serum was added to all the wells. Supernatants of the hybrids were screened by using antibody capture immunoassay. Determination of antibody class was done with class-specific second antibodies.

A panel of monoclonal antibody-producing cell lines was selected for characterization. One cell line selected produces as antibody designated 2H6. This antibody was determined to have IgG2b heavy chain.

The affinity of antibody 2H6 to Aβ$_{1-40}$ was determined. Monoclonal antibody 2H6 was purified from supernatants of hybridoma cultures using protein A affinity chromatography. The supernatants was equilibrated to pH 8. The supernatants were then loaded to the protein A column MabSelect (Amersham Biosciences # 17-5199-02) equilibrated with PBS to pH 8. The column was washed with 5 column volumes of PBS, pH 8. The antibody was eluted with 50 mM citrate-phosphate buffer, pH 3. The eluted antibody was neutralized with 1M Phosphate Buffer, pH 8. The purified antibody was dialyzed with PBS. The antibody concentration was determined by SDS-PAGE, using a murine mAb standard curve.

2H6Fabs were prepared by papain proteolysis of the 2H6 full antibody using Immunopure Fab kit (pierce # 44885) and purified by flow through protein A chromatography following manufacturer instructions. Concentration was determined by SDS-PAGE and A280 using 1OD=0.6 mg/ml.

Affinities of 2H6 monoclonal antibody were determined using the BIAcore3000™ surface plasmon resonance (SPR) system (BIAcore, INC, Piscaway N.J.). One way of determining the affinity was immobilizing 2H6 antibody on CM5 chip and measuring binding kinetics of Aβ$_{1-40}$ peptide to the antibody. CM5 chips were activated with N-ethyl-N'-(3-dimethylaminopropyl)-carbodiimide hydrochloride (EDC) and N-hydroxysuccinimide (NHS) according to the supplier's instructions. 2H6 monoclonal antibody was diluted into 10 mM sodium acetate pH 4.0 or 5.0 and injected over the activated chip at a concentration of 0.005 mg/mL. Using variable flow time across the individual chip channels, a range of antibody density was achieved: 1000-2000 or 2000-3000 response units (RU). The chip was blocked with ethanolamine. Regeneration studies showed that a mixture of Pierce elution buffer (Product No. 21004, Pierce Biotechnology, Rockford, Ill.) and 4 M NaCl (2:1) effectively removed the bound Aβ$_{1-40}$ peptide while keeping the activity of 2H6 antibody on the chip for over 200 injections. HBS-EP buffer (0.01M HEPES, pH 7.4, 0.15 M NaCl, 3 mM EDTA, 0.005% Surfactant P20) was used as running buffer for all the BIAcore assays. Serial dilutions (0.1-10× estimated K$_D$) of purified Aβ$_{1-40}$ synthetic peptide samples were injected for 1 min at 100 µL/min and dissociation times of 10 min were allowed. Kinetic association rates (k$_{on}$) and dissociation rates (k$_{off}$) were obtained simultaneously by fitting the data to a 1:1 Langmuir binding model (Karlsson, R. Roos, H. Fagerstam, L. Petersson, B. (1994). Methods Enzymology 6.99-110) using the BIAevaluation program. Equilibrium dissociation constant (K$_D$) values were calculated as k$_{off}$/k$_{on}$.

Alternatively, affinity was determined by immobilizing Aβ$_{1-40}$ peptide on SA chip and measuring binding kinetics of 2H6Fab to the immobilized Aβ$_{1-40}$ peptide. Affinities of 2H6Fab fragment was determined by Surface Plasmon Resonance (SPR) system (BIAcore 3000™, BIAcore, Inc., Piscaway, N.J.). SA chips (streptavidin) were used according to the supplier's instructions. Biotinylated Aβ peptide 1-40 (SEQ ID NO:15) was diluted into HBS-EP (10 mM HEPES pH 7.4, 150 mM NaCl, 3 mM EDTA, 0.005% P20) and injected over the chip at a concentration of 0.005 mg/mL. Using variable flow time across the individual chip channels, two ranges of antigen density were achieved: 10-200 response units (RU) for detailed kinetic studies and 500-600 RU for concentration studies. Regeneration studies showed that a mixture of Pierce elution buffer and 4 M NaCl (2:1) effectively removed the bound Fab while keeping the activity of Aβ peptide on the chip for over 200 injections. HBS-EP buffer was used as running buffer for all the BIAcore assays. Serial dilutions (0.1-10× estimated KD) of purified Fab samples were injected for 2 min at 100 µL/min and dissociation times of 10 min were allowed. The concentrations of the Fab proteins were determined by ELISA and/or SDS-PAGE electrophoresis using a standard Fab of known concentration (determined by amino acid analysis). Kinetic association rates (k$_{on}$) and dissociation rates (k$_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant (K$_D$) values were calculated as k$_{off}$/k$_{on}$. The affinity of 2H6 antibody determined using both methods described above is shown in Table 5 below.

Affinity for murine antibody 2286, which binds to a peptide of amino acid 28-40 of Aβ$_{1-40}$, was tested as described above. Antibody 2286 is described in U.S. application Ser. No. 10/683,815 and PCT/US03/32080.

TABLE 5

Binding affinity of antibody 2H6 and 2286

|  | k$_{on}$ (1/Ms) | K$_{off}$ (1/s) | K$_D$ (nM) |
|---|---|---|---|
| 2H6 mAb on CM5 chip, Aβ$_{1-40}$ flowed on | 4.67 × 10$^5$ | 3.9 × 10$^{-3}$ | 9 |
| Aβ$_{1-40}$ on SA chip, 2H6 Fab flowed on | 6.3 × 10$^5$ | 3.0 × 10$^{-3}$ | 4.7 |
| 2286 mAb on CM5 chip, Aβ$_{1-40}$ flowed on | 1.56 × 10$^5$ | 0.0419 | 269 |
| Aβ$_{1-40}$ on SA chip, 2286 Fab flowed on | 1.8 × 10$^5$ | 0.044 | 245 |

To determine the epitope on Aβ polypeptide recognized by antibody 2H6, Surface Plasmon Resonance (SPR, Biacore 3000) binding analysis was used. Aβ$_{1-40}$ polypeptide (SEQ ID NO:15) coupled to biotin (Global Peptide Services, CO) was immobilized on a streptavidin-coated chip (SA chip). The binding of Aβ antibodies (at 100 nM) to the immobilized $A\beta_{1-40}$ in the absence or presence of different soluble fragments of the Aβ peptide (at 16 μM, from American Peptide Company Inc., CA). The Aβ peptides which displaced binding of antibody 2H6 to $A\beta_{1-40}$ were $A\beta_{17-40}$, $A\beta_{33-40}$, and $A\beta_{1-40}$, respectively (FIG. 3). Thus, antibody 2H6 binds to a C-terminal peptide (33-40) of $A\beta_{1-40}$. However, this C-terminal peptide (33-40) of $A\beta_{1-40}$ did not displace binding of antibody 2286 to $A\beta_{1-40}$ at the concentration tested. As shown in FIG. 3, the $A\beta_{1-38}$ peptide did not inhibit the binding of antibody 2H6 or antibody 2286 to $A\beta_{1-40}$, suggesting that, similar to antibody 2286, the epitope that antibody 2H6 binds includes amino acids 39 and/or 40 of the $A\beta_{1-40}$ peptide (FIG. 3).

In addition, $A\beta_{1-42}$ and $A\beta_{1-43}$ peptide did not inhibit binding of antibody 2H6 to $A\beta_{1-40}$ although they could readily inhibit $A\beta_{1-40}$ binding to control antibody (antibody 2289, this antibody is described in U.S. application Ser. No. 10/683,815 and PCT/US03/32080) which bind to 16-28 of $A\beta_{1-40}$ (FIG. 3). These results show that antibody 2H6 preferentially binds to $A\beta_{1-40}$, but not to $A\beta_{1-42}$ and $A\beta_{1-43}$.

To further assess the involvement of discrete amino acid residues of the β-amyloid peptide that antibody 2H6 binds, different $A\beta_{1-40}$ variants, in which each of the last 6 amino acids ($A\beta_{1-40}$ amino acid residues 35-40) was individually replaced by an alanine (alanine scanning mutagenesis), were generated by site directed mutagenesis. These $A\beta_{1-40}$ variants (sequences shown in Table 6) were expressed in *E. coli* as Glutathione-S-Transferase (GST) fusion proteins (Amersham Pharmacia Biotech, Piscataway, N.J. USA) followed by affinity purification on a Glutathione-Agarose beads (Sigma-Aldrich Corp., St. Louis, Mo., USA). As control, Wild-type (WT) $A\beta_{1-40}$ as well as $A\beta_{1-41}$, $A\beta_{1-42}$, and $A\beta_{1-39}$ were also expressed as GST fusion proteins. $A\beta_{1-40}$, $A\beta_{1-41}$, $A\beta_{1-42}$, $A\beta_{1-39}$, as well as the six different variants (M35A(1-40), V36A(1-40), G37A(1-40), G38A(1-40), V39A(1-40), V40A (1-40) shown in Table 6 were then immobilized (100 μl of 0.025 μg/μl of GST-peptide per well) onto ELISA assay plates and incubated with either of mAb 2286, 2289, and 2H6 in serial dilution from 0.3 nM down (data using 0.3 nM mAb are shown in FIG. 4). After 10 consecutive washes, assay plates were incubated with 100 μl of 0.03 μg/ml per well of Biotin-conjugated Goat-anti-Mouse (H+L) antibody (Vector Laboratories, vector #BA-9200, Burllingame Calif., USA) followed by 100 μl of 0.025 μg/ml per well of HRP-conjugated Streptavidin (Amersham Biosciences Corp., #RPN4401V, NJ, USA). The absorbance of the plate was read at 450 nm.

TABLE 6

Amino acid sequences of beta amyloid peptides and variants

| | | |
|---|---|---|
| 1-40 (WT) | DAEFRHDSGYEVHHQKLVFFAEDV GSNKGAIIGLMVGGVV | (SEQ ID NO: 15) |
| 1-42 (WT) | DAEFRHDSGYEVHHQKLVFFAEDV GSNKGAIIGLNVGCVVIA | (SEQ ID NO: 16) |
| 1-43 (WT) | DAEFRHDSGYEVHHQKLVFFAEDV GSNKGAIIGLMVGGVVIAT | (SEQ ID NO: 17) |
| 1-41 (WT) | DAEFRHDSGYEVHHQKLVFFAEDV GSNKGAIIGLMVGGVVI | (SEQ ID NO: 18) |
| 1-39 (WT) | DAEFRHDSGYEVHHQKLVFFAEDV GSNKGAIIGLMVGGV | (SEQ ID NO: 19) |

TABLE 6-continued

Amino acid sequences of beta amyloid peptides and variants

| | | |
|---|---|---|
| M35A(1-40) | DAEFRHDSGYEVHHQKLVFFAEDV GSNKGAIIGLAVGGVV | (SEQ ID NO: 20) |
| V36A(1-40) | DAEFRHDSGYEVHHQKLVFFAEDV GSNKGAIIGLMAGGVV | (SEQ ID NO: 21) |
| G37A(1-40) | DAEFRHDSGYEVHHQKLVFFAEDV GSNKGAIIGLMVAGVV | (SEQ ID NO: 22) |
| G38A(1-40) | DAEFRHDSGYEVHHQKLVFFAEDV GSNKGAIIGLMVGAVV | (SEQ ID NO: 23) |
| V39A(1-40) | DAEFRHDSGYEVHHQKLVFFAEDV GSNKGAIIGLMVGGAV | (SEQ ID NO: 24) |
| V40A(1-40) | DAEFRHDSGYEVHHQKLVFFAEDV GSNKGAIIGLMVGGVA | (SEQ ID NO: 25) |

As shown in FIG. 4, Mab 2289 which was directed to amino acid 16 to 28 of Aβ, recognized all variants with the same intensity and served as internal positive control of protein concentration and protein integrity on the plate. Antibody 2H6 did not recognize $A\beta_{1-41}$, $A\beta_{1-39}$, or $A\beta_{1-42}$ as shown in FIG. 4. $A\beta_{1-40}$ variants V40A, V39A, G38A, G37A, V36A, and M35A showed reduced binding to antibody 2H6, demonstrating that antibody 2H6 epitope extended for at least 6 amino acids at the C terminal end of $A\beta_{1-40}$. Mutations of V and G to A are very conservative and are not likely to produce important conformational changes in proteins, therefore, the large effect of these mutations to antibody 2H6 binding might be due to the ability of the antibody to differentiate between the mentioned amino acids in the context of Aβ and these data demonstrated a very high degree of specificity for this antibody.

To determine whether 2H6 and 9TL compete for binding to $A\beta_{1-40}$, competition experiments were performed using Biacore assay. Antibody 2H6, 9TL and 2289 were immobilized on different channels of a CM5 chip. CM5 chip channels were activated with N-ethyl-N'-(3-dimethylaminopropyl)-carbodiimide hydrochloride (EDC) and N-hydroxysuccinimide (NHS) according to the supplier's instructions. Antibody 2H6, 9TL, and 2289 were each diluted into 10 mM sodium acetate pH 4.0 and injected over an activated chip at a concentration of 0.005 mg/mL. Antibody density was 1625 response units (RU) for 2H6; 4000 RU for 9TL; and 2200 RU for 2289. Each channel was blocked with ethanolamine. $A\beta_{1-40}$ peptide (150 uM) was flowed onto the chip for 2 min. Then antibody 2H6 (to be tested for competition of binding) at 0.6 uM was flowed onto the chip for 1 min. HBS-EP buffer (0.01M HEPES, pH 7.4, 0.15 M NaCl, 3 mM EDTA, 0.005% Surfactant P20) was used as running buffer for all the BIAcore assays. After measuring binding of $A\beta_{1-40}$, all channels of the chip were regenerated by washing twice with a mixture of Pierce elution buffer (Product No. 21004, Pierce Biotechnology, Rockford, Ill.) and 4 M NaCl (2:1) for 6 sec. Competition binding was then performed for antibody 9TL, and then antibody 2289. Competition between 9TL and 2H6 for binding to $A\beta_{1-40}$ was observed, but no competition was observed between 9TL and 2289 or between 2H6 and 2289. Observations of competition between the antibody immobilized and the same antibody flowed onto the chip served as the positive control.

B. Antibody 2H6 Does Not Bind to APP

To determine whether 2H6 binds to amyloid precursor proteins (APP), binding of 2H6 to cells transfected with wild-type APP was determined. 293 cells were transfected with a cDNA encoding wild type human amyloid precursor protein. Forty eight hours after the transfection, cells were incubated on ice for 45 minutes with monoclonal antibodies anti-$A\beta_{1-16}$, anti-$A\beta_{16-28}$, or 2H6 (5 ug/ml in DMEM with 10% FCS). The cells were then washed three times in PBS for 5 minutes, fixed with 4% PFA. The cells were washed three times again in PBS, and antibody binding was detected with secondary Cy3-conjugated goat anti-mouse antibody (dilution of 1:500) from Jackson Immunoresearch under fluorescence microscope.

Anti-$A\beta_{1-16}$ and anti-$A\beta_{16-28}$ antibodies, which recognize N-terminal or central epitopes in $A\beta$, both showed significant binding to APP precursor proteins expressed on cells. In contrast, 2H6 did not bind to APP expressing cells.

C. Generation of Deglycosylated Antibody 2H6

To generate deglycosylated antibody 2H6, purified antibody 2H6 was incubated at 37° C. for 7 days with peptide-N-glycosidase F (Prozyme, 0.05 U per mg of antibody) in 20 mM Tris-HCl pH 8.0. Completeness of deglycosylation was verified by MALDI-TOF-MS and protein gel electrophoresis. Deglycosylated antibodies were purified by Protein A chromatography and endotoxin was removed by Q-Sepharose. The binding affinity to $A\beta_{1-40}$ of the deglycosylated 2H6 was tested using Biacore assay described above, and the binding affinity of the deglycosylated 2H6 to $A\beta_{1-40}$ was found to be identical to the intact antibody 2H6.

Example 4

Reversal of Cognitive Deficits and Histological Symptoms with Less Microhemorrhage in an Animal Model of Alzheimer's Disease by Administration of Deglycosylated 2H6

A. Experimental Protocol

Administration of antibodies. Transgenic mice over-expressing the "Swedish" mutant amyloid precursor protein (APP Tg2576 with K670N/M671; Hsiao et al., Science 274: 99-102 (1996)) were used for the experiments. The Alzheimer's-like phenotype present in these mice has been well-characterized. Holcomb et al., Nat. Med. 4:97-100 (1998); Holcomb et al., Behav. Gen. 29:177-185 (1999); and McGowan E, Neurobiol. Dis. 6:231-244 (1999). For the sixteen weeks treatment study, APP-transgenic mice, aged 20 months, were assigned to one of the four groups. The first group received weekly intraperitoneal anti-$A\beta$ antibody 2H6 (mouse monoclonal anti-human $A\beta_{28-40}$ IgG2b described in Example 3) injections for a period of 16 weeks (n=4). The second group received weekly intraperitoneal deglycosylated anti-$A\beta$ antibody 2H6 (produced as described in Example 3) injections for a period of 16 weeks (n=5). The third group received weekly intraperitoneal anti-AMN antibody (2906; mouse-monoclonal anti-*Drosophila* amnesiac protein IgG1) injections for a period of 16 weeks (n=6). Non-transgenic littermates were treated for 16 weeks with either anti-AMN antibody (n=4) or 2H6 (n=2).

Behavioral analysis. Following 16 weeks of antibody treatment, the mice from the study were subjected to a two-day radial-arm water-maze paradigm as described previously. Wilcock et al., *J. Neuroinflammation* 1:24 (2004). The appa ratus was a 6-arm maze as described previously. Gordon et al., *Neurobiol. Aging* 22:377-385 (2001). On day one, 15 trials were run in three blocks of 5. A cohort of 4 mice were run sequentially for each block (i.e., each of 4 mice get trial one, then the same mice get trial two, etc.). After each 5-trial block, a second cohort of mice was run permitting an extended rest period before mice were exposed to the second block of 5 trials. The goal arm was different for each mouse in a cohort to minimize odor cues. The start arm was varied for each trial, with the goal arm remaining constant for a given individual for both days. For the first 11 trials, the platform was alternately visible then hidden (hidden for the last 4 trials). On day two, the mice were run in exactly the same manner as day one except that the platform was hidden for all trials. The number of errors (incorrect arm entries) was measured in a one-minute time frame. Mice failing to make an arm choice in 20 seconds were assigned one error, but no mice in this study had to be assigned an error in this manner. Due to the numbers of mice in the study, the tester was unaware of treatment group identity of each mouse. Since the dependent measures in the radial-arm water-maze task were quantitative, not evaluative, the potential for tester bias was reduced. In order to minimize the influence of individual trial variability, each mouse's errors for 3 consecutive trials were averaged producing 5 data points for each day, which were analyzed statistically by ANOVA using StatView (SAS Institute Inc., NC).

Histological analysis. On the day of sacrifice, mice were weighed, overdosed with 100 mg/kg Nembutal (Abbott laboratories, North Chicago, Ill.), and then intracardially perfused with 25 mL of 0.9% sodium chloride. Brains were rapidly removed, and the left half of the brain was immersion fixed for 24 h in freshly prepared 4% paraformaldehyde in 100 mM $KPO_4$ (pH 7.2) for histopathology. The hemi-brains were then incubated for 24 h in 10%, 20% and 30% sucrose sequentially for cyroprotection. Horizontal sections of 25µ thickness were collected using a sliding microtome and stored at 4° C. in Dulbecco's phosphate-buffered saline with sodium azide (pH 7.2) to prevent microbial growth. A series of 8 equally spaced tissue sections 600µ apart were randomly selected spanning the entire brain and stained using free-floating immunohistochemistry for total $A\beta$ (rabbit polyclonal anti-pan $A\beta$; Biosource, Camarillo, Calif., 1:10,000) as previously described. Gordon et al., *Exp. Neurol.* 173:183-195 (2002); Wilcock et al., *J. Neurosci.* 24:6144-6151 (2004). A second series of tissue sections 600 µm apart were stained using 0.2% Congo red in NaCl-saturated 80% ethanol. Another set of sections were also mounted and stained for hemosiderin using 2% potassium ferrocyanide in 2% hydrochloric acid for 15 min, followed by a counterstain in a 1% neutral red solution for 10 min. Quantification of Congo red staining and $A\beta$ immunohistochemistry was performed using the Image-Pro Plus (Media Cybernetics, Silver Spring, Md.) to analyze the percent area occupied by positive stain. One region of the frontal cortex and three regions of the hippocampus were analyzed (to ensure that there was no regional bias in the hippocampal values). The initial analysis of Congo red was performed to give a total value. A second analysis was performed after manually editing out all of the parenchymal amyloid deposits to yield a percent area restricted to vascular Congo red staining. To estimate the parenchymal area of Congo red, the vascular amyloid values were subtracted from the total percentage. For the hemosiderin stain the numbers of Prussian blue-positive sites were counted on all sections and the average number of sites per section calculated. Qualitative differ ences between animals were observed at the sections at a low magnification. Eight equally spaced sections were examined and the number of positive profiles was determined and averaged to a per-section value. To assess possible treatment-related differences, the values for each treatment group were analyzed by one-way ANOVA followed by Fisher's LSD: means comparisons.

Measurement of serum level of Aβ peptide using ELISA. Serum collected one day after the last dosing of antibodies was diluted and incubated in 96-well microtiter plates (MaxiSorp; Nunc, Rosklide, Denmark), which were precoated with antibody 6E10 (anti-beta amyloid antibody that binds to $A\beta_{1-17}$; Signet, Dedham, Mass.) at 5 ug/ml in PBS buffer, pH 7.4. The secondary antibody was biotinylated 4G8 (anti-beta amyloid antibody that binds to $A\beta_{17-24}$; Signet) at a 1:5000 dilution. Detection was done using a streptavidin-horseradish peroxidase conjugate (Amersham Biosciences), followed by TMB substrate (KPL, Gaithersburg, Md.). $A\beta_{1-40}$ (American Peptide) scaling from 6-400 pM were used for standard curves.

B. Results

Reversal of cognitive deficits by administration of deglycosylated antibody. The radial-arm water-maze task detects spatial learning and memory deficits in transgenic mouse models. Gordon et al., *Neurobiol. Aging.* 22:377-385 (2001); Morgan et al., *Nature* 408:982-985 (2000). Animal treated with antibody 2H6, deglycosylated 2H6, or anti-AMN for 16 weeks were tested for spatial navigation learning in a two-day version of the radial-arm water maze. Nontransgenic normal mice (including 2 mice treated with 2H6 antibody and 4 mice treated with anti-AMN antibody; these two groups were combined since no behavior difference was observed) were also tested in the two-day version of the radial-arm water maze. As shown in FIG. 5, APP-transgenic mice treated with the control antibody (anti-AMN) failed to learn platform location over two days of testing and were significantly impaired compared to the nontransgenic mice as previously described. Wilcock et al., *J. Neuroinflammation* 1:24 (2004). However, APP-transgenic mice administered the anti-Aβ antibody 2H6 and deglycosylated 2H6 demonstrated a significant reversal of the impairment observed in the control-treated APP-transgenic mice, ending day two with a mean performance near 1 error per trial (FIG. 5). The control-treated APP-transgenic mice has a mean performance near 3 errors per trial at the ending of day two (FIG. 5). The data shown in FIG. 5 indicate that the deglycosylated antibody works as well as the intact antibody for reversal of cognitive deficits in the APP-transgenic mice.

Reduction of Aβ deposits without increasing microhemorrhage. As shown Table 7 below, total Aβ immunostaining in the hippocampus was significantly reduced after 16 weeks immunotherapy with antibody 2H6 (about 56% reduction, p=0.0001) and deglycosylated 2H6 (about 58% reduction, p<0.0001) as compared to the control antibody-treated group (anti-AMN). As shown in Table 8 below, total Aβ immunostaining in the frontal cortex was significantly reduced after 16 weeks immunotherapy with antibody 2H6 (about 50% reduction, p<0.0001) and deglycosylated 2H6 (about 51% reduction, p<0.0001) as compared to the control antibody-treated group (anti-AMN).

TABLE 7

Total Aβ load for hippocampus after 16 weeks of antibody treatment. Mean percent area occupied by positive immunohistochemical stain for Aβ, and standard deviation and standard error of the mean for the hippocampus are shown.

| Antibody administered | Number of animals analyzed | Mean | Std. Dev. | Std. Error |
|---|---|---|---|---|
| Anti-AMN | 6 | 27.127 | 4.602 | 1.879 |
| 2H6 | 4 | 12.011 | 5.057 | 2.529 |
| Deglycosylated 2H6 | 5 | 11.344 | 4.765 | 2.131 |

TABLE 8

Total Aβ load for frontal cortex after 16 weeks of antibody treatment. Mean percent area occupied by positive immunohistochemical stain for Aβ, and standard deviation and standard error of the mean for the frontal cortex are shown.

| Antibody administered | Number of animals analyzed | Mean | Std. Dev. | Std. Error |
|---|---|---|---|---|
| Anti-AMN | 6 | 47.060 | 4.667 | 1.905 |
| 2H6 | 4 | 23.708 | 6.355 | 3.178 |
| Deglycosylated 2H6 | 5 | 22.834 | 1.970 | 0.881 |

As shown Table 9, total Congo-red staining in the hippocampus was significantly reduced after 16 weeks immunotherapy with antibody 2H6 (about 77% reduction, p<0.0001) and deglycosylated 2H6 (about 53% reduction, p<0.0001) as compared to the control antibody-treated group (anti-AMN). As shown in Table 10, total Congo-red staining in the frontal cortex was also significantly reduced after 16 weeks immunotherapy with antibody 2H6 (about 79% reduction, p<0.0001) and deglycosylated 2H6 (about 68% reduction, p<0.0001) as compared to the control antibody-treated group (anti-AMN).

TABLE 9

Total Congo-red staining for hippocampus after 16 weeks of antibody treatment. Mean percent area occupied by positive Congo-red stain for Aβ, and standard deviation and standard error of the mean for the hippocampus are shown.

| Antibody administered | Number of animals analyzed | Mean | Std. Dev. | Std. Error |
|---|---|---|---|---|
| Anti-AMN | 6 | 1.210 | 0.081 | 0.033 |
| 2H6 | 4 | 0.281 | 0.021 | 0.010 |
| Deglycosylated 2H6 | 5 | 0.573 | 0.101 | 0.045 |

TABLE 10

Total Congo-red staining for frontal cortex after 16 weeks of antibody treatment. Mean percent area occupied by positive Congo-red stain for Aβ, and standard deviation and standard error of the mean for the frontal cortex are shown.

| Antibody administered | Number of animals analyzed | Mean | Std. Dev. | Std. Error |
|---|---|---|---|---|
| Anti-AMN | 6 | 2.507 | 0.691 | 0.282 |
| 2H6 | 4 | 0.520 | 0.047 | 0.023 |
| Deglycosylated 2H6 | 5 | 0.807 | 0.104 | 0.046 |

Parenchymal (Tables 11 and 12; and FIG. 6) and vascular (Tables 13 and 14; FIG. 7) Congo-red staining were analyzed separately for both frontal cortex and hippocampus. As shown Table 11 and FIG. 6A, parenchymal Congo-red staining in the frontal cortex was significantly reduced after 16 weeks immunotherapy with antibody 2H6 (about 98% reduction, $p<0.0001$) and deglycosylated 2H6 (about 77% reduction, $p<0.0001$) as compared to the control antibody-treated group (anti-AMN). As shown in Table 12 and FIG. 6B, parenchymal Congo-red staining in the hippocampus was also significantly reduced after 16 weeks immunotherapy with antibody 2H6 (about 96% reduction, $p<0.0001$) and deglycosylated 2H6 (about 63% reduction, $p<0.0001$) as compared to the control antibody-treated group (anti-AMN). The deglycosylated 2H6 was less effective than the intact 2H6 antibody in reducing Congo-red load in the frontal cortex and hippocampus.

TABLE 11

Parenchymal Congo-red staining for frontal cortex after 16 weeks of antibody treatment. Mean percent area occupied by positive Congo-red stain for Aβ, and standard deviation and standard error of the mean for the frontal cortex are shown.

| Antibody administered | Number of animals analyzed | Mean | Std. Dev. | Std. Error |
|---|---|---|---|---|
| Anti-AMN | 6 | 2.360 | 0.676 | 0.276 |
| 2H6 | 4 | 0.059 | 0.047 | 0.024 |
| Deglycosylated 2H6 | 5 | 0.537 | 0.144 | 0.064 |

TABLE 12

Parenchymal Congo-red staining for hippocampus after 16 weeks of antibody treatment. Mean percent area occupied by positive Congo-red stain for Aβ, and standard deviation and standard error of the mean for the hippocampus are shown.

| Antibody administered | Number of animals analyzed | Mean | Std. Dev. | Std. Error |
|---|---|---|---|---|
| Anti-AMN | 6 | 1.117 | 0.104 | 0.043 |
| 2H6 | 4 | 0.040 | 0.029 | 0.015 |
| Deglycosylated 2H6 | 5 | 0.416 | 0.078 | 0.035 |

As shown Table 13 and FIG. 7A, vascular Congo-red staining in the hippocampus was significantly increased after 16 weeks immunotherapy with antibody 2H6 (about 2.7 fold, $p<0.0001$) and deglycosylated 2H6 (about 1.7 fold, $p=0.0185$) as compared to the control antibody-treated group (anti-AMN). As shown in Table 14 and FIG. 7B, vascular Congo-red staining in the frontal cortex was also significantly increased after 16 weeks immunotherapy with antibody 2H6 (about 3.5 fold, $p<0.0001$) and deglycosylated 2H6 (about 1.8 fold, $p=0.0048$) as compared to the control antibody-treated group (anti-AMN). The increase of vascular Congo-red staining in the deglycosylated 2H6 treated group was significantly less than in the intact 2H6 antibody treated group for both hippocampus ($p=0.0025$) and frontal cortex ($p<0.0001$).

TABLE 13

Vascular Congo-red staining for hippocampus after 16 weeks of antibody treatment. Mean percent area occupied by positive Congo-red stain for Aβ, and standard deviation and standard error of the mean for the hippocampus are shown.

| Antibody administered | Number of animals analyzed | Mean | Std. Dev. | Std. Error |
|---|---|---|---|---|
| Anti-AMN | 6 | 0.093 | 0.036 | 0.015 |
| 2H6 | 4 | 0.253 | 0.053 | 0.027 |
| Deglycosylated 2H6 | 5 | 0.157 | 0.030 | 0.013 |

TABLE 14

Vascular Congo-red staining for frontal cortex after 16 weeks of antibody treatment. Mean percent area occupied by positive Congo-red stain for Aβ, and standard deviation and standard error of the mean for the frontal cortex are shown.

| Antibody administered | Number of animals analyzed | Mean | Std. Dev. | Std. Error |
|---|---|---|---|---|
| Anti-AMN | 6 | 0.147 | 0.055 | 0.023 |
| 2H6 | 4 | 0.511 | 0.084 | 0.042 |
| Deglycosylated 2H6 | 5 | 0.269 | 0.043 | 0.019 |

Prussian blue histological stain was used to label hemosiderin, a feric oxide material produced in the breakdown of hemoglobin. Extravenous blood in the brain leads to microglial phagocytosis of the erythrocytes and breakdown of the hemoglobin within them. Thus, ferric oxide-containing microglia are thus markers of past hemorrhage. The number Prussian blue-positive profiles in antibody treated animals were counted. As shown in Table 15 and FIG. 8, treatment with antibody 2H6 significantly ($p<0.0001$) increased Prussian blue staining for about 5.5 fold as compared to the control antibody treated group (anti-AMN). Treatment with deglycosylated 2H6 antibody only increased Prussian blue staining for about 1.8 fold ($p=0.0364$) as compared to the control antibody treated group.

TABLE 15

Prussian blue staining for the entire section after 16 weeks of antibody treatment. Mean percent area occupied by positive Prussian blue stain, and standard deviation and standard error of the mean for the entire section are shown.

| Antibody administered | Number of animals analyzed | Mean | Std. Dev. | Std. Error |
|---|---|---|---|---|
| Anti-AMN | 7 | 0.589 | 0.295 | 0.112 |
| 2H6 | 4 | 3.250 | 0.445 | 0.222 |
| Deglycosylated 2H6 | 5 | 1.050 | 0.143 | 0.064 |

Serum level of Aβ after administration of deglycosylated 2H6 antibody. As shown in FIG. 9, administration of both antibody 2H6 and deglycosylated 2H6 to the APP Tg2576 mice significantly increased serum level of beta-amyloid peptide. However, no significant increase of serum level of beta-amyloid peptide was observed in the APP Tg2576 mice after administration of anti-AMN antibody or in the wild type mice after administration of anti-AMN antibody or antibody 2H6.

This indicates that the increase of serum level of beta-amyloid peptide may be used to assist disgnosis of AD and monitor the response to AD therapy, such as immunotherapy.

C. Conclusion

The above data demonstrate that 1) the deglycosylated antibody 2H6 is as effective as the intact antibody 2H6 in reversing learning and memory deficits in APP Tg2576 mice; 2) the deglycosylated antibody 2H6 is a little less effective as the intact antibody 2H6 in depleting Aβ deposits in hippocampus and frontal cortex as measured by Congo-red staining, but is as effective in depleting Aβ load in hippocampus and frontal cortex as measured by Aβ immunostaining; 3) increase of Aβ deposit (as measured by Congo-red staining) in hippocampous and frontal cortex vasculature by the deglycosylated antibody 2H6 is much less than the intact 2H6 antibody; and 4) microhemorrhage as measured by Prussian blue staining in APP Tg2576 mice treated with the deglycosylated 2H6 antibody was much lower than mice treated with the intact 2H6 antibody. These data suggest that deglycosylated antibody is as effective for improving indications of Alzheimer's disease with lower risk of microhemorrhage in APP Tg2576 mice.

Example 5

Binding Affinity of Various Antibody Fc Regions to Murine and Human Fcγ Receptors and Complement Binding affinity of the antibody Fc regions to Fcγ receptors or complement were measured using BIAcore as described above. Briefly, purified human or murine Fcγ receptors (from R&D Systems) and human C1q (from Quidel) were immobilized on BIAcore CM5 chip by amine chemistry. Serial dilutions of monoclonal antibodies (ranging from 2 nM to the maximum concentration as indicated in Tables 16 and 17) were injected. HBS-EP (0.01M HEPES, pH 7.4, 0.15 M NaCl, 3 mM EDTA, 0.005% Surfactant P20) as running and sample buffer. Binding data were analyzed using 1:1 langmuir interaction model for high affinity interactions, or steady state affinity model for low affinity interactions.

Table 16 below shows the binding affinity of the anti-β-amyloid antibodies as measured by $K_D$ (nM) to murine FcγRI, FcγRIIb, FcγRIII, and human C1q (hC1q). Deglycosylated antibodies have a constant region with removed N-glycosylation. 9TL(hIgG1) and 9TL(hIgG2Δa) have the same variable region (shown in SEQ ID NO:1 and SEQ ID NO:2), but different constant region. 9TL(hIgG1) has a human IgG1 constant region; and 9TL(hIgG2Δa) has a human IgG2a with mutations of A330P331 to S330S331 (Kabat amino acid numbering with reference to the wildtype IgG2a sequence). As shown in Table 16, deglycosylated 2H6, 2294, and 2286 had reduced affinity to all murine Fcγ receptors tested as compared to each corresponding antibody without removed N-glycosylation. Deglycosylated 2H6 also had reduced affinity to human complement as compared to 2H6. 9TL(hIgG1) had no significant binding to mFcγRIIb or mFcγRIII; and 9TL(hIgG2Δa) had no significant binding to any of murine FcγRI, FcγRIIb, FcγRIII, or hC1q.

Table 17 below shows the binding affinity of the anti-β-amyloid antibodies as measured by $K_D$ (nM) to human FcγRI, FcγRIIb/c, FcγRIIIb, and hC1q. As shown in Table 17, 9TL (hIgG2Δa) had no significant binding to human FcγRI or hC1q; and significant lower affinity to human FcγRIIb/c and FcγRIIIb as compared to the affinity of the antibody with human IgG1 constant region to these molecules.

TABLE 16

Binding affinity of antibodies to murine Fcγ receptors and human complement as measured by $K_D$ (nM)

| Antibody | FcγRI | FcγRIIb | FcγRIII | hC1q | Isotype | Maximum antibody concentration tested for binding to Fcγ receptors (nM) |
|---|---|---|---|---|---|---|
| 2H6 | 1,800 | 76,000 | 133,000 | 5,000 | Murine IgG2b | 49,000 |
| Deglycosylated 2H6 | 5,600 | NB | NB | 30,000 | Deglycosylated murine IgG2b | 17,000 |
| 2294 | 1,200 | 13,000 | 19,000 | | Murine IgG2b | 18,000 |
| Deglycosylated 2294 | 8,600 | NB | NB | | Deglycosylated murine IgG2b | 22,000 |
| 2286 | 93 | 5,000 | 10,000 | | Murine IgG1 | 12,000 |
| Deglycosylated 2286 | 2,700 | NB | NB | | Deglycosylated murine IgG1 | 9,300 |
| 9TL(hIgG1) | 800 | NB | NB | 34 | Human IgG1 | 30,000 |
| 9TL(hIgG2Δa) | NB | NB | NB | NB | Human IgG2Δa | 30,000 |

NB: no significant binding when antibody was used at the maximum concentration tested.
Maximum antibody concentration tested for binding to hC1q was 30,000 nM.

TABLE 17

Binding affinity of antibodies to human Fcγ receptors and human complement as measured by $K_D$ (nM)

| Antibody | FcγRI | FcγRIIb/c | FcγRIIIb | hC1q |
|---|---|---|---|---|
| 9TL(hIgG1) | 2.2 | 7,000 | 33,000 | 34 |
| 9TL(hIgG2Δa) | NB | 61,000 | >100,000 | NB |

NB:
no significant binding when antibody is used at 30 μM concentration.
Maximum antibody concentration tested for binding was 30,000 nM.

Example 6

Effect of Deglycosylated 2H6 Antibody on Microglial Activation, Fcγ Receptor Binding, and Amyloid Clearance after Intracranial Administration Surgical procedure and intracranial administration of antibodies Tg2576 transgenic mice aged 19.5 months were assigned to one of the three groups, all groups received intracranial injections into the frontal cortex and hippocampus. The first group received anti-Aβ antibody 2H6 at a concentration of 2 μg/2 μl in each region. The second group received deglycosylated 2H6 antibody at 2 μg/2 μl in each region. The third group received IgG directed against *drosophila* amnesiac protein as a control for nonspecific aspects of intact IgG injection. All mice survived for 72 hours after surgery.

On the day of surgery the mice (Tg2576 transgenic mice) were weighed, anesthetized with isoflurane and placed in a stereotaxic apparatus (51603 dual manipulator lab standard, Stoelting, Wood Dale, Ill.). A midsagittal incision was made to expose the cranium and two burr holes were drilled using a dental drill over the right frontal cortex and hippocampus to the following coordinates: Cortex: AP +1.5 mm, L −2.0 mm, hippocampus: AP −2.7 mm, L −2.5 mm, all taken from bregma. A 26 gauge needle attached to a 10 μl Hamilton (Reno, Nev.) syringe was lowered 3 mm ventral to bregma and a 2 μl injection was made over a 2 minute period. The incision was cleaned with saline and closed with surgical staples.

Tissue preparations. On the day of sacrifice mice were weighed, overdosed with 100 mg/kg pentobarbital (Nembutal sodium solution, Abbott laboratories, North Chicago Ill.) and intracardially perfused with 25 ml 0.9% sodium chloride followed by 50 ml freshly prepared 4% paraformaldehyde (pH=7.4). Brains were rapidly removed and immersion fixed for 24 hours in freshly prepared 4% paraformaldehyde. The brains were then incubated for 24 hours in 10, 20 and 30% sucrose sequentially to cyroprotect them. Horizontal sections of 25 μm thickness were then collected using a sliding microtome and stored at 4° C. in DPBS buffer with sodium azide to prevent microbial growth.

Six to eight sections approximately 100 μm apart were selected spanning the injection site and stained using free-floating immunohistochemistry methods for total Aβ (rabbit antiserum reacting with $A\beta_{1-40}$ and $A\beta_{1-42}$; dilution used 1:10,000), anti-CD45 antibody (Cat. No. MCA 1031G, Serotec, Raleigh N.C.; dilution used 1:5000), and anti-Fcγ receptor (CD16/CD32) antibody (Cat. No. 553141 from BD Biosciences; used as 1:1,000 dilution). Biotinylated goat anti-rabbit at 1:3,000 dilution was used as the secondary antibody for anti-Aβ antibody staining. Biotinylated goat anti-rat at 1:3,000 dilution was used as the secondary antibody for anti-CD45 and Fcγ receptor antibody staining. For immunostaining, some sections were omitted from the primary antibody to assess non-specific immunohistochemical reactions. Adjacent sections were mounted on slides and stained using 4% thioflavine-S (Sigma-Aldrich, St Louis Mo.) for 10 minutes. It should be noted that there were a limited number of sections that include the injection volume.

Data analysis. The immunohistochemical reaction product on all stained sections was measured using a videometric V150 image analysis system (Oncor, San Diego, Calif.) in the injected area of cortex and hippocampus and corresponding regions on the contralateral side of the brain. Data were presented as the ratio of injected side to non-injected side for Aβ staining, thioflavine-S staining, CD45 staining, and Fcγ receptor staining. Normalizing each injection site to the corresponding contralateral site diminishes the influence of interanimal variability and permits reliable measurements of drug effects with a smaller number of mice. To assess possible treatment-related differences, the ratio values for each treatment group were analyzed by ANOVA using StatView software version 5.0.1 (SAS Institute Inc., NC) followed by Fischer's LSD means comparisons.

Results

As shown in FIG. 10, CD45 staining in the frontal cortex and the hippocampus was about the same after intracranial administration of deglycosylated 2H6 antibody as the control antibody. In contrast, CD45 staining in the frontal cortex was significantly higher (p<0.01) and was generally higher in the hippocampus after intracranial administration of 2H6 antibody than the control antibody. This indicates that, unlike antibody 2H6, administration of deglycosylated 2H6 did not activate microglia in the frontal cortex and the hippocampus 72 hours after the administration.

As shown in FIG. 11, FcγII and FcγIII receptor staining in the frontal cortex and the hippocampus was about the same after intracranial administration of deglycosylated 2H6 antibody as the control antibody. In contrast, Fcγ receptor staining in the frontal cortex and the hippocampus was significantly higher (p<0.01) after intracranial administration of 2H6 antibody than the control antibody. This indicates that, unlike antibody 2H6, administration of deglycosylated 2H6 did not activate microglia in the frontal cortex and the hippocampus 72 hours after the administration.

As shown in FIG. 12, Aβ staining was lower in frontal cortex and hippocampus 72 hours after intracranial administration of 2H6 antibody or deglycosylated 2H6 antibody as compared to the control antibody. As shown in FIG. 13, thioflavin-S stained compact plaque was also lower in frontal cortex and hippocampus 72 hours after intracranial administration of 2H6 antibody or deglycosylated 2H6 antibody as compared to the control antibody.

These data indicate that deglycosylated 2H6 antibody was able to reduce Aβ and compact plaques in frontal cortex and hippocampus without inducing microglia activation and inflammatory response.

Example 7

Characterization of Epitope on Aβ Peptide that Antibody 2294 Binds

Antibody 2294 is a murine antibody raised by immunizing a mouse with $A\beta_{1-40}$. This antibody is described in U.S. 2004/0146512 and WO 04/032868.

Binding affinity for antibody 2294 to $A\beta_{1-40}$, $A\beta_{1-42}$, or $A\beta_{22-37}$ was measured using Biacore as described above. Table 18 below shows the affinity of antibody 2294 Fab fragment to various Aβ peptides.

TABLE 18

Binding affinity of antibody 2294 Fab fragment

| | $k_{on}$ (1/Ms) | $K_{off}$ (1/s) | $K_D$ (nM) |
|---|---|---|---|
| Biotinylated $A\beta_{1-40}$ immobilized on streptavidin chip, 2294 Fab flowed onto it | $6.6 \times 10^4$ | $3.95 \times 10^{-4}$ | 6 |
| Biotinylated $A\beta_{1-42}$ immobilized on streptavidin chip, 2294 Fab flowed onto it | $1.1 \times 10^4$ | $4.87 \times 10^{-3}$ | 400 |
| Biotinylated $A\beta_{22-37}$ immobilized on streptavidin chip, 2294 Fab flowed onto it | $5 \times 10^3$ | 0.049 | 10,000 |

Epitope mapping of antibody 2294 was performed by ELISA assay. Biotinylated 15-mer or 10-mer of various Aβ peptides (these peptides have glycine added to the C-terminal end) were immobilized on streptavidin coated plates. NUNC maxisorp plates were coated with 6 ug/ml of streptavidin (Pierce, 21122) in PBS pH 7.4 for more than 1 h at 4° C. Plates were blocked with 1% BSA in PBS buffer pH 7.4. After washing, biotinylated Aβ peptides in PBS pH 7.4 were incubated 1 hour at room temperature. Antibody 2294 (from 2.5 ug/ml to 10 ug/ml) was incubated with the immobilized Aβ peptides for 1 h at room temperature. After washing, plates were incubated with secondary antibody, a HRP conjugated goat anti-human kappa chain antibody (MP Biomedicals, 55233) at 1:5000 dilution. After washing, bound secondary antibody was measured by adding TMB substrate (KPL, 50-76-02, 50-65-02). HRP reaction was stopped by adding 1M phosphoric acid and absorbance at 450 nm was measured. As shown in FIG. 14, antibody 2294 binds to Aβ peptides with amino acids 20-34, 21-35, 22-36, 23-37, 24-38, 25-39, 26-40, and 25-34 with a glycine at the C-terminus; but does not bind to Aβ peptides with amino acids 19-33, 27-41, 24-33, and 27-35 having a glycine at the C-terminus of these peptides. This suggests that the epitope of antibody 2294 binds includes amino acids from 26 to 34.

To further determine the epitope on Aβ peptide that is recognized by antibody 2294, ELISA binding analysis was used. Various Aβ peptides (Global Peptide Services, CO) was immobilized on a ELISA plate. The binding of 2294 full antibody (at 20 nM) to the immobilized Aβ was determined by ELISA as described above. Antibody 2294 binds to Aβ peptides 17-40, 17-42, 28-40, 1-38, 1-40, 1-42, and 1-43. Antibody 2294 did not bind to Aβ peptide 1-16, 1-28, 28-42, 22-35, and 33-40. Thus, antibody 2294 binds to the C-terminus of various truncated Aβ peptide, for example, 1-38, 1-40, 1-42, and 1-43.

Table 19 below shows binding comparison of 2294 to $A\beta_{1-40}$ to other Aβ peptide as measured by Biacore assay. Antibody 2294 (full antibody) has the strongest binding to $A\beta_{1-40}$ as compared to other peptides, with significantly lower binding to truncated $A\beta_{1-40}$ (such as 1-36, 1-37, 1-38, and 1-39), $A\beta_{1-42}$ and $A\beta_{1-43}$. This indicates that the side chain or backbone of amino acid 40 (Valine) of Aβ is involved in binding of 2294 to $A\beta_{1-40}$; and binding is significantly reduced in absence of this amino acid.

TABLE 19

| Aβ peptide fragment | Binding |
| --- | --- |
| 1–28 | – |
| 1–43 | – |
| 22–35 | – |
| 1–36 | + |
| 1–37 | + |
| 1–38 | ++ |
| 1–39 | ++ |
| 17–42 | +++ |
| 1–42 | +++ |
| 17–40 | ++++ |
| 1–40 | ++++ |

"–" indicates no binding;
"+" indicates very low binding;
"++" indicates medium binding;
"+++" indicates strong binding; and
"++++" indicates very strong binding.

Based on data shown above, the epitope that antibody 2294 binds seems to include amino acids 26-34 and 40. Antibody 2294 binds to an epitope very similar to antibody 6G described in U.S. provisional application Ser. No. 60/676,093 (the amino acid and nucleic acid sequences of this antibody is shown in SEQ ID NOS:36-39; vectors encoding 6G are deposited at American Type Culture Collection on Jun. 15, 2005, with accession numbers PTA-6786 and PTA-6787). The epitope that antibody 6G binds includes amino acids from 25 to 34, and 40. The epitope comparison of antibody 2294 and 6G are shown in FIG. 14.

The binding affinity of antibody 6G Fab fragment to $A\beta_{1-40}$, $A\beta_{1-42}$, or $A\beta_{22-37}$ was measured using Biacore. Biotinylated $A\beta_{1-40}$, $A\beta_{1-42}$, or $A\beta_{22-37}$ was immobilized on a streptavidin chip, and 6G Fab was flowed onto it. Antibody 6G Fab fragment binds to $A\beta_{1-40}$ with $k_{on}$ (1/Ms) of $3.0\times10^5$, $k_{off}$ (1/s) of $7.0\times10^{-4}$, and $K_D$ of 2 nM. Antibody 6G Fab fragment binds to $A\beta_{1-42}$ with $k_{on}$ (1/Ms) of $1.8\times10^4$, $k_{off}$ (1/s) of $1.6\times10^{-3}$, and $K_D$ of 80 nM. Antibody 6G Fab fragment binds to $A\beta_{22-37}$ with $k_{on}$ (1/Ms) of $3.6\times10^5$, $k_{off}$ (1/s) of $3.9\times10^{-3}$, and $K_D$ of 11 nM. Antibody 6G has significant higher affinity to $A\beta_{1-42}$, and $A\beta_{22-37}$ than antibody 2294. Data indicate that binding of antibody 6G is less dependent on amino acid 40 than antibody 2294.

Antibody competition experiments between 2294, 6G, 2H6, and 2289 using Biacore assay were performed as described in Example 3. Competition experiments were performed using Biacore assay. Antibody 2294, 6G, 2H6, and 2289 were immobilized on different channels of a CM5 chip. CM5 chip channels were activated with N-ethyl-N'-(3-dimethylaminopropyl)-carbodiimide hydrochloride (EDC) and N-hydroxysuccinimide (NHS) according to the supplier's instructions. Antibody 2294, 6G, 2H6, and 2289 were each diluted into 10 mM sodium acetate pH 4.0 and injected over an activated chip at a concentration of 0.005 mg/mL. Each channel was blocked with ethanolamine. $A\beta_{1-40}$ peptide (150 uM) was flowed onto the chip for 2 min. Then antibody 2294 (to be tested for competition of binding) at 0.6 uM was flowed onto the chip for 1 min. HBS-EP buffer (0.01M HEPES, pH 7.4, 0.15 M NaCl, 3 mM EDTA, 0.005% Surfactant P20) was used as running buffer for all the BIAcore assays. After measuring binding of $A\beta_{1-40}$, all channels of the chip were regenerated by washing twice with a mixture of Pierce elution buffer (Product No. 21004, Pierce Biotechnology, Rockford, Ill.) and 4 M NaCl (2:1) for 6 sec. Competition binding was then performed for antibody 6G, 2H6, and then antibody 2289. Competition between 2294 and 6G and between 2294 and 2H6 for binding to $A\beta_{1-40}$ was observed, but no competition was observed between 2294 and 2289 or between 6G and 2289. Observations of competition between the antibody immobilized and the same antibody flowed onto the chip served as the positive control. Data indicate that antibody 2294 competes with 2H6 and 6G for binding to $A\beta_{1-40}$.

Example 8

Effect of Antibody 2294 and Deglycosylated Antibody 2294 in Reducing Aβ Deposit and Cognition in Animal Model of Alzheimer's Disease Deglycosylated antibody 2294 was prepared as by incubating purified antibody 2294 at 37° C. for 7 days with peptide-N-glycosidase F (Prozyme, 0.05 U per mg of antibody) in 20 mM Tris-HCl pH 8.0. Completeness of deglycosylation was verified by MALDI-TOF-MS and protein gel electrophoresis. Deglycosylated antibodies were purified by Protein A chromatography and endotoxin was removed by Q-Sepharose. The binding affinity to $A\beta_{1-40}$ of the deglycosylated 2294 was tested using Biacore assay described above, and the binding affinity of the deglycosylated 2294 to $A\beta_{1-40}$ was found to be identical to the intact antibody 2294.

Antibody 2294 and deglycosylated 2294 were tested in transgenic mice APP Tg2576 for effect on reversal of cognitive deficits, histological symptoms, and microhemorrhage as described in Example 4. For the sixteen weeks treatment study, transgenic mice (aged 20 months) were assigned to were assigned to one of the four groups. The first group received weekly intraperitoneal anti-Aβ antibody 2294 injections for a period of 16 weeks (n=4). The second group received weekly intraperitoneal deglycosylated anti-Aβ antibody 2294 injections for a period of 16 weeks (n=5). The third group received weekly intraperitoneal anti-AMN antibody (2906; mouse-monoclonal anti-*Drosophila* amnesiac protein IgG1) injections for a period of 16 weeks (n=6). Non-transgenic littermates were treated for 16 weeks with either anti-AMN antibody (n=4) or 2294 (n=2).

Histological and behavioral analysis are performed as described in Example 4.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

DEPOSIT OF BIOLOGICAL MATERIAL

The following materials have been deposited with the American Type Culture Collection, 10801 University Boulevard, Manassas, Va. 20110-2209, USA (ATCC):

| Material | Antibody No. | ATCC Accession No. | Date of Deposit |
|---|---|---|---|
| pDb.9TL.hFc2a | 9TL heavy chain | PTA-6124 | Jul. 20, 2004 |
| pEb.9TL.hK | 9TL light chain | PTA-6125 | Jul. 20, 2004 |
| pDb.6G.hFc2a | 6G heavy chain | PTA-6786 | Jun. 15, 2005 |
| pEb.6G.hK | 6G light chain | PTA-6787 | Jun. 15, 2005 |

Vector pEb.9TL.hK is a polynucleotide encoding the 9TL light chain variable region and the light chain kappa constant region; and vector pDb.9TL.hFc2a is a polynucleotide encoding the 9TL heavy chain variable region and the heavy chain IgG2a constant region containing the following mutations: A330P331 to S330S331 (amino acid numbering with reference to the wildtype IgG2a sequence; see *Eur. J. Immunol.* (1999) 29:2613-2624).

Vector pEb.6G.hK is a polynucleotide encoding the 6G light chain variable region and the light chain kappa constant region; and vector pDb.6G.hFc2a is a polynucleotide encoding the 6G heavy chain variable region and the heavy chain IgG2a constant region containing the following mutations: A330P331 to S330S331 (amino acid numbering with reference to the wildtype IgG2a sequence; see *Eur. J. Immunol.* (1999) 29:2613-2624).

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Rinat Neuroscience Corp. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 886OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

```
Antibody sequences
9TL heavy chain variable region amino acid sequence          (SEQ ID NO: 1)
QVQLVQSGAEVKKPGASVKVSCKASGYYTEAYYIHWVRQAPGQGLEWMGRIDPAT
GNTKYAPRLQDRVTMTRDTSTSTVYMELSSLRSEDTAVYYCASLYSLPVYWGQGTT
VTVSS 9TL light chain variable region amino acid sequence          (SEQ ID NO: 2)
DVVMTQSPLSLPVTLGQPASISCKSSQSLLYSDAKTYLNWFQQRPGQSPRRLIYQISRL
DPGVPDRFSGSGSGTDFTLKISRVEAEDVGVYYCLQGTHYPVLFGQGTRLEIKRT 9TL CDR H1 (extended CDR)                                    (SEQ ID NO: 3)
GYYTEAYYIH 9TL CDR H2 (extended CDR)                                    (SEQ ID NO: 4)
RIDPATGNTKYAPRLQD 9TL CDR H3 (extended CDR)                                    (SEQ ID NO: 5)
LYSLPVY 9TL CDR L1 (extended CDR)                                    (SEQ ID NO: 6)
KSSQSLLYSDAKTYLN 9TL CDR L2 (extended CDR)                                    (SEQ ID NO: 7)
QISRLDP 9TL CDR L3 (extended CDR)                                    (SEQ ID NO: 8)
LQGTHYPVL
```

9TL heavy chain variable region nucleotide sequence                (SEQ ID NO: 9)
CAGGTGCAGCTGGTGCAGTCTGGTGCTGAGGTGAAGAAGCCTGGCGCTTCCGTGA
AGGTTTCCTGCAAAGCATCTGGTTACTATACGGAGGCTTACTATATCCACTGGGTG
CGCCAAGCCCCTGGTCAAGGCCTGGAGTGGATGGGCAGGATTGATCCTGCGACTG
GTAATACTAAATATGCCCCGAGGTTACAGGACCGGGTGACCATGACTCGCGATAC
CTCCACCAGCACTGTCTACATGGAACTGAGCTCTCTGCGCTCTGAGGACACTGCTG
TGTATTACTGTGCCTCCCTTTATAGTCTCCCTGTCTACTGGGGCCAGGGTACCACT
GTTACCGTGTCCTCT 9TL light chain variable region nucleotide sequence                (SEQ ID NO: 10)
GATGTTGTGATGACCCAGTCCCCACTGTCTFFTGCCAGTTACCCTGGGACAACCAG
CCTCCATATCTTGCAAGTCAAGTCAGAGCCTCTTATATAGTGATGCCAAGACATA
TTTGAATTGGTTCCAACAGAGGCCTGGCCAGTCTCCACGCCGCCTAATCTATCAG
ATTTCCCGGCTGGACCCTGGCGTGCCTGACAGGTTCAGTGGCAGTGGATCAGGCA
CAGATTTTACACTTAAAATCAGCAGAGTGGAGGCTGAAGATGTGGGAGTTTATTA
CTGCTTACAAGGTACACATTATCCGGTGCTCTTCGGTCAAGGGACCCGCCTGGAG
ATCAAACGCACT 9TL heavy chain full antibody amino acid sequence                (SEQ ID NO: 11)
(including modified IgG2a as described herein)
QVQLVQSGAEVKKPGASVKVSCKASGYYTEAYYIHWVRQAPGQGLEWMGRIDPAT
GNTKYAPRLQDRVTMTRDTSTSTVYMELSSLRSEDTAVYYCASLYSLPVYWGQGTT
VTVSSASTKGPSVFPLAPCSRSTSESTAALGCLVKDYFPEPVTVSWNSGALTSGVHTFP
AVLQSSGLYSLSSVVTVPSSNFGTQTYTCNVDHKPSNTKVDKTVERKCCVECPPCPAP
PVAGPSVFLFPPKPKDTLMISRTPEVTCVVVDVSHEDPEVQFNWYVDGVEVHNAKTK
PREEQFNSTFRVVSVLTVVHQDWLNGKEYKCKVSNKGLPSSIEKTISKTKGQPREPQV
YTLPPSREEMTKNQVSLTCLVKGFYPSDIAVEWESNGQPENNYKTTPPMLDSDGSFFL
YSKLTVDKSRWQQGNVFSCSVMHEALHNHYTQKSLSLSPGK 9TL light chain full antibody amino acid sequence                (SEQ ID NO: 12)
DVVMTQSPLSLPVTLGQPASISCKSSQSLLYSDAKTYLNWFQQRPGQSPRRLIYQISR
LDPGVPDRFSGSGSGTDFTLKISRVEAEDVGVYYCLQGTHYPVLFGQGTRLEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC 9TL heavy chain full antibody nucleotide sequence                (SEQ ID NO: 13)
(including modified IgG2a as described herein)
CAGGTGCAGCTGGTGCAGTCTGGTGCTGAGGTGAAGAAGCCTGGCGCTTCCGTGA
AGGTTTCCTGCAAAGCATCTGGTTACTATACGGAGGCTTACTATATCCACTGGGT
GCGCCAAGCCCCTGGTCAAGGCCTGGAGTGGATGGGCAGGATTGATCCTGCGACT
GGTAATACTAAATATGCCCCGAGGTTACAGGACCGGGTGACCATGACTCGCGATA
CCTCCACCAGCACTGTCTACATGGAACTGAGCTCTCTGCGCTCTGAGGACACTGC
TGTGTATTACTGTGCCTCCCTTTATAGTCTCCCTGTCTACTGGGGCCAGGGTACCA
CTGTTACCGTGTCCTCTGCCTCCACCAAGGGCCCATCTGTCTTCCCACTGGCCCCA
TGCTCCCGCAGCACCTCCGAGAGCACAGCCGCCCTGGGCTGCCTGGTCAAGGACT
ACTTCCCAGAACCTGTGACCGTGTCCTGGAACTCTGGCGCTCTGACCAGCGGCGT
GCACACCTTCCCAGCTGTCCTGCAGTCCTCAGGTCTCTACTCCCTCAGCAGCGTGG
TGACCGTGCCATCCAGCAACTTCGGCACCCAGACCTACACCTGCAACGTAGATCA
CAAGCCAAGCAACACCAAGGTCGACAAGACCGTGGAGAGAAAGTGTTGTGTGGA
GTGTCCACCTTGTCCAGCCCCTCCAGTGGCCGGACCATCCGTGTTCCTGTTCCCTC
CAAAGCCAAAGGACACCCTGATGATCTCCAGAACCCCAGAGGTGACCTGTGTGGT
GGTGGACGTGTCCCACGAGGACCCAGAGGTGCAGTTCAACTGGTATGTGGACGG
AGTGGAGGTGCACAACGCCAAGACCAAGCCAAGAGAGGAGCAGTTCAACTCCAC
CTTCAGAGTGGTGAGCGTGCTGACCGTGGTGCACCAGGACTGGCTGAACGGAAA
GGAGTATAAGTGTAAGGTGTCCAACAAGGGACTGCCATCCAGCATCGAGAAGAC
CATCTCCAAGACCAAGGGACAGCCAAGAGAGCCACAGGTGTATACCCTGCCCCC
ATCCAGAGAGGAGATGACCAAGAACCAGGTGTCCCTGACCTGTCTGGTGAAGGG
ATTCTATCCATCCGACATCGCCGTGGAGTGGGAGTCCAACGGACAGCCAGAGAAC
AACTATAAGACCACCCCTCCAATGCTGGACTCCGACGGATCCTTCTTCCTGTATTC
CAAGCTGACCGTGGACAAGTCCAGATGGCAGCAGGGAAACGTGTTCTCTTGTTCC
GTGATGCACGAGGCCCTGCACAACCACTATACCCAGAAGAGCCTGTCCCTGTCTC
CAGGAAAGTAATTCTAGA 9TL light chain full antibody nucleotide sequence                (SEQ ID NO: 14)
GATGTTGTGATGACCCAGTCCCCACTGTCTTTGCCAGTTACCCTGGGACAACCAG
CCTCCATATCTTGCAAGTCAAGTCAGAGCCTCTTATATAGTGATGCCAAGACATA
TTTGAATTGGTTCCAACAGAGGCCTGGCCAGTCTCCACGCCGCCTAATCTATCAG
ATTTCCCGGCTGGACCCTGGCGTGCCTGACAGGTTCAGTGGCAGTGGATCAGGCA
CAGATTTTACACTTAAAATCAGCAGAGTGGAGGCTGAAGATGTGGGAGTTTATTA
CTGCTTACAAGGTACACATTATCCGGTGCTCTTCGGTCAAGGGACCCGCCTGGAG
ATCAAACGCACTGTGGCTGCACCATCTGTCTTCATCTTCCCTCCATCTGATGAGCA
GTTGAAATCCGGAACTGCCTCTGTTGTGTGCCTGCTGAATAACTTCTATCCACGCG
AGGCCAAAGTACAGTGGAAGGTGGATAACGCCCTCCAATCCGGTAACTCCCAGG
AGAGTGTCACAGAGCAGGACAGCAAGGACAGCACCTACAGCCTCAGCAGCACCC
TGACCCTGAGCAAAGCAGACTACGAGAAACACAAAGTCTACGCCTGCGAAGTCA
CCCATCAGGGCCTGAGTTCTCCAGTCACAAAGAGCTTCAACCGCGGTGAGTGCTA
ATTCTAG 6G heavy chain variable region amino acid sequence (SEQ ID NO: 26)
QVQLVQSGAEVKKPGASVKVSCKASGYTFTTYAIHWVRQ
APGQGLEWMGFTSPYSGVSNYNQKFKGRVTMTRDTSTST
VYMELSSLRSEDTAVYYCARFDNYDRGYVRDYWGQGTLV
TVS 6G light chain variable region amino acid sequence (SEQ ID NO: 27)
DIVMTQSPDSLAVSLGERATINCRASESVDNDRISFLNW
YQQKPGQPPKLLIYAATKQGTGVPDRFSGSGSGTDFTLT
ISSLQAEDVAVYYCQQSKEFPWSFGGGTKVEIKRTV 6G CDR H1 (extended CDR) (SEQ ID NO: 28)
GYTFTTYAIH 6G CDR H2 (extended CDR) (SEQ ID NO: 29)
FTSPYSGVSNYNQKFKG 6G CDR H3 (extended CDR) (SEQ ID NO: 30)
FDNYDRGYVRDY 6G CDR L1 (extended CDR) (SEQ ID NO: 31)
RASESVDNDRISFLN 6G CDR L2 (extended CDR) (SEQ ID NO: 32)
AATKQGT 6G CDR L3 (extended CDR) (SEQ ID NO: 33)
QQSKEFPWS 6G heavy chain variable region nucleotide sequence (SEQ ID NO: 34)
CAGGTGCAACTGGTGCAATCCGGTGCCGAGGTGAAAAAGCCAGGCGCCTCCGTGA
AAGTGTCCTGCAAAGCCTCCGGTTACACCTTTACCACCTATGCCATCCATTGGGTG
CGCCAGGCCCCAGGCCAGGGTCTGGAGTGGATGGGCTTTACTTCCCCCTACTCCG
GGGTGTCGAATTACAATCAGAAGTTCAAAGGCCGCGTCACCATGACCCGCGACAC
CTCCACCTCCACAGTGTATATGGAGCTGTCCTCTCTGCGCTCCGAAGACACCGCCG
TGTATTACTGTGCCCGCTTCGACAATTACGATCGCGGCTATGTGCGTGACTATTGG
GGCCAGGGCACCCTGGTCACCGTCTCC 6G light chain variable region nucleotide sequence (SEQ ID NO: 35)
GACATCGTGATGACCCAGTCCCCAGACTCCCTGGCCGTGTCCCTGGGCGAGCGCG
CCACCATCAACTGCCGCGCCAGCGAATCCGTGGATAACGATCGTATTTCCTTTCT
GAACTGGTACCAGCAGAAACCAGGCCAGCCTCCTAAGCTGCTCATTTACGCCGC
CACCAAACAGGGTACCGGCGTGCCTGACCGCTTCTCCGGCAGCGGTTCCGGCAC
CGATTTCACTCTGACCATCTCCTCCCTGCAGGCCGAAGATGTGGCAGTGTATTAC
TGTCAGCAGTCCAAAGAGTTTCCTGGTCCTTTGGCGGTGGCACCAAGGTGGAGA
TCAAACGCACTGTG 6G heavy chain full antibody amino acid sequence (SEQ ID NO: 36)
(including modified IgG2 aas described herein)
QVQLVQSGAEVKKPGASVKVSCKASGYTFTTYAIHWVRQAPGQGLEWMGFTSPYSG
VSNYNQKFKGRVTMTRDTSTSTVYMELSSLRSEDTAVYYCARFDNYDRGYVRDYW
GQGTLVTVSSASTKGPSVFPLAPCSRSTSESTAALGCLVKDYFPEPVTVSWNSGALTS
GVHTFPAVLQSSGLYSLSSVVTVPSSNFGTQTYTCNVDHKPSNTKVDKTVERKCCVE
CPPCPAPPVAGPSVFLFPPKPKDTLMISRTPEVTCVVVDVSHEDPEVQFNWYVDGVEV
HNAKTKPREEQFNSTFRVVSVLTVVHQDWLNGKEYKCKVSNKGLPSSIEKTISKTKG
QPREPQVYTLPPSREEMTKNQVSLTCLVKGFYPSDIAVEWESNGQPENNYKTTPPML
DSDGSFFLYSKLTVDKSRWQQGNVFSCSVMHEALHNHYTQKSLSLSPGK 6G light chain full antibody amino acid sequence (SEQ ID NO: 37)
DIVMTQSPDSLAVSLGERATINCRASESVDNDRISFLNWYQQKPGQPPKLLIYAATK
QGTGVPDRFSGSGSGTDFTLTISSLQAEDVAVYYCQQSKEFPWSFGGGTKVEIKRTV
AAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC 6G heavy chain full antibody nucleotide sequence (SEQ ID NO: 38)
(including modified IgG2 aas described herein)
CAGGTGCAACTGGTGCAATCCGGTGCCGAGGTGAAAAAGCCAGGCGCCTCCGTG
AAAGTGTCCTGCAAAGCCTCCGGTTACACCTTTACCACCTATGCCATCCATTGGGT
GCGCCAGGCCCCAGGCCAGGGTCTGGAGTGGATGGGCTTTACTTCCCCCTACTCC
GGGGTGTCGAATTACAATCAGAAGTTCAAAGGCCGCGTCACCATGACCCGCGAC
ACCTCCACCTCCACAGTGTATATGGAGCTGTCCTCTCTGCGCTCCGAAGACACCG
CCGTGTATTACTGTGCCCGCTTCGACAATTACGATCGCGGCTATGTGCGTGACTAT
TGGGGCCAGGGCACCCTGGTCACCGTCTCCTCAGCCTCCACCAAGGGCCCATCTG
TCTTTCCCACTGGCCCCATGCTCCCGCAGCACCTCCGAGAGCACAGCCGCCCTGGG
CTGCCTGGTCAAGGACTACTTCCCAGAACCTGTGACCGTGTCCTGGAACTCTGGC
GCTCTGACCAGCGGCGTGCACACCTTCCCAGCTGTCCTGCAGTCCTCAGGTCTCTA
CTCCCTCAGCAGCGTGGTGACCGTGCCATCCAGCAACTTCGGCACCCAGACCTAC
ACCTGCAACGTAGATCACAAGCCAAGCAACACCAAGGTCGACAAGACCGTGGAG
AGAAAGTGTTGTGTGGAGTGTCCACCTTGTCCAGCCCCTCCAGTGGCCGGACCAT -continued

```
CCGTGTTCCTGTTCCCTCCAAAGCCAAAGGACACCCCTGATGATCTCCAGAACCCC
AGAGGTGACCTGTGTGGTGGTGGACGTGTCCCACGAGGACCCAGAGGTGCAGTTC
AACTGGTATGTGGACGGAGTGGAGGTGCACAACGCCAAGACCAAGCCAAGAGAG
GAGCAGTTCAACTCCACCTTCAGAGTGGTGAGCGTGCTGACCGTGGTGCACCAGG
ACTGGCTGAACGGAAAGGAGTATAAGTGTAAGGTGTCCAACAAGGGACTGCCAT
CCAGCATCGAGAAGACCATCTCCAAGACCAAGGGACAGCCAAGAGAGCCACAGG
TGTATACCCTGCCCCCATCCAGAGAGGAGATGACCAAGAACCAGGTGTCCCTGAC
CTGTCTGGTGAAGGGATTCTATCCATCCGACATCGCCGTGGAGTGGGAGTCCAAC
GGACAGCCAGAGAACAACTATAAGACCACCCCTCCAATGCTGGACTCCGACGGA
TCCTTCTTCCTGTATTCCAAGCTGACCGTGGACAAGTCCAGATGGCAGCAGGGAA
ACGTGTTCTCTTGTTCCGTGATGCACGAGGCCCTGCACAACCACTATACCCAGAA
GAGCCTGTCCCTGTCTCCAGGAAAG
```

<u>6G light chain full antibody nucleotide sequence</u>            (SEQ ID NO: 39)
```
GACATCGTGATGACCCAGTCCCCAGACTCCCTGGCCGTGTCCCTGGGCGAGCGCG
CCACCATCAACTGCCGCGCCAGCGAATCCGTGGATAACGATCGTATTTCCTTTCTG
AACTGGTACCAGCAGAAACCAGGCCAGCCTCCTAAGCTGCTCATTTACGCCGCCA
CCAAACAGGGTACCGGCGTGCCTGACCGCTTCTCCGGCAGCGGTTCCGGCACCGA
TTTCACTCTGACCATCTCCTCCCTGCAGGCCGAAGATGTGGCAGTGTATTACTGTC
AGCAGTCCAAAGAGTTTCCCTGGTCCTTTGGCGGTGGCACCAAGGTGGAGATCAA
ACGCACTGTGGCTGCACCATCTGTCTTCATCTTCCCTCCATCTGATGAGCAGTTGA
AATCCGGAACTGCCTCTGTTGTGTGCCTGCTGAATAACTTCTATCCACGCGAGGCC
AAAGTACAGTGGAAGGTGGATAACGCCCTCCAATCCGGTAACTCCCAGGAGAGT
GTCACAGAGCAGGACAGCAAGGACAGCACCTACAGCCTCAGCAGCACCCTGACC
CTGAGCAAAGCAGACTACGAGAAACACAAAGTCTACGCCTGCGAAGTCACCCAT
CAGGGCCTGAGTTCTCCAGTCACAAAGAGCTTCAACCGCGGTGAGTGC
```

---

The claimed invention is:

1. A method for treating a disease characterized by aberrant deposition of β-amyloid in a subject, comprising administering to the subject an effective amount of an antibody that specifically binds to a β-amyloid peptide or an aggregated form of a β-amyloid peptide(Aβ), wherein the antibody comprises a heavy chain variable region comprising:
   (a) a CDR1 comprising the amino acid sequence of SEQ ID NO:3;
   (b) a CDR2 comprising the amino acid sequence of SEQ ID NO:4; and
   (c) a CDR3 comprising the amino acid sequence of SEQ ID NO:5;
and a light chain variable region comprising:
   (d) a CDR1 comprising the amino acid sequence of SEQ ID NO:6;
   (e) a CDR2 comprising the amino acid sequence of SEQ ID NO:7; and
   (f) a CDR3 comprising the amino acid sequence of SEQ ID NO:8.

2. The method of claim 1, wherein the subject is a human.

3. The method of claim 1, wherein the disease is Alzheimer's disease.

4. The method of claim 1, wherein the antibody is a monoclonal antibody.

5. The method of claim 1, wherein the antibody is a humanized antibody.

6. The method of claim 1, wherein the antibody is a human antibody.

7. The method of claim 1, wherein the antibody binds to the Aβ peptide with a $K_D$ of about 100 nM or less.

8. The method of claim 1, wherein the antibody binds to the Aβ peptide with a $K_D$ of about 20 nM or less.

9. The method of claim 1, wherein the antibody binds to the Aβ peptide with a $K_D$ of about 2 nM or less.

10. The method of claim 1, wherein the antibody binds to the C-terminus of the Aβ peptide.

11. The method of claim 1, wherein the antibody specifically binds to an epitope within residues 28-40 of $A\beta_{1-40}$, 28-42 of $A\beta_{1-42}$, or 28-43 of $A\beta_{1-43}$.

12. The method of claim 1, wherein the antibody specifically binds to the C-terminus of the Aβ peptide selected from the group consisting of $A\beta_{1-36}$, $A\beta_{1-37}$, $A\beta_{1-38}$, $A\beta_{1-39}$, $A\beta_{1-40}$, $A\beta_{1-42}$, and $A\beta_{1-43}$.

13. The method of claim 1, wherein the antibody specifically binds to an epitope on $A\beta_{1-40}$ that includes amino acid 39 and/or 40.

14. The method of claim 13, wherein the antibody comprises a heavy chain variable region comprising the amino acid sequence of SEQ ID NO:1, and a light chain variable region comprising the amino acid sequence of SEQ ID NO:2.

15. The method of claim 1, wherein the antibody binds to $A\beta_{1-40}$ with higher affinity than to $A\beta_{1-42}$ or $A\beta_{1-43}$.

16. The method of claim 1, wherein the Fc region of the antibody is not N-glycosylated or has an N-glycosylation pattern that is altered with respect to a native Fc region.

17. The method of claim 1, wherein the Fc region of the antibody comprises a mutation within the N-glycosylation recognition sequence, whereby the Fc region is not N-glycosylated.

18. The method of claim 1, wherein the Fc region of the antibody is the Fc region of a human heavy chain IgG2a comprising the amino acid mutation from alanine to serine at position 330 and from proline to serine at position 331, wherein the amino acid position is based on Kabat numbering with reference to human wildtype IgG2a sequence.

19. The method of claim 1, wherein the antibody comprises an Fc region having impaired effector function.

20. The method of claim 1, wherein the heavy chain variable region comprises the amino acid sequence of SEQ ID NO:1.

21. The method of claim 20, wherein the light chain variable region comprises the amino acid sequence of SEQ ID NO:2.

22. The antibody of claim 21 wherein the Fc region of the method is the Fc region of a human heavy chain IgG2a comprising the amino acid mutation from alanine to serine at position 330 and from proline to serine at position 331, wherein the amino acid position is based on Kabat numbering with reference to human wildtype IgG2a sequence.

23. The method of claim 1, wherein the light chain variable region comprises the amino acid sequence of SEQ ID NO:2.

24. The method of claim 1, wherein the heavy chain comprises the amino acid sequence of SEQ ID NO:11.

25. The method of claim 24, wherein the light chain comprises the amino acid sequence of SEQ ID NO:12.

26. The method of claim 1, wherein the light chain comprises the amino acid sequence of SEQ ID NO:12.

27. The method of claim 1, wherein the heavy chain variable region amino acid sequence consists of the sequence of SEQ ID NO:1 and wherein the light chain variable region amino acid sequence consists of the sequence of SEQ ID NO:2.

28. The method of claim 1, wherein the heavy chain amino acid sequence consists of the sequence of SEQ ID NO:11 and wherein the light chain amino acid sequence consists of the sequence of SEQ ID NO:12.

29. The antibody of claim 28 wherein the Fc region of the method is the Fc region of a human heavy chain IgG2a comprising the amino acid mutation from alanine to serine at position 330 and from proline to serine at position 331, wherein the amino acid position is based on Kabat numbering with reference to human wildtype IgG2a sequence.

30. The method of claim 1, wherein the light chain variable region comprises the amino acid sequence of SEQ ID NO:2.

31. The method of claim 1, wherein the heavy chain comprises the amino acid sequence of SEQ ID NO:11.

32. The method of claim 31, wherein the light chain comprises the amino acid sequence of SEQ ID NO:12.

33. The method of claim 1, wherein the light chain comprises the amino acid sequence of SEQ ID NO:12.

34. A method for treating a disease associated with aberrant deposition of β-amyloid in a subject, comprising administering to the subject an effective amount of an antibody that specifically binds to a β-amyloid peptide or an aggregated form of a β-amyloid peptide, wherein the antibody comprises an Fc region with a variation from a naturally occurring Fc region, wherein the variation results in impaired effector function, and further wherein the antibody comprises a heavy chain variable region comprising:
- (a) a CDR1 comprising the amino acid sequence of SEQ ID NO:3;
- (b) a CDR2 comprising the amino acid sequence of SEQ ID NO:4; and
- (c) a CDR3 comprising the amino acid sequence of SEQ ID NO:5; and a light chain variable region comprising:
- (d) a CDR1 comprising the amino acid sequence of SEQ ID NO:6;
- (e) a CDR2 comprising the amino acid sequence of SEQ ID NO:7; and
- (f) a CDR3 comprising the amino acid sequence of SEQ ID NO:8.

35. The method of claim 34, wherein the administration of the antibody with the variation in the Fc region causes less cerebral microhemorrhage than administration of an antibody without the variation.

36. The method of claim 34, wherein the subject is a human.

37. The method of claim 34, wherein the disease is Alzheimer's disease.

38. The method of claim 34, wherein the antibody is a monoclonal antibody.

39. The method of claim 34, wherein the antibody is a humanized antibody.

40. The method of claim 34, wherein the antibody is a human antibody.

41. The method of claim 34, wherein the antibody binds to the Aβ peptide with a $K_D$ of about 100 nM or less.

42. The method of claim 34, wherein the antibody binds to the Aβ peptide with a $K_D$ of about 20 nM or less.

43. The method of claim 34, wherein the antibody binds to the Aβ peptide with a $K_D$ of about 2 nM or less.

44. The method of claim 34, wherein the antibody specifically binds to an epitope within residues 28-40 of $A\beta_{1-40}$, 28-42 of $A\beta_{1-42}$, or 28-43 of $A\beta_{1-43}$.

45. The method of claim 34, wherein the antibody specifically binds to the C-terminus of the Aβ peptide selected from the group consisting of $A\beta_{1-36}$, $A\beta_{1-37}$, $A\beta_{1-38}$, $A\beta_{1-39}$, $A\beta_{1-40}$, $A\beta_{1-42}$, and $A\beta_{1-43}$.

46. The method of claim 34, wherein the antibody specifically binds to an epitope on $A\beta_{1-40}$ that includes amino acid 39 and/or 40.

47. The method of claim 46, wherein the antibody comprises a heavy chain variable region comprising the amino acid sequence of SEQ ID NO:1, and a light chain variable region comprising the amino acid sequence of SEQ ID NO:2.

48. The method of claim 34, wherein the antibody binds to $A\beta_{1-40}$ with higher affinity than to $A\beta_{1-42}$ or $A\beta_{1-43}$.

49. The method of claim 34, wherein the Fc region of the antibody is not N-glycosylated or has an N-glycosylation pattern that is altered with respect to a native Fc region.

50. The method of claim 34, wherein the Fc region of the antibody comprises a mutation within the N-glycosylation recognition sequence, whereby the Fc region is not N-glycosylated.

51. The method of claim 34, wherein the Fc region of the antibody is the Fc region of a human heavy chain IgG2a comprising the amino acid mutation from alanine to serine at position 330 and from proline to serine at position 331, wherein the amino acid position is based on Kabat numbering with reference to human wildtype IgG2a sequence.

52. The method of claim 34, wherein the heavy chain variable region comprises the amino acid sequence of SEQ ID NO:1.

53. The method of claim 52, wherein the light chain variable region comprises the amino acid sequence of SEQ ID NO:2.

54. The method of claim 34, wherein the heavy chain variable region amino acid sequence consists of the sequence of SEQ ID NO:1 and wherein the light chain variable region amino acid sequence consists of the sequence of SEQ ID NO:2.

55. The method of claim 34, wherein the heavy chain amino acid sequence consists of the sequence of SEQ ID NO:11 and wherein the light chain amino acid sequence consists of the sequence of SEQ ID NO:12.

56. A method for treating Alzheimers disease in a subject, comprising administering to the subject an effective amount of an antibody that specifically binds to a β-amyloid peptide, wherein the antibody comprises a heavy chain variable region comprising:
- (a) a CDR1 comprising the amino acid sequence of SEQ ID NO:3;
- (b) a CDR2 comprising the amino acid sequence of SEQ ID NO:4; and
- (c) a CDR3 comprising the amino acid sequence of SEQ ID NO:5; and a light chain variable region comprising:
- (d) a CDR1 comprising the amino acid sequence of SEQ ID NO:6;
- (e) a CDR2 comprising the amino acid sequence of SEQ ID NO:7; and
- (f) a CDR3 comprising the amino acid sequence of SEQ ID NO:8.

57. The method of claim 56, wherein the heavy chain variable region comprises the amino acid sequence of SEQ ID NO:1.

58. The method of claim 57, wherein the light chain variable region comprises the amino acid sequence of SEQ ID NO:2.

59. The antibody of claim 58 wherein the Fc region of the method is the Fc region of a human heavy chain IgG2a comprising the amino acid mutation from alanine to serine at position 330 and from proline to serine at position 331, wherein the amino acid position is based on Kabat numbering with reference to human wildtype IgG2a sequence.

60. The method of claim 56 wherein the light chain variable region comprises the amino acid sequence of SEQ ID NO:2.

61. The method of claim 56, wherein the heavy chain comprises the amino acid sequence of SEQ ID NO:11.

62. The method of claim 61, wherein the light chain comprises the amino acid sequence of SEQ ID NO:12.

63. The method of claim 56, wherein the light chain comprises the amino acid sequence of SEQ ID NO:12.

64. The method of claim 56, wherein the heavy chain variable region amino acid sequence consists of the sequence of SEQ ID NO:1 and wherein the light chain variable region amino acid sequence consists of the sequence of SEQ ID NO:2.

65. The antibody of claim 64 wherein the Fc region of the method is the Fc region of a human heavy chain IgG2a comprising the amino acid mutation from alanine to serine at position 330 and from proline to serine at position 331, wherein the amino acid position is based on Kabat numbering with reference to human wildtype IgG2a sequence.

66. The method of claim 56, wherein the heavy chain amino acid sequence consists of the sequence of SEQ ID NO:11 and wherein the light chain amino acid sequence consists of the sequence of SEQ ID NO:12.

67. The antibody of claim 56, wherein the method specifically binds to an epitope on $A\beta_{1-40}$ that includes amino acid 39 and/or 40.

68. The method of claim 56, wherein the antibody binds to $A\beta_{1-40}$ with higher affinity than to $A\beta_{1-42}$ or $A\beta_{1-43}$.

* * * * *

SEQUENCE LISTING

<160> NUMBER OF SEQ ID NOS: 53

<210> SEQ ID NO 1
<211> LENGTH: 116
<212> TYPE: PRT
<213> ORGANISM: Artificial Sequence
<220> FEATURE:
<223> OTHER INFORMATION: Synthetic construct

<400> SEQUENCE: 1

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Tyr Thr Glu Ala Tyr
            20                  25                  30

Tyr Ile His Trp Val Arg Gln Ala Pro Gly Gln Gly Leu Glu Trp Met
        35                  40                  45

Gly Arg Ile Asp Pro Ala Thr Gly Asn Thr Lys Tyr Ala Pro Arg Leu
    50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Tyr Ser Leu Pro Val Tyr Trp Gly Gln Gly Thr Thr Val
            100                 105                 110

Thr Val Ser Ser
        115

<210> SEQ ID NO 2
<211> LENGTH: 114
<212> TYPE: PRT
<213> ORGANISM: Artificial Sequence
<220> FEATURE:
<223> OTHER INFORMATION: Synthetic construct

<400> SEQUENCE: 2

-continued

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Ala Lys Thr Tyr Leu Asn Trp Phe Gln Gln Arg Pro Gly Gln Ser
        35                  40                  45

Pro Arg Arg Leu Ile Tyr Gln Ile Ser Arg Leu Asp Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Tyr Pro Val Leu Phe Gly Gln Gly Thr Arg Leu Glu Ile Lys
            100                 105                 110

Arg Thr
```

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

```
Gly Tyr Tyr Thr Glu Ala Tyr Tyr Ile His
1               5                   10
```

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

```
Arg Ile Asp Pro Ala Thr Gly Asn Thr Lys Tyr Ala Pro Arg Leu Gln
1               5                   10                  15

Asp
```

<210> SEQ ID NO 5
<211> LENGTH: 7
<212> TYPE: PRT
<213> ORGANISM: Artificial Sequence
<220> FEATURE:
<223> OTHER INFORMATION: Synthetic construct

<400> SEQUENCE: 5

```
Leu Tyr Ser Leu Pro Val Tyr
1               5
```

<210> SEQ ID NO 6
<211> LENGTH: 16
<212> TYPE: PRT
<213> ORGANISM: Artificial Sequence
<220> FEATURE:
<223> OTHER INFORMATION: Synthetic construct

<400> SEQUENCE: 6

```
Lys Ser Ser Gln Ser Leu Leu Tyr Ser Asp Ala Lys Thr Tyr Leu Asn
1               5                   10                  15
```

<210> SEQ ID NO 7

<210> SEQ ID NO 7
<211> LENGTH: 7
<212> TYPE: PRT
<213> ORGANISM: Artificial Sequence
<220> FEATURE:
<223> OTHER INFORMATION: Synthetic construct

<400> SEQUENCE: 7

Gln Ile Ser Arg Leu Asp Pro
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic construct

<400> SEQUENCE: 8

Leu Gln Gly Thr His Tyr Pro Val Leu
 1               5

<210> SEQ ID NO 9
<211> LENGTH: 348
<212> TYPE: DNA
<213> ORGANISM: Artificial Sequence
<220> FEATURE:
<223> OTHER INFORMATION: Synthetic construct

<400> SEQUENCE: 9
caggtgcagc tggtgcagtc tggtgctgag gtgaagaagc ctggcgcttc cgtgaaggtt        60
tcctgcaaag catctggtta ctatacggag gcttactata tccactgggt gcgccaagcc       120
cctggtcaag gcctggagtg gatgggcagg attgatcctg cgactggtaa tactaaatat       180
gccccgaggt tacaggaccg ggtgaccatg actcgcgata cctccaccag cactgtctac       240
atggaactga gctctctgcg ctctgaggac actgctgtgt attactgtgc ctcccttat        300 agtctccctg tctactgggg ccagggtacc actgttaccg tgtcctct                    348

<210> SEQ ID NO 10
<211> LENGTH: 342
<212> TYPE: DNA
<213> ORGANISM: Artificial Sequence
<220> FEATURE:
<223> OTHER INFORMATION: Synthetic construct

<400> SEQUENCE: 10
gatgttgtga tgacccagtc cccactgtct ttgccagtta ccctgggaca accagcctcc        60
atatcttgca agtcaagtca gagcctctta tatagtgatg ccaagacata tttgaattgg       120
ttccaacaga ggcctggcca gtctccacgc cgcctaatct atcagatttc ccggctggac       180
cctggcgtgc ctgacaggtt cagtggcagt ggatcaggca cagatttac acttaaaatc        240 agcagagtgg aggctgaaga tgtgggagtt tattactgct acaaggtac acattatccg        300 gtgctcttcg gtcaagggac cgcctggag atcaaacgca ct                           342

<210> SEQ ID NO 11
<211> LENGTH: 442
<212> TYPE: PRT
<213> ORGANISM: Artificial Sequence
<220> FEATURE:
<223> OTHER INFORMATION: Synthetic construct

<400> SEQUENCE: 11

Gln Val Gln Leu Val Gln Ser Gly Ala Glu Val Lys Lys Pro Gly Ala

-continued

```
  1               5                  10                  15
Ser Val Lys Val Ser Cys Lys Ala Ser Gly Tyr Tyr Thr Glu Ala Tyr
                20                  25                  30

Tyr Ile His Trp Val Arg Gln Ala Pro Gly Gln Gly Leu Glu Trp Met
                35                  40                  45

Gly Arg Ile Asp Pro Ala Thr Gly Asn Thr Lys Tyr Ala Pro Arg Leu
                50                  55                  60

Gln Asp Arg Val Thr Met Thr Arg Asp Thr Ser Ser Thr Val Tyr
 65                 70                  75                  80

Met Glu Leu Ser Ser Leu Arg Ser Glu Asp Thr Ala Val Tyr Tyr Cys
                85                  90                  95

Ala Ser Leu Tyr Ser Leu Pro Val Tyr Trp Gly Gln Gly Thr Thr Val
                100                 105                 110

Thr Val Ser Ser Ala Ser Thr Lys Gly Pro Ser Val Phe Pro Leu Ala
                115                 120                 125

Pro Cys Ser Arg Ser Thr Ser Glu Ser Thr Ala Ala Leu Gly Cys Leu
                130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
                180                 185                 190

Gly Thr Gln Thr Tyr Thr Cys Asn Val Asp His Lys Pro Ser Asn Thr
                195                 200                 205

Lys Val Asp Lys Thr Val Glu Arg Lys Cys Cys Val Glu Cys Pro Pro
                210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
                260                 265                 270

Tyr Val Asp Gly Val Glu Val His Asn Ala Lys Thr Lys Pro Arg Glu
                275                 280                 285

Glu Gln Phe Asn Ser Thr Phe Arg Val Val Ser Val Leu Thr Val Val
                290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Thr Lys Gly
                325                 330                 335

Gln Pro Arg Glu Pro Gln Val Tyr Thr Leu Pro Pro Ser Arg Glu Glu
                340                 345                 350

Met Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
                370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430
```

```
Gln Lys Ser Leu Ser Leu Ser Pro Gly Lys
        435                 440

<210> SEQ ID NO 12
<211> LENGTH: 219
<212> TYPE: PRT
<213> ORGANISM: Artificial Sequence
<220> FEATURE:
<223> OTHER INFORMATION: Synthetic construct

<400> SEQUENCE: 12

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Tyr Ser
            20                  25                  30

Asp Ala Lys Thr Tyr Leu Asn Trp Phe Gln Gln Arg Pro Gly Gln Ser
        35                  40                  45

Pro Arg Arg Leu Ile Tyr Gln Ile Ser Arg Leu Asp Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Thr His Tyr Pro Val Leu Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 13
<211> LENGTH: 1336
<212> TYPE: DNA
<213> ORGANISM: Artificial Sequence
<220> FEATURE:
<223> OTHER INFORMATION: Synthetic construct

<400> SEQUENCE: 13
caggtgcagc tggtgcagtc tggtgctgag gtgaagaagc ctggcgcttc cgtgaaggtt    60
tcctgcaaag catctggtta ctatacggag gcttactata tccactgggt gcgccaagcc   120
cctggtcaag gcctggagtg gatgggcagg attgatcctg cgactggtaa tactaaatat   180
gccccgaggt tacaggaccg ggtgaccatg actcgcgata cctccaccag cactgtctac   240
atggaactga gctctctgcg ctctgaggac actgctgtgt attactgtgc ctccctttat   300
agtctccctg tctactgggg ccagggtacc actgttaccg tgtcctctgc ctccaccaag   360
ggcccatctg tcttcccact ggccccatgc tcccgcagca cctccgagag cacagccgcc   420
```

```
ctgggctgcc tggtcaagga ctacttccca gaacctgtga ccgtgtcctg gaactctggc      480
gctctgacca gcggcgtgca caccttccca gctgtcctgc agtcctcagg tctctactcc      540
ctcagcagcg tggtgaccgt gccatccagc aacttcggca cccagaccta cacctgcaac      600
gtagatcaca agccaagcaa caccaaggtc gacaagaccg tggagagaaa gtgttgtgtg      660
gagtgtccac cttgtccagc ccctccagtg gccggaccat ccgtgttcct gttccctcca      720
aagccaaagg acaccctgat gatctccaga accccagagg tgacctgtgt ggtggtggac      780
gtgtcccacg aggacccaga ggtgcagttc aactggtatg tggacggagt ggaggtgcac      840
aacgccaaga ccaagccaag agaggagcag ttcaactcca ccttcagagt ggtgagcgtg      900
ctgaccgtgg tgcaccagga ctggctgaac ggaaaggagt ataagtgtaa ggtgtccaac      960
aagggactgc catccagcat cgagaagacc atctccaaga ccaagggaca gccaagagag     1020
ccacaggtgt ataccctgcc ccatccagag gaggagatga ccaagaacca ggtgtccctg     1080
acctgtctgg tgaagggatt ctatccatcc gacatcgccg tggagtggga gtccaacgga     1140
cagccagaga caactataaa gaccaccccc ccaatgctgg actccgacgg atccttcttc     1200
ctgtattcca agctgaccgt ggacaagtcc agatggcagc agggaaacgt gttctcttgt     1260
tccgtgatgc acgaggccct gcacaaccac tatacccaga gagcctgtc cctgtctcca      1320 ggaaagtaat tctaga                                                     1336

<210> SEQ ID NO 14
<211> LENGTH: 666
<212> TYPE: DNA
<213> ORGANISM: Artificial Sequence
<220> FEATURE:
<223> OTHER INFORMATION: Synthetic construct

<400> SEQUENCE: 14
gatgttgtga tgacccagtc cccactgtct ttgccagtta ccctgggaca accagcctcc       60
atatcttgca gtcaagtca gagcctctta tatagtgatg ccaagacata tttgaattgg      120
ttccaacaga ggcctggcca gtctccacgc cgcctaatct atcagatttc cggctggac      180 cctggcgtgc ctgacaggtt cagtggcagt ggatcaggca cagattttac acttaaaatc      240
agcagagtgg aggctgaaga tgtgggagtt tattactgct acaaggtac acattatccg      300 gtgctcttcg gtcaagggac cgcctggag atcaaacgca ctgtggctgc accatctgtc       360
ttcatcttcc ctccatctga tgagcagttg aaatccggaa ctgcctctgt tgtgtgcctg      420
ctgaataact tctatccacg cgaggccaaa gtacagtgga aggtggataa cgccctccaa      480
tccggtaact cccaggagag tgtcacagag caggacagca aggacagcac ctacagcctc      540
agcagcaccc tgaccctgag caaagcagac tacgagaaac acaaagtcta cgcctgcgaa      600
gtcacccatc agggcctgag ttctccagtc acaaagagct caaccgcggt gagtgctaa     660 ttctag                                                                666

<210> SEQ ID NO 15
<211> LENGTH: 40
<212> TYPE: PRT
<213> ORGANISM: Homo sapiens

<400> SEQUENCE: 15

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
```

```
                    20                  25                  30

Gly Leu Met Val Gly Gly Val Val
        35                  40

<210> SEQ ID NO 16
<211> LENGTH: 42
<212> TYPE: PRT
<213> ORGANISM: Homo sapiens

<400> SEQUENCE: 16

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
        35                  40

<210> SEQ ID NO 17
<211> LENGTH: 43
<212> TYPE: PRT
<213> ORGANISM: Homo sapiens

<400> SEQUENCE: 17

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
        35                  40

<210> SEQ ID NO 18
<211> LENGTH: 41
<212> TYPE: PRT
<213> ORGANISM: Homo sapiens

<400> SEQUENCE: 18

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile
        35                  40

<210> SEQ ID NO 19
<211> LENGTH: 39
<212> TYPE: PRT
<213> ORGANISM: Homo sapiens

<400> SEQUENCE: 19

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val
        35

<210> SEQ ID NO 20
<211> LENGTH: 40
<212> TYPE: PRT
<213> ORGANISM: Artificial Sequence
<220> FEATURE:
```

```
<223> OTHER INFORMATION: Synthetic construct

<400> SEQUENCE: 20

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Ala Val Gly Gly Val Val
        35                  40

<210> SEQ ID NO 21
<211> LENGTH: 40
<212> TYPE: PRT
<213> ORGANISM: Artificial Sequence
<220> FEATURE:
<223> OTHER INFORMATION: Synthetic construct

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Ala Gly Gly Val Val
        35                  40

<210> SEQ ID NO 22
<211> LENGTH: 40
<212> TYPE: PRT
<213> ORGANISM: Artificial Sequence
<220> FEATURE:
<223> OTHER INFORMATION: Synthetic construct

<400> SEQUENCE: 22

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Ala Gly Val Val
        35                  40

<210> SEQ ID NO 23
<211> LENGTH: 40
<212> TYPE: PRT
<213> ORGANISM: Artificial Sequence
<220> FEATURE:
<223> OTHER INFORMATION: Synthetic construct

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Ala Val Val
        35                  40

<210> SEQ ID NO 24
<211> LENGTH: 40
<212> TYPE: PRT
<213> ORGANISM: Artificial Sequence
<220> FEATURE:
<223> OTHER INFORMATION: Synthetic construct

<400> SEQUENCE: 24
```

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Ala Val
            35                  40
```

<210> SEQ ID NO 25
<211> LENGTH: 40
<212> TYPE: PRT
<213> ORGANISM: Artificial Sequence
<220> FEATURE:
<223> OTHER INFORMATION: Synthetic construct

<400> SEQUENCE: 25

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Ala
            35                  40
```

<210> SEQ ID NO 26
<211> LENGTH: 120
<212> TYPE: PRT
<213> ORGANISM: Artificial Sequence
<220> FEATURE:
<223> OTHER INFORMATION: Synthetic construct

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Ala Ile His Trp Val Arg Gln Ala Pro Gly Gln Gly Leu Glu Trp Met
            35                  40                  45

Gly Phe Thr Ser Pro Tyr Ser Gly Val Ser Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Phe Asp Asn Tyr Asp Arg Gly Tyr Val Arg Asp Tyr Trp Gly
                100                 105                 110

Gln Gly Thr Leu Val Thr Val Ser
            115                 120
```

<210> SEQ ID NO 27
<211> LENGTH: 114
<212> TYPE: PRT
<213> ORGANISM: Artificial Sequence
<220> FEATURE:
<223> OTHER INFORMATION: Synthetic construct

<400> SEQUENCE: 27

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Asp
                20                  25                  30
```

```
Arg Ile Ser Phe Leu Asn Trp Tyr Gln Gln Lys Pro Gly Gln Pro Pro
            35                  40                  45

Lys Leu Leu Ile Tyr Ala Ala Thr Lys Gln Gly Thr Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Phe Pro Trp Ser Phe Gly Gly Gly Thr Lys Val Glu Ile Lys Arg
            100                 105                 110

Thr Val

<210> SEQ ID NO 28
<211> LENGTH: 10
<212> TYPE: PRT
<213> ORGANISM: Homo sapiens

<400> SEQUENCE: 28

Gly Tyr Thr Phe Thr Thr Tyr Ala Ile His
 1               5                  10

<210> SEQ ID NO 29
<211> LENGTH: 17
<212> TYPE: PRT
<213> ORGANISM: Artificial Sequence
<220> FEATURE:
<223> OTHER INFORMATION: Synthetic construct

<400> SEQUENCE: 29

Phe Thr Ser Pro Tyr Ser Gly Val Ser Asn Tyr Asn Gln Lys Phe Lys
 1               5                  10                  15

Gly

<210> SEQ ID NO 30
<211> LENGTH: 12
<212> TYPE: PRT
<213> ORGANISM: Artificial Sequence
<220> FEATURE:
<223> OTHER INFORMATION: Synthetic construct

<400> SEQUENCE: 30

Phe Asp Asn Tyr Asp Arg Gly Tyr Val Arg Asp Tyr
 1               5                  10

<210> SEQ ID NO 31
<211> LENGTH: 15
<212> TYPE: PRT
<213> ORGANISM: Artificial Sequence
<220> FEATURE:
<223> OTHER INFORMATION: Synthetic construct

<400> SEQUENCE: 31

Arg Ala Ser Glu Ser Val Asp Asn Asp Arg Ile Ser Phe Leu Asn
 1               5                  10                  15

<210> SEQ ID NO 32
<211> LENGTH: 7
<212> TYPE: PRT
<213> ORGANISM: Artificial Sequence
<220> FEATURE:
<223> OTHER INFORMATION: Synthetic construct

<400> SEQUENCE: 32
```

```
<210> SEQ ID NO 33
<211> LENGTH: 9
<212> TYPE: PRT
<213> ORGANISM: Artificial Sequence
<220> FEATURE:
<223> OTHER INFORMATION: Synthetic construct

<400> SEQUENCE: 33

Gln Gln Ser Lys Glu Phe Pro Trp Ser
 1               5

<210> SEQ ID NO 34
<211> LENGTH: 360
<212> TYPE: DNA
<213> ORGANISM: Artificial Sequence
<220> FEATURE:
<223> OTHER INFORMATION: Synthetic construct

<400> SEQUENCE: 34
caggtgcaac tggtgcaatc cggtgccgag gtgaaaaagc caggcgcctc cgtgaaagtg      60
tcctgcaaag cctccggtta cacctttacc acctatgcca tcattgggt gcgccaggcc     120 ccaggccagg gtctggagtg gatgggcttt acttccccct actccggggt gtcgaattac     180
aatcagaagt tcaaaggccg cgtcaccatg accgcgaca cctccacctc cacagtgtat     240
atggagctgt cctctctgcg ctccgaagac accgccgtgt attactgtgc cgcttcgac      300 aattacgatc gcggctatgt gcgtgactat tggggccagg gcaccctggt caccgtctcc     360

<210> SEQ ID NO 35
<211> LENGTH: 342
<212> TYPE: DNA
<213> ORGANISM: Artificial Sequence
<220> FEATURE:
<223> OTHER INFORMATION: Synthetic construct

<400> SEQUENCE: 35
gacatcgtga tgacccagtc cccagactcc ctggccgtgt ccctgggcga gcgcgccacc      60
atcaactgcc gcgccagcga atccgtggat aacgatcgta tttccttct gaactggtac     120 cagcagaaac aggccagcc tcctaagctg ctcatttacg ccgccaccaa acagggtacc     180
ggcgtgcctg accgcttctc cggcagcggt tccggcaccg atttcactct gaccatctcc     240
tccctgcagg ccgaagatgt ggcagtgtat tactgtcagc agtccaaaga gtttccctgg     300
tcctttggcg gtggcaccaa ggtggagatc aaacgcactg tg                        342

<210> SEQ ID NO 36
<211> LENGTH: 447
<212> TYPE: PRT
<213> ORGANISM: Artificial Sequence
<220> FEATURE:
<223> OTHER INFORMATION: Synthetic construct

<400> SEQUENCE: 36

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                20                  25                  30

Ala Ile His Trp Val Arg Gln Ala Pro Gly Gln Gly Leu Glu Trp Met
            35                  40                  45
```

Ala Ala Thr Lys Gln Gly Thr
 1               5

```
Gly Phe Thr Ser Pro Tyr Ser Gly Val Ser Asn Tyr Asn Gln Lys Phe
 50                  55                  60
Lys Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Phe Asp Asn Tyr Asp Arg Gly Tyr Val Arg Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Asn Phe Gly Thr Gln Thr Tyr Thr Cys Asn Val Asp His
        195                 200                 205
Lys Pro Ser Asn Thr Lys Val Asp Lys Thr Val Glu Arg Lys Cys Cys
210                 215                 220
Val Glu Cys Pro Pro Cys Pro Ala Pro Pro Val Ala Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Phe Arg Val Val Ser
290                 295                 300
Val Leu Thr Val Val His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Thr Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Met Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 37
<211> LENGTH: 218
<212> TYPE: PRT
```

<213> ORGANISM: Artificial Sequence
<220> FEATURE:
<223> OTHER INFORMATION: Synthetic construct

<400> SEQUENCE: 37

```
Asp Ile Val Met Thr Gln Ser Pro Asp Ser Leu Ala Val Ser Leu Gly
  1               5                  10                  15

Glu Arg Ala Thr Ile Asn Cys Arg Ala Ser Glu Ser Val Asp Asn Asp
             20                  25                  30

Arg Ile Ser Phe Leu Asn Trp Tyr Gln Gln Lys Pro Gly Gln Pro Pro
         35                  40                  45

Lys Leu Leu Ile Tyr Ala Ala Thr Lys Gln Gly Thr Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Lys
                 85                  90                  95

Glu Phe Pro Trp Ser Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215
```

<210> SEQ ID NO 38
<211> LENGTH: 1341
<212> TYPE: DNA
<213> ORGANISM: Artificial Sequence
<220> FEATURE:
<223> OTHER INFORMATION: Synthetic construct

<400> SEQUENCE: 38

```
caggtgcaac tggtgcaatc cggtgccgag gtgaaaaagc caggcgcctc cgtgaaagtg     60
tcctgcaaag cctccggtta cacctttacc acctatgcca tccattgggt gcgccaggcc    120
ccaggccagg gtctggagtg gatgggcttt acttcccccct actccggggt gtcgaattac    180
aatcagaagt tcaaaggccg cgtcaccatg acccgcgaca cctccacctc cacagtgtat    240
atggagctgt cctctctgcg ctccgaagac accgccgtgt attactgtgc ccgcttcgac    300
aattacgatc gcggctatgt gcgtgactat tggggccagg gcaccctggt caccgtctcc    360
tcagcctcca ccaagggccc atctgtcttc ccactggccc catgctcccg cagcacctcc    420
gagagcacag ccgccctggg ctgcctggtc aaggactact ccccagaacc tgtgaccgtg    480
tcctggaact ctggcgctct gaccagcggc gtgcacacct cccagctgtg cctgcagtcc    540
tcaggtctct actccctcag cagcgtggtg accgtgccat ccagcaactt cggcacccag    600
acctacacct gcaacgtaga tcacaagcca agcaacacca aggtcgacaa gaccgtggag    660
```

```
agaaagtgtt gtgtggagtg tccaccttgt ccagcccctc cagtggccgg accatccgtg    720
ttcctgttcc ctccaaagcc aaggacacc ctgatgatct ccagaacccc agaggtgacc    780
tgtgtggtgg tggacgtgtc ccacgaggac cagaggtgc agttcaactg gtatgtggac    840
ggagtggagg tgcacaacgc caagaccaag ccaagagagg agcagttcaa ctccaccttc    900
agagtggtga gcgtgctgac cgtggtgcac caggactggc tgaacggaaa ggagtataag    960
tgtaaggtgt ccaacaaggg actgccatcc agcatcgaga agaccatctc caagaccaag   1020
ggacagccaa gagagccaca ggtgtatacc ctgcccccat ccagagagga gatgaccaag   1080
aaccaggtgt ccctgacctg tctggtgaag ggattctatc catccgacat cgccgtggag   1140
tgggagtcca acggacagcc agagaacaac tataagacca cccctccaat gctggactcc   1200
gacggatcct tcttcctgta ttccaagctg accgtggaca agtccagatg gcagcaggga   1260
aacgtgttct cttgttccgt gatgcacgag gccctgcaca accactatac ccagaagagc   1320
ctgtccctgt ctccaggaaa g                                             1341
```

<210> SEQ ID NO 39
<211> LENGTH: 654
<212> TYPE: DNA
<213> ORGANISM: Artificial Sequence
<220> FEATURE:
<223> OTHER INFORMATION: Synthetic construct

<400> SEQUENCE: 39

```
gacatcgtga tgacccagtc cccagactcc ctggccgtgt ccctgggcga gcgcgccacc     60
atcaactgcc gcgccagcga atccgtggat aacgatcgta tttcctttct gaactggtac    120
cagcagaaac aggccagcc tcctaagctg ctcatttacg ccgccaccaa acagggtacc    180
ggcgtgcctg accgcttctc cggcagcggt tccggcaccg atttcactct gaccatctcc    240
tccctgcagg ccgaagatgt ggcagtgtat tactgtcagc agtccaaaga gtttcctctgg    300 tcctttggcg gtggcaccaa ggtggagatc aaacgcactg tggctgcacc atctgtcttc    360
atcttccctc catctgatga gcagttgaaa tccggaactg cctctgttgt gtgcctgctg    420
aataacttct atcccagcga ggccaaagta cagtggaagg tggataacgc cctccaatcc    480
ggtaactccc aggagagtgt cacagagcag gacagcaagg acagcaccta cagcctcagc    540
agcaccctga ccctgagcaa agcagactac gagaaacaca aagtctacgc ctgcgaagtc    600
acccatcagg gcctgagttc tccagtcaca aagagcttca accgcggtga gtgc          654
```

<210> SEQ ID NO 40
<211> LENGTH: 15
<212> TYPE: PRT
<213> ORGANISM: Artificial Sequence
<220> FEATURE:
<223> OTHER INFORMATION: Synthetic construct

<400> SEQUENCE: 40

Gly Gly Gly Gly Ser Gly Gly Gly Gly Ser Gly Gly Gly Gly Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Synthetic construct

<400> SEQUENCE: 41

```
Phe Phe Ala Glu Asp Val Gly Ser Asn Lys Gly Ala Ile Ile Gly Gly
 1               5                  10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic construct

<400> SEQUENCE: 42

Phe Ala Glu Asp Val Gly Ser Asn Lys Gly Ala Ile Ile Gly Leu Gly
 1               5                  10                  15

<210> SEQ ID NO 43
<211> LENGTH: 16
<212> TYPE: PRT
<213> ORGANISM: Artificial Sequence
<220> FEATURE:
<223> OTHER INFORMATION: Synthetic construct

<400> SEQUENCE: 43

Ala Glu Asp Val Gly Ser Asn Lys Gly Ala Ile Ile Gly Leu Met Gly
 1               5                  10                  15

<210> SEQ ID NO 44
<211> LENGTH: 16
<212> TYPE: PRT
<213> ORGANISM: Artificial Sequence
<220> FEATURE:
<223> OTHER INFORMATION: Synthetic construct

<400> SEQUENCE: 44

Glu Asp Val Gly Ser Asn Lys Gly Ala Ile Ile Gly Leu Met Val Gly
 1               5                  10                  15

<210> SEQ ID NO 45
<211> LENGTH: 16
<212> TYPE: PRT
<213> ORGANISM: Artificial Sequence
<220> FEATURE:
<223> OTHER INFORMATION: Synthetic construct

<400> SEQUENCE: 45

Asp Val Gly Ser Asn Lys Gly Ala Ile Ile Gly Leu Met Val Gly Gly
 1               5                  10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic construct

<400> SEQUENCE: 46

Val Gly Ser Asn Lys Gly Ala Ile Ile Gly Leu Met Val Gly Gly Gly
 1               5                  10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic construct

<400> SEQUENCE: 47
```

```
Gly Ser Asn Lys Gly Ala Ile Ile Gly Leu Met Val Gly Gly Val Gly
 1               5                  10                  15
```

<210> SEQ ID NO 48
<211> LENGTH: 16
<212> TYPE: PRT
<213> ORGANISM: Artificial Sequence
<220> FEATURE:
<223> OTHER INFORMATION: Synthetic construct

<400> SEQUENCE: 48

```
Ser Asn Lys Gly Ala Ile Ile Gly Leu Met Val Gly Gly Val Val Gly
 1               5                  10                  15
```

<210> SEQ ID NO 49
<211> LENGTH: 16
<212> TYPE: PRT
<213> ORGANISM: Artificial Sequence
<220> FEATURE:
<223> OTHER INFORMATION: Synthetic construct

<400> SEQUENCE: 49

```
Asn Lys Gly Ala Ile Ile Gly Leu Met Val Gly Gly Val Val Ile Gly
 1               5                  10                  15
```

<210> SEQ ID NO 50
<211> LENGTH: 16
<212> TYPE: PRT
<213> ORGANISM: Artificial Sequence
<220> FEATURE:
<223> OTHER INFORMATION: Synthetic construct

<400> SEQUENCE: 50

```
Lys Gly Ala Ile Ile Gly Leu Met Val Gly Gly Val Val Ile Ala Gly
 1               5                  10                  15
```

<210> SEQ ID NO 51
<211> LENGTH: 11
<212> TYPE: PRT
<213> ORGANISM: Artificial Sequence
<220> FEATURE:
<223> OTHER INFORMATION: Synthetic construct

<400> SEQUENCE: 51

```
Val Gly Ser Asn Lys Gly Ala Ile Ile Gly Gly
 1               5                  10
```

<210> SEQ ID NO 52
<211> LENGTH: 11
<212> TYPE: PRT
<213> ORGANISM: Artificial Sequence
<220> FEATURE:
<223> OTHER INFORMATION: Synthetic construct

<400> SEQUENCE: 52

```
Gly Ser Asn Lys Gly Ala Ile Ile Gly Leu Gly
 1               5                  10
```

<210> SEQ ID NO 53
<211> LENGTH: 11
<212> TYPE: PRT
<213> ORGANISM: Artificial Sequence
<220> FEATURE:
<223> OTHER INFORMATION: Synthetic construct

```
<400> SEQUENCE: 53

Ser Asn Lys Gly Ala Ile Ile Gly Leu Met Gly
1               5                   10
```